United States Patent
Hurnaus et al.

(10) Patent No.: US 7,538,115 B2
(45) Date of Patent: May 26, 2009

(54) SUBSTITUTED PIPERIDINES, PHARMACEUTICAL COMPOSITIONS CONTAINING THESE COMPOUNDS, THEIR USE AND PROCESSES FOR THE PREPARATION THEREOF

(75) Inventors: Rudolf Hurnaus, Biberach (DE); Klaus Rudolf, Warthausen (DE); Stephan Georg Mueller, Warthausen (DE); Dirk Stenkamp, Biberach (DE); Philipp Lustenberger, Basel (CH); Alexander Dreyer, Gutenzell-Huerbel (DE); Kai Gerlach, Mittelbiberach (DE); Marcus Schindler, Biberach (DE); Kirsten Arndt, Biberach (DE); Eckhart Bauer, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 413 days.

(21) Appl. No.: 11/138,868

(22) Filed: May 26, 2005

(65) Prior Publication Data
US 2005/0215546 A1 Sep. 29, 2005

Related U.S. Application Data

(62) Division of application No. 10/388,273, filed on Mar. 13, 2003, now Pat. No. 7,026,312.

(60) Provisional application No. 60/396,660, filed on Jul. 17, 2002.

(30) Foreign Application Priority Data
Mar. 14, 2002 (DE) .................. 102 11 770

(51) Int. Cl.
A61K 31/517 (2006.01)
C07D 239/72 (2006.01)

(52) U.S. Cl. ..................... 514/266.22; 544/286
(58) Field of Classification Search ............ 514/266.22; 544/286
See application file for complete search history.

(56) References Cited

U.S. PATENT DOCUMENTS 6,344,449 B1 2/2002 Rudolf et al.
6,521,609 B1 2/2003 Doods et al.

FOREIGN PATENT DOCUMENTS

WO WO 98/11128 A1 3/1998

OTHER PUBLICATIONS

Rudolf et al. "Preparation of naphthalenes . . . " CA134:340521 (2001).*
Rudolph et al. J. Med. Chem. v.50, pp. 5202-5216 (2007).*
Verheggen et al. "BIBN4096BS . . . " Bri. J. Pharmacol. v.136, p. 120-126 (2002).*
Thurieau, C. et al: Preparation of Imidazoly derivatives as agonists or antagonists of somatostatin receptors; CA 132:35701 (1999).

* cited by examiner

Primary Examiner—Celia Chang
(74) Attorney, Agent, or Firm—Michael P. Morris; Mary-Ellen M. Devlin; Alan R. Stempel

(57) ABSTRACT

The present invention relates to substituted piperidines of general formula (I)

wherein R, $R^2$ to $R^5$, A, X, Z and n are defined as in claim 1, the tautomers, diastereomers, enantiomers, mixtures and salts thereof, particularly the physiologically acceptable salts thereof with inorganic or organic acids or bases which have valuable pharmacological properties, particularly CGRP-antagonistic properties, pharmaceutical compositions containing these compounds, the use thereof and processes for the preparation thereof.

14 Claims, No Drawings

SUBSTITUTED PIPERIDINES, PHARMACEUTICAL COMPOSITIONS CONTAINING THESE COMPOUNDS, THEIR USE AND PROCESSES FOR THE PREPARATION THEREOF

RELATED APPLICATIONS

Benefit of U.S. Provisional Application Ser. No. 60/396,660, filed on Jul. 17, 2002 is hereby claimed, and said application is herein incorporated by reference.

FIELD OF INVENTION

The present invention relates to CGRP-antagonists.

BACKGROUND OF THE INVENTION cGRP antagonists are useful compounds for the treatment of many diseases such as cardiovascular disease, morphine tolerance, skin diseases and various inflammatory diseases. cGRP antagonists have been described in U.S. Pat. No. 6,344,449 incorporated herein.

DESCRIPTION OF THE INVENTION

The present invention relates to new substituted piperidines of general formula

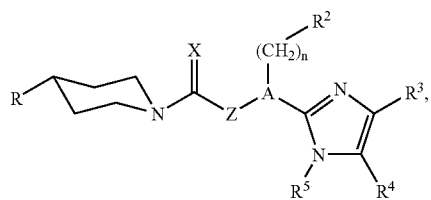

the tautomers, the diastereomers, the enantiomers, the mixtures thereof and the salts thereof, particularly the physiologically acceptable salts thereof with inorganic or organic acids or bases, pharmaceutical compositions containing these compounds, their use and processes for preparing them.

In the above general formula (I)

R denotes a saturated, monounsaturated or, in the case of the 6- and 7-membered heterocyclic groups, a diunsaturated 5- to 7-membered aza, diaza, triaza, oxaza, thiaza, thiadiaza or S,S-dioxido-thiadiaza-heterocyclic group, while the abovementioned heterocyclic groups are linked via a carbon or nitrogen atom and contain one or two carbonyl groups, which are linked to at least one nitrogen atom, may be substituted by an alkyl group at one of the nitrogen atoms, may be substituted at one or two carbon atoms in each case by an alkyl, phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl group, while the substituents may be identical or different, and wherein a double bond of one of the abovementioned unsaturated heterocyclic groups may be fused to a benzene, pyridine, diazine, 1,3-oxazole, thiophene, furan, thiazole, pyrrole, N-methyl-pyrrole or quinoline ring, to a 2(1H)-oxoquinoline ring optionally substituted by an alkyl group at the nitrogen atom or to an imidazole or N-methyl-imidazole ring, or also two olefinic double bonds of one of the abovementioned unsaturated heterocyclic groups may be fused to a benzene ring in each case, while the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in R as well as benzo-, thieno-, pyrido- and diazino-fused heterocyclic groups in the carbon skeleton may additionally be mono-, di- or trisubstituted by fluorine, chlorine, bromine or iodine atoms, by alkyl, alkoxy, nitro, alkylthio, alkylsulphinyl, alkylsulphonyl, alkylsulphonylamino, phenyl, trifluoromethyl, difluoromethyl, difluoromethoxy, alkoxycarbonyl, carboxy, dialkylamino, hydroxy, amino, acetylamino, propionylamino, aminocarbonyl, alkylaminocarbonyl, dialkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, alkanoyl, cyano, trifluoromethoxy, trifluoromethylthio, trifluoromethylsulphinyl or trifluoromethylsulphonyl groups, while the substituents may be identical or different, X denotes an oxygen atom or, if Z denotes the group —NR$^1$—, it may also denote one of the groups =N—CN or =N—SO$_2$—R$^6$, wherein R$^6$ denotes an alkyl group with 1 to 4 carbon atoms or a phenyl group optionally substituted by a halogen atom, a methyl or a methoxy group, Z denotes one of the groups —CH$_2$, wherein the hydrogen atoms may be replaced independently of one another by a fluorine atom or a C$_{1-3}$-alkyl group, or —NR$^1$, wherein R$^1$ denotes the hydrogen atom, an alkyl group which may be substituted in the alkyl moiety with the exception of position 1 by an amino, C$_{1-3}$-alkyl-amino or di-(C$_{1-3}$-alkyl)-amino group, or a phenylalkyl group which may be mono- or disubstituted in the phenyl moiety by fluorine, chlorine, bromine or iodine atoms, by a C$_{1-3}$-alkyl, trifluoromethyl, difluoromethyl, cyclopropyl, hydroxy, C$_{1-3}$-alkoxy, difluoromethoxy, trifluoromethoxy, cyano, nitro, amino, C$_{1-3}$-alkyl-amino, di-(C$_{1-3}$-alkyl)-amino, carboxy, C$_{1-3}$-alkoxycarbonyl, aminocarbonyl, C$_{1-3}$-alkyl-aminocarbonyl, di-(C$_{1-3}$-alkyl)-aminocarbonyl, amino-C$_{1-3}$-alkyl, C$_{1-3}$-alkyl-amino-C$_{1-3}$-alkyl or di-(C$_{1-3}$-alkyl)-amino-C$_{1-3}$-alkyl group, while the substituents may be identical or different, A denotes a carbon atom substituted by a hydrogen atom or by a C$_{1-3}$-alkyl group n denotes the number 1 or 2, R$^2$ denotes the group

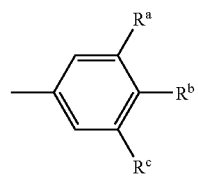

wherein one of the groups R$^a$, R$^b$ and R$^c$ denotes the hydrogen, fluorine, chlorine, bromine or iodine atom, a branched or unbranched alkyl group, a hydroxy, alkoxy, trifluoromethyl, difluoromethyl, trifluoromethoxy, difluoromethoxy, trifluoromethylthio, amino, acetylamino, dialkylaminoalkyl, dialkylaminoalkoxy, nitro, methylsulphonyloxy, aminocarbonyl, alkylaminocarbonyl, dialkylaminocarbonyl, alkanoyl, cyano, trifluoromethylsulphinyl or trifluoromethylsulphonyl group, a second of the groups $R^a$, $R^b$ and $R^c$ denotes the hydrogen, fluorine, chlorine, bromine or iodine atom, a branched or unbranched alkyl group, a hydroxy, alkoxy, trifluoromethyl, difluoromethyl, trifluoromethoxy, difluoromethoxy, trifluoromethylthio, amino, acetylamino, alkanoyl, aminocarbonyl, alkyl-aminocarbonyl or dialkylaminocarbonyl group and the third of the groups $R^a$, $R^b$ and $R^c$ denotes the hydrogen, fluorine, chlorine, bromine or iodine atom, a branched or unbranched alkyl group, a hydroxy, alkoxy, trifluoromethyl, difluoromethyl, difluoromethoxy, or trifluoromethoxy group, while the substituents may be identical or different, $R^3$ and $R^4$, which may be identical or different, in each case denote the hydrogen atom, a $C_{1-4}$-alkyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, a phenyl or naphthyl group which in each case may be mono- or disubstituted by $R^d$, while the substituents may be identical or different and $R^d$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or a 4- to 7-membered cycloalkyleneimino-carbonyl group wherein one or two hydrogen atoms may each be replaced by a $C_{1-3}$-alkyl group and/or in each case the methylene group in the 4 position of a 6- or 7-membered cycloalkyleneimino moiety may be replaced by an oxygen or sulphur atom, by a sulphinyl, sulphonyl, —NH, —N($C_{1-3}$-alkyl) or —N($C_{1-3}$-alkyl-carbonyl)-group, a monocyclic 5- or 6-membered heteroaryl group optionally substituted in the carbon skeleton by a $C_{1-3}$-alkyl, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, while the 6-membered heteroaryl group contains one, two or three nitrogen atoms and may optionally additionally be substituted by a fluorine, chlorine, bromine or iodine atom, a $C_{1-3}$-alkyl, $C_{1-3}$-alkoxy, amino, $C_{1-3}$-alkylamino or di-($C_{1-3}$-alkyl)amino group and the 5-membered heteroaryl group contains an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, an oxygen or sulphur atom or an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or an oxygen or sulphur atom and additionally a nitrogen atom or an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group and two nitrogen atoms, or $R^3$ and $R^4$ together denote a 1,3-butadien-1,4-ylene group wherein one, two or three methyne groups may each be replaced by a nitrogen atom, a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, di-($C_{1-3}$-alkyl)-amino-$C_{2-3}$-alkyl-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or by a 4- to 7-membered cycloalkyleneimino-carbonyl group wherein one or two hydrogen atoms may each be replaced by a $C_{1-3}$-alkyl group and/or in each case the methylene group in the 4 position of a 6- or 7-membered cycloalkyleneimino moiety may be replaced by an oxygen or sulphur atom, by a sulphinyl, sulphonyl, —NH, —N($C_{1-3}$-alkyl) or —N($C_{1-3}$-alkyl-carbonyl)-group, and optionally additionally a second hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy or trifluoromethoxy group, and $R^5$ denotes the group —$(CH_2)_m$—$R^e$, wherein m denotes the number 0 and $R^e$ denotes a hydrogen atom, a phenyl or naphthyl group which in each case may be mono- or disubstituted by $R^f$, while the substituents may be identical or different and $R^f$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino -$C_{1-3}$-alkyl group, or a pyridinyl, pyrazinyl, pyrimidinyl, pyridazinyl, pyrrolyl, furyl, thienyl, pyrazolyl, imidazolyl, oxazolyl, isoxazolyl, thiazolyl or isothiazolyl group optionally substituted in the carbon skeleton by a $C_{1-3}$-alkyl group, wherein a hydrogen atom bound to a nitrogen atom may be replaced by a $C_{1-3}$-alkyl or acetyl group, or a $C_{3-7}$-cycloalkyl group, while a hydrogen atom of the $C_{3-7}$-cycloalkyl group may be replaced by an amino, $C_{1-3}$-alkyl-amino, di-($C_{1-3}$-alkyl)-amino, amino-$C_{1-3}$-alkyl, $C_{1-3}$-alkyl-amino-$C_{1-3}$-alkyl or di-($C_{1-3}$-alkyl)-amino-$C_{1-3}$-alkyl group and/or the methylene group in the 3 position of the cyclopentyl group and the methylene group in the 4 position of the cyclohexyl and cycloheptyl group may each be replaced by an oxygen or sulphur atom, by a sulphinyl, sulphonyl, —NH, —N($C_{1-3}$-alkyl) or —N($C_{1-3}$-alkyl-carbonyl)- group, or m denotes one of the numbers 1 to 5 and
$R^e$ denotes a hydrogen atom, an aminomethylene, $C_{1-3}$-alkylaminomethylene, di-($C_{1-3}$-alkyl)-aminomethylene, aminocarbonyl, $C_{1-3}$-alkylaminocarbonyl, di-($C_{1-3}$-alkyl)-aminocarbonyl or $C_{3-7}$-cycloalkyl group, while
a hydrogen atom of the $C_{3-7}$-cycloalkyl group may be replaced by an amino, $C_{1-3}$-alkyl-amino, di-($C_{1-3}$-alkyl)-amino, amino-$C_{1-3}$-alkyl, $C_{1-3}$-alkyl-amino-$C_{1-3}$-alkyl or di-($C_{1-3}$-alkyl)-amino-$C_{1-3}$-alkyl group and/or
the methylene group in the 3 position of the cyclopentyl group and the methylene group in the 4 position of the cyclohexyl and cycloheptyl group may each be replaced by an oxygen or sulphur atom, by a sulphinyl, sulphonyl, —NH, —N($C_{1-3}$-alkyl) or —N($C_{1-3}$-alkyl-carbonyl)- group, a 4- to 7-membered cycloalkyleneimino group wherein
one or two hydrogen atoms may each be replaced by a $C_{1-3}$-alkyl group and/or
in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl) or —N($C_{1-3}$-alkyl-carbonyl)-group, a phenyl or naphthyl group which may be mono- or disubstituted by $R^g$ in each case independently of one another, while the substituents may be identical or different and $R^g$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or a monocyclic 5- or 6-membered heteroaryl group optionally substituted in the carbon skeleton by a $C_{1-3}$-alkyl, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, while
the 6-membered heteroaryl group contains one, two or three nitrogen atoms and may optionally additionally be substituted by a fluorine, chlorine, bromine or iodine atom, a $C_{1-3}$-alkyl, $C_{1-3}$-alkoxy, amino, $C_{1-3}$-alkylamino or di-($C_{1-3}$-alkyl)amino group and
the 5-membered heteroaryl group contains an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, an oxygen or sulphur atom or
an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or an oxygen or sulphur atom and additionally a nitrogen atom or an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group and two nitrogen atoms, while the abovementioned alkyl groups or the alkyl groups contained in the abovementioned groups, unless otherwise stated, contain 1 to 5 carbon atoms and may be branched or unbranched.

For example R may represent the 4-(2-oxo-4-phenyl-2,3-dihydro-imidazol-1-yl), 4-(2-oxo-2,3-dihydro-benzimidazol-1-yl), 4-(2,4-dioxo-1,4-dihydro-2H-quinazolin-3-yl), 4-(2-oxo- 1,2-dihydro-imidazo[4,5-b]pyridin-3-yl), 4-(2-oxo-1,4-di hydro-2H-quinazolin-3-yl), 4-(2-oxo-1,2,4,5-tetrahydro-1,3-benzodiazepin-3-yl), 4-(7-methoxy-2-oxo-1,2,4,5-tetrahydro-1,3-benzodiazepin-3-yl), 4-(2-oxo-1,2-dihydro-quinolin-3-yl), 4-(5-oxo-3-phenyl-4,5-dihydro-1,2,4-triazol-1-yl), 4-(2-oxo-1,2-dihydro-imidazo[4,5-c]quinolin-3-yl) group.

The present invention relates to racemates if the compounds of general formula I have only one chiral element. However, the application also includes the individual diastereomeric pairs of antipodes or mixtures thereof which are obtained if there is more than one chiral element in the compounds of general formula (I), as well as the individual optically active enantiomers of which the abovementioned racemates are made up.

The compounds of general formula (I) have valuable pharmacological properties, based on their selective CGRP-antagonistic properties. The invention further relates to pharmaceutical compositions containing these compounds, their use and the preparation thereof.

One subgroup of compounds of general formula I deserving special mention comprises those wherein R, X, Z, A, n, $R^2$, and $R^5$ are as hereinbefore defined and
$R^3$ denotes the hydrogen atom or a $C_{1-4}$-alkyl group and
$R^4$ denotes the hydrogen atom, a $C_{1-4}$-alkyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group,
a phenyl or naphthyl group which may be mono- or disubstituted by $R^d$ in each case independently of one another, while the substituents may be identical or different and Rd denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or
a monocyclic 5- or 6-membered heteroaryl group optionally substituted in the carbon skeleton by a $C_{1-3}$-alkyl, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, while
the 6-membered heteroaryl group contains one, two or three nitrogen atoms and
the 5-membered heteroaryl group contains an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, an oxygen or sulphur atom or an imino group optionally substituted by a $C_{1-3}$-alkyl, acetyl, trifluoroacetyl-$C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or an oxygen or sulphur atom and additionally a nitrogen atom or an imino group optionally substituted by a $C_{1-3}$-alkyl, acetyl, trifluoroacetyl-$C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group and two nitrogen atoms, the tautomers, diastereomers, enantiomers, mixtures and salts thereof.

A second subgroup of compounds of general formula I deserving particular mention comprises those wherein R, X, Z, A, n, $R^2$, and $R^5$ are as hereinbefore defined and $R^3$ and $R^4$ together denote a 1,3-butadien-1,4-ylene group wherein
one, two or three methyne groups may each be replaced by a nitrogen atom,
a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, di($C_{1-3}$-alkyl)-amino-$C_{2-3}$-alkyl-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or by a 4- to 7-membered cycloalkyleneimino-carbonyl group wherein
one or two hydrogen atoms may each be replaced by a $C_{1-3}$-alkyl group and/or
in each case the methylene group in the 4 position of a 6- or 7-membered cycloalkyleneimino moiety may be replaced by an oxygen or sulphur atom, by a sulphinyl, sulphonyl, —NH, —N($C_{1-3}$-alkyl) or —N($C_{1-3}$-alkyl-carbonyl)-group,
and optionally a second hydrogen atom may additionally be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy or trifluoromethoxy group.

Preferred compounds of the above general formula I are those wherein

R denotes a saturated or monounsaturated 5- to 7-membered aza, diaza, oxaza or thiaza heterocyclic group,
while the abovementioned heterocyclic groups are linked via a nitrogen atom and
contain a carbonyl group linked to one or two nitrogen atoms of the heterocyclic group,
may be substituted by an alkyl group at one of the nitrogen atoms,
may be substituted at one of the carbon atoms by an alkyl, phenyl, pyridinyl, furyl, thienyl or pyrrolyl group,
and wherein a double bond of one of the abovementioned unsaturated heterocyclic groups may be fused to a benzene, pyridine or thiophene ring,
while the phenyl, pyridinyl, furyl, thienyl, pyrrolyl groups contained in R as well as the benzo-, thieno- and pyrido-condensed heterocyclic groups in the carbon skeleton may additionally be mono- or disubstituted by fluorine, chlorine, bromine or iodine atoms, by alkyl, alkoxy, nitro, alkylthio, trifluoromethyl, difluoromethyl, alkoxycarbonyl, carboxy, dialkylamino, hydroxy, amino, acetylamino, aminocarbonyl, alkylaminocarbonyl, alkanoyl, cyano or trifluoromethoxy groups, while the substituents may be identical or different, X denotes an oxygen atom or, if Z the group —$NR^1$— denotes, it may also denote the group =N—CN, Z denotes one of the groups —$CH_2$ or —$NR^1$, wherein $R^1$ denotes the hydrogen atom or an alkyl group, A denotes a carbon atom substituted by a hydrogen atom or by a $C_{1-3}$-alkyl group, n denotes the number 1 or 2, $R^2$ denotes the group

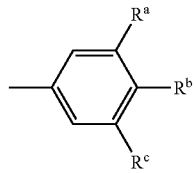

wherein
one of the groups $R^a$, $R^b$ and $R^c$ denotes the hydrogen, fluorine, chlorine, bromine or iodine atom, a branched or unbranched alkyl group, a hydroxy, alkoxy, trifluoromethyl, difluoromethyl, trifluoromethoxy, amino, acetylamino, dialkylaminoalkyl, dialkylaminoalkoxy, aminocarbonyl, alkylaminocarbonyl, dialkylaminocarbonyl, alkanoyl, cyano or trifluoromethylsulphonyl group,
a second of the groups $R^a$, $R^b$ and $R^c$ denotes the hydrogen, fluorine, chlorine, bromine or iodine atom, a branched or unbranched alkyl group, an alkoxy, trifluoromethyl, amino, acetylamino or alkanoyl group and
the third of the groups $R^a$, $R^b$ and $R^c$ denotes the hydrogen, fluorine, chlorine, bromine or iodine atom or a branched or unbranched alkyl group, while the substituents may be identical or different, $R^3$ denotes the hydrogen atom or a $C_{1-3}$-alkyl group, $R^4$ denotes the hydrogen atom, a $C_{1-4}$-alkyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group,
a phenyl group which may be mono- or disubstituted by $R^d$, while the substituents may be identical or different and $R^d$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, amino, $C_{1-3}$-alkylamino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or
a pyridinyl, pyrazinyl, pyrimidinyl, pyridazinyl, pyrrolyl, furyl, thienyl, pyrazolyl, imidazolyl, oxazolyl, isoxazolyl, thiazolyl or isothiazolyl group optionally substituted in the carbon skeleton by a $C_{1-3}$-alkyl group, wherein a hydrogen atom bound to a nitrogen atom may be replaced by a $C_{1-3}$-alkyl or acetyl group, or $R^3$ and $R^4$ together denote a 1,3-butadien-1,4-ylene group wherein
a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, di-($C_{1-3}$-alkyl)-amino-$C_{2-3}$-alkyl-aminocarbonyl, amino-$C_{1-3}$-alkyl, $C_{1-3}$-alkyl-amino-$C_{1-3}$-alkyl, di-($C_{1-3}$-alkyl)-amino-$C_{1-3}$-alkyl group or by a 5- to 7-membered cycloalkyleneimino-carbonyl group wherein one or two hydrogen atoms may each be replaced by a $C_{1-3}$-alkyl group and/or in each case the methylene group in the 4 position of a 6- or 7-membered cycloalkyleneimino moiety by an oxygen or sulphur atom, may be replaced by a —NH, —N($C_{1-3}$-alkyl) or —N($C_{1-3}$-alkyl-carbonyl)- group, and optionally a second hydrogen atom may additionally be replaced by a fluorine, chlorine, bromine or iodine atom, by a $C_{1-3}$-alkyl or trifluoromethyl group, and $R^5$ denotes the group —$(CH_2)_m$—$R^e$, wherein m denotes the number 0 and $R^e$ denotes a hydrogen atom or a $C_{5-6}$-cycloalkyl group, while the methylene group in the 3 position of the cyclopentyl group and the methylene group in the 4 position of the cyclohexyl group may each be replaced by a —NH, —N($C_{1-3}$-alkyl) or —N($C_{1-3}$-alkyl-carbonyl) group, or m denotes one of the numbers 1 to 5 and $R^e$ denotes a hydrogen atom, an aminomethylene, $C_{1-3}$-alkylaminomethylene, di-($C_{1-3}$-alkyl)-aminomethylene, aminocarbonyl, $C_{1-3}$-alkyl-aminocarbonyl, di-($C_{1-3}$-alkyl)-amino carbonyl or $C_{5-6}$-cycloalkyl group, while the methylene group in the 3 position of the cyclopentyl group and the methylene group in the 4 position of the cyclohexyl group may each be replaced by a —NH, —N($C_{1-3}$-alkyl) or —N($C_{1-3}$-alkyl-carbonyl) group, a 5- to 6-membered cycloalkyleneimino group, while the methylene group in the 4 position of a 6-membered cycloalkyleneimino group may be replaced by a —NH, —N($C_{1-3}$-alkyl) or —N($C_{1-3}$-alkyl-carbonyl)- group, a phenyl group which may be mono- or disubstituted by $R^9$, while the substituents may be identical or different and $R^9$ denotes a fluorine, chlorine, bromine or iodine atom, a $C_{1-3}$-alkyl, trifluoromethyl, difluoromethyl, hydroxy, $C_{1-3}$-alkoxy, amino, $C_{1-3}$-alkyl-amino, di-($C_{1-3}$-alkyl)-amino, aminocarbonyl-$C_{1-3}$-alkyl-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or a pyridinyl, pyrazinyl, pyrimidinyl, pyridazinyl, pyrrolyl, furyl, thienyl, pyrazolyl, imidazolyl, oxazolyl, isoxazolyl, thiazolyl or isothiazolyl group optionally substituted in the carbon skeleton by a $C_{1-3}$-alkyl group, wherein a hydrogen atom bound to a nitrogen atom by a $C_{1-3}$-alkyl or acetyl group may be replaced, while the abovementioned alkyl groups or the alkyl groups contained in the abovementioned groups, unless otherwise stated, contain 1 to 4 carbon atoms and may be branched or unbranched, the tautomers, the diastereomers, the enantiomers and the salts thereof.

One subgroup of preferred compounds of general formula I deserving special mention comprises those wherein R, X, Z, A, n, $R^2$, and $R^5$ are as hereinbefore defined and $R^3$ denotes the hydrogen atom or a $C_{1-3}$-alkyl group and $R^4$ denotes a phenyl group which may be mono- or disubstituted by $R^d$, while the substituents may be identical or different and $R^d$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or a pyridinyl, pyrazinyl, pyrimidinyl, pyridazinyl, pyrrolyl, furyl, thienyl, pyrazolyl, imidazolyl, oxazolyl, isoxazolyl, thiazolyl or isothiazolyl group optionally substituted in the carbon skeleton by a $C_{1-3}$-alkyl group, wherein a hydrogen atom bound to a nitrogen atom may be replaced by a $C_{1-3}$-alkyl or acetyl group.

A second subgroup of preferred compounds of general formula I deserving special mention comprises those wherein R, X, Z, A, n, $R^2$, and $R^5$ are as hereinbefore defined and $R^3$ and $R^4$ together denote a 1,3-butadien-1,4-ylene group wherein a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl or di-($C_{1-3}$-alkyl)-amino-$C_{2-3}$-alkyl-aminocarbonyl group or by a 5- to 7-membered cycloalkyleneimino-carbonyl group wherein one or two hydrogen atoms may each be replaced by a $C_{1-3}$-alkyl group and/or in each case the methylene group in the 4 position of a 6- or 7-membered cycloalkyleneimino moiety may be replaced by an oxygen or sulphur atom, by a —NH, —N($C_{1-3}$-alkyl) or —N($C_{1-3}$-alkyl-carbonyl)- group, and optionally a second hydrogen atom may additionally be replaced by a fluorine, chlorine, bromine or iodine atom, by a $C_{1-3}$-alkyl or trifluoromethyl group.

Particularly preferred compounds of the above general formula I are those wherein R denotes a monounsaturated, 5- to 7-membered diaza heterocyclic group linked via a nitrogen atom, while the abovementioned heterocyclic groups contain a carbonyl group linked to both nitrogen atoms of the heterocyclic group, may each be substituted independently of one another at one of the nitrogen atoms and one of the saturated carbon atoms by a $C_{1-3}$-alkyl group, and wherein the double bond of the abovementioned unsaturated heterocyclic groups is fused to a benzene ring optionally substituted by a fluorine, chlorine, bromine or iodine atom, or by a $C_{1-3}$-alkyl, $C_{1-3}$-alkoxy, trifluoromethyl, carboxy, $C_{1-3}$-alkoxy-carbonyl, amino, acetylamino, hydroxy, aminocarbonyl or alkanoyl group, X denotes an oxygen atom, Z denotes one of the groups —$CH_2$ or —$NR^1$ wherein $R^1$ denotes the hydrogen atom or a $C_{1-3}$-alkyl group, A denotes a carbon atom substituted by a hydrogen atom or by a $C_{1-3}$-alkyl group, n denotes the number 1, $R^2$ denotes the group

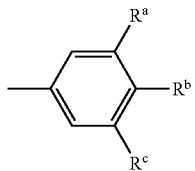

wherein
- one of the groups $R^a$, $R^b$ and $R^c$ denotes the hydrogen, fluorine, chlorine, bromine or iodine atom, a $C_{1-3}$-alkyl, trifluoromethyl, hydroxy, alkoxy or amino group,
- a second of the groups $R^a$, $R^b$ and $R^c$ denotes the hydrogen, fluorine, chlorine, bromine or iodine atom, a $C_{1-3}$-alkyl or trifluoromethyl group and
- the third of the groups Ra, Rb and Rc denotes the hydrogen, fluorine, chlorine, bromine or iodine atom, while the substituents may be identical or different, $R^3$ denotes the hydrogen atom or a $C_{1-3}$-alkyl group, $R^4$ denotes a phenyl group optionally substituted by a fluorine, chlorine, bromine or iodine atom, by a $C_{1-3}$-alkyl, trifluoromethyl, hydroxy, $C_{1-3}$-alkoxy, amino, $C_{1-3}$-alkylamino, di-($C_{1-3}$-alkyl)-amino, carboxy or $C_{1-3}$-alkoxycarbonyl group, or $R^3$ and $R^4$ together denote a 1,3-butadien-1,4-ylene group wherein
- a hydrogen atom may be replaced by a fluorine, chlorine, bromine or iodine atom, by a $C_{1-3}$-alkyl, trifluoromethyl, hydroxy, $C_{1-3}$-alkoxy, carboxy, $C_{1-3}$-alkoxy-carbonyl, aminocarbonyl, $C_{1-3}$-alkyl-aminocarbonyl, di-($C_{1-3}$-alkyl)-aminocarbonyl or di-($C_{1-3}$-alkyl)-amino-$C_{2-3}$-alkyl-aminocarbonyl group or by a 5- to 7-membered cycloalkyleneimino-carbonyl group, while
  - the methylene group in the 4 position of the 6-membered cycloalkyleneimino moiety may be replaced by a —NH, —N($C_{1-3}$-alkyl) or —N($C_{1-3}$-alkyl-carbonyl) group,
- and optionally a second hydrogen atom may additionally be replaced by a fluorine, chlorine, bromine or iodine atom or by a $C_{1-3}$-alkyl group, and $R^5$ denotes the group —$(CH_2)_m$—$R^e$, wherein
- m denotes the number 0 and
- $R^e$ denotes a hydrogen atom,
- or m denotes one of the numbers 1 to 3 and
- $R^e$ denotes a hydrogen atom, an aminomethylene, $C_{1-3}$-alkylaminomethylene or di-($C_{1-3}$-alkyl)-aminomethylene group,
- while the abovementioned alkyl groups or the alkyl groups contained in the abovementioned groups, unless otherwise stated, may be branched or unbranched,
- the tautomers, the diastereomers, the enantiomers and the salts thereof.

A subgroup of particularly preferred compounds of general formula I deserving special mention comprises those wherein R, X, Z, A, n, $R^2$, and $R^5$ are as hereinbefore defined and $R^3$ denotes the hydrogen atom or a $C_{1-3}$-alkyl group and $R^4$ denotes a phenyl group optionally substituted by a fluorine, chlorine, bromine or iodine atom, by a $C_{1-3}$-alkyl, trifluoromethyl, hydroxy, $C_{1-3}$-alkoxy, amino, $C_{1-3}$-alkylamino, di-($C_{1-3}$-alkyl)-amino, carboxy or $C_{1-3}$-alkoxycarbonyl group.

A second subgroup of particularly preferred compounds of general formula I deserving special mention comprises those wherein R, X, Z, A, n, $R^2$, and $R^5$ are as hereinbefore defined and $R^3$ and $R^4$ together denote a 1,3-butadien-1,4-ylene group wherein
- a hydrogen atom may be replaced by a fluorine, chlorine, bromine or iodine atom, by a $C_{1-3}$-alkyl, trifluoromethyl, hydroxy, $C_{1-3}$-alkoxy, carboxy, $C_{1-3}$-alkoxy-carbonyl, aminocarbonyl, $C_{1-3}$-alkyl-aminocarbonyl, di-($C_{1-3}$-alkyl)-aminocarbonyl or di-($C_{1-3}$-alkyl)-amino-$C_{2-3}$-alkyl-aminocarbonyl group or by a 5- to 7-membered cycloalkyleneimino-carbonyl group, while
  - the methylene group in the 4 position of the 6-membered cycloalkyleneimino moiety may be replaced by a —NH, —N($C_{1-3}$-alkyl) or —N($C_{1-3}$-alkyl-carbonyl) group,
- and optionally a second hydrogen atom may additionally be replaced by a fluorine, chlorine, bromine or iodine atom or by a $C_{1-3}$-alkyl group.

The following are mentioned as examples of particularly preferred compounds:

(1) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(3-dimethylamino-propyl)-1H-benzimidazol-2-yl]-ethyl}-amide, (2) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(2-dimethylamino-ethyl)-1H-benzimidazol-2-yl]-ethyl}-amide, (3) 4-(2-oxo-1,2,4,5-tetrahydro-1,3-benzodiazepin-3-yl)-piperidin-1-carboxylic acid-[(R)-2-(4-amino-3,5-dibromo-phenyl)-1-(1-methyl-1H-benzimidazol-2-yl)-ethyl]-amide, (4) 4-(2-oxo-1,2,4,5-tetrahydro-1,3-benzodiazepin-3-yl)-piperidin-1-carboxylic acid-[(R)-2-(4-amino-3,5-dibromo-phenyl)-1-(1H-benzimidazol-2-yl)-ethyl]-amide, (5) methyl 2-((R)-2-(4-amino-3,5-dibromo-phenyl)-1-{[4-(2-oxo-1,4-dihydro-3H-quinazolin-3-yl)-piperidin-1-carbonyl]-amino}-ethyl)-1H-benzimidazolee-5-carboxylate, (6) methyl 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazolee-5-carboxylate, (7) 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acid, (8) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[6-(4-methyl-piperazin-1-carbonyl)-1H-benzimidazol-2-yl]-ethyl}-amide, (9) 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acid-(3-dimethylamino-propyl)-amide,

(10) 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acid-(2-dimethylamino-ethyl)-amide,

(11) 4-(2-oxo-1,4-dihydro-2H-quinazolin-3-yl)-piperidin-1-carboxylic acid-{(R)-2-(4amino-3,5-dibromo-phenyl)-1-[1-(3-dimethylamino-propyl)-5-phenyl-1H-imidazol-2-yl]-ethyl}-amide,

(12) 4-(2-oxo-1,2,4,5-tetrahydro-1,3-benzodiazepin-3-yl)-piperidin-1-carboxylic acid-[(R)-2-(4-amino-3,5-dibromo-phenyl)-1-(1-butyl-1H-benzimidazol-2-yl)-ethyl]-amide,

(13) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(3-pyrrolidin-1-yl-propyl)-1H-benzimidazol-2-yl]-ethyl}-amide,

(14) 4-(2-oxo-1,2,4,5-tetrahydro-1,3-benzodiazepin-3-yl)-piperidin-1-carboxylic acid-[(R)-2-(4-amino-3,5-dibromo-phenyl)-1-(1-pyridin-3-yl methyl-1H-benzimidazol-2-yl)-ethyl]-amide,

(15) 4-(2-oxo-1,2,4,5-tetrahydro-1,3-benzodiazepin-3-yl)-piperidin-1-carboxylic acid-[(R)-2-(4-amino-3,5-dibromo-phenyl)-1-(1-benzyl-1H-benzimidazol-2-yl)-ethyl]-amide,

(16) 4-(2-oxo-1,2,4,5-tetrahydro-1,3-benzodiazepin-3-yl)-piperidin-1-carboxylic acid {(R)-2-(4-amino-3,5-dibromo-phenyl)-1-[1-(1-methyl-piperidin-4-ylmethyl)-1H-benzimidazol-2-yl]-ethyl}-amide,

(17) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(4-dimethylamino-butyl)-1H-benzimidazol-2-yl]-ethyl}-amide,

(18) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(1-methyl-piperidin-4-yl)-1H-benzimidazol-2-yl]-ethyl}-amide,

(19) 4-(2-oxo-1,2,4,5-tetrahydro-1,3-benzodiazepin-3-yl)-piperidin-1-carboxylic acid-[(R)-2-(4-amino-3,5-dibromo-phenyl)-1-(1-cyclohexyl-1H-benzimidazol-2-yl)-ethyl]-amide,

(20) 4-(2-oxo-1,2,4,5-tetrahydro-1,3-benzodiazepin-3-yl)-piperidin-1-carboxylic acid-[(R)-2-(4-amino-3,5-dibromo-phenyl)-1-(1-cyclopentyl-1H-benzimidazol-2-yl)-ethyl]-amide,

(21) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(5-dimethylamino-pentyl)-1H-benzimidazol-2-yl]-ethyl}-amide,

(22) methyl 4-[2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-benzimidazol-1-yl]-butyrate,

(23) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[6-chloro-1-(3-dimethylamino-propyl)-1H-benzimidazol-2-yl]-ethyl}-amide,

(24) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(3-dimethylamino-propyl)-6-fluoro-1H-benzimidazol-2-yl]-ethyl}-amide,

(25) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(3-dimethylamino-propyl)-5-fluoro-1H-benzimidazol-2-yl]-ethyl}-amide,

(26) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[5,6-dichloro-1-(3-dimethylamino-propyl)-1H-benzimidazol-2-yl]-ethyl}-amide,

(27) methyl 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylate,

(28) 2-(2-(4-amino-3-chloro-5-trifluoromethyl-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylic acid,

(29) 4-(2-oxo-1,2,4,5-tetrahydro-1,3-benzodiazepin-3-yl)-piperidin-1-carboxylic acid-{(R)-2-(3,5-dibromo-4-hydroxy-phenyl)-1-[1-(1-methyl-piperidin-4-ylmethyl)-1H-benzimidazol-2-yl]-ethyl}-amide,

(30) 4-(2-oxo-1,2,4,5-tetrahydro-1,3-benzodiazepin-3-yl)-piperidin-1-carboxylic acid-{(R)-2-(3,5-dibromo-4-hydroxy-phenyl)-1-[1-(1-methyl-piperidin-4-yl)-1H-benzimidazol-2-yl]-ethyl}-amide,

(31) 4-(2-oxo-1,2,4,5-tetrahydro-1,3-benzodiazepin-3-yl)-piperidin-1-carboxylic acid-{(R)-2-(3,5-dibromo-4-hydroxy-phenyl)-1-[1-(3-dimethylamino-propyl)-1H-benzimidazol-2-yl]-ethyl}-amide,

(32) 4-(2-oxo-1,2,4,5-tetrahydro-1,3-benzodiazepin-3-yl)-piperidin-1-carboxylic acid-{(R)-2-(3,5-dibromo-4-hydroxy-phenyl)-1-[1-(3-pyrrolidin-1-yl-propyl)-1H-benzimidazol-2-yl]-ethyl}-amide,

(33) 4-(2-oxo-1,2,4,5-tetrahydro-1,3-benzodiazepin-3-yl)-piperidin-1-carboxylic acid-[1-[6-chloro-1-(3-dimethylamino-propyl)-1H-benzimidazol-2-yl]-2-(3,4-dibromo-phenyl)-ethyl]-amide,

(34) 4-(2-oxo-1,2,4,5-tetrahydro-1,3-benzodiazepin-3-yl)-piperidin-1-carboxylic acid-{2-(3,4-dibromo-phenyl)-1-[5,6-dichloro-1-(3-dimethylamino-propyl)-1H-benzimidazol-2-yl]-ethyl}-amide,

(35) 4-(2-oxo-1,2,4,5-tetrahydro-1,3-benzodiazepin-3-yl)-piperidin-1-carboxylic acid-[1-[7-chloro-1-(3-dimethylamino-propyl)-1H-benzimidazol-2-yl]-2-(3,4-dibromo-phenyl)-ethyl]-amide,

(36) 4-(2-oxo-1,2,4,5-tetrahydro-1,3-benzodiazepin-3-yl)-piperidin-1-carboxylic acid-{2-(3,4-dibromo-phenyl)-1-[1-(3-dimethylamino-propyl)-6-fluoro-1H-benzimidazol-2-yl]-ethyl}-amide,

(37) 4-(2-oxo-1,2,4,5-tetrahydro-1,3-benzodiazepin-3-yl)-piperidin-1-carboxylic acid-{2-(3,4-dibromo-phenyl)-1-[1-(1-methyl-piperidin-4-yl)-1H-benzimidazol-2-yl]-ethyl}-amide,

(38) 4-(2-oxo-1,2,4,5-tetrahydro-1,3-benzodiazepin-3-yl)-piperidin-1-carboxylic acid-{2-(3,4-dibromo-phenyl)-1-[1-(3-pyrrolidin-1-yl-propyl)-1H-benzimidazol-2-yl]-ethyl}-amide,

(39) 4-(2-oxo-1,2,4,5-tetrahydro-1,3-benzodiazepin-3-yl)-piperidin-1-carboxylic acid-{2-(3,4-dibromo-phenyl)-1-[1-(1-methyl-piperidin-4-ylmethyl)-1H-benzimidazol-2-yl]-ethyl}-amide,

(40) 4-(2-oxo-1,2,4,5-tetrahydro-1,3-benzodiazepin-3-yl)-piperidin-1-carboxylic acid-[2-(3,4-dibromo-phenyl)-1-(1-pyridin-3-yl methyl-1H-benzimidazol-2-yl)-ethyl]-amide,

(41) 4-(2-oxo-1,2,4,5-tetrahydro-1,3-benzodiazepin-3-yl)-piperidin-1-carboxylic acid-{2-(3,4-dibromo-phenyl)-1-[1-(3-dimethylamino-propyl)-1H-benzimidazol-2-yl]-ethyl}-amide,

(42) 4-(2-oxo-1,2,4,5-tetrahydro-1,3-benzodiazepin-3-yl)-piperidin-1-carboxylic acid-{2-(3,4-dibromo-phenyl)-1-[1-(4-dimethylamino-butyl)-1H-benzimidazol-2-yl]-ethyl}-amide,

(43) 4-(2-oxo-1,2,4,5-tetrahydro-1,3-benzodiazepin-3-yl)-piperidin-1-carboxylic acid-{2-(3,4-diethyl-phenyl)-1-[1-(3-dimethylamino-propyl)-1H-benzimidazol-2-yl]-ethyl}-amide,

(44) 4-(2-oxo-1,2,4,5-tetrahydro-1,3-benzodiazepin-3-yl)-piperidin-1-carboxylic acid-{2-(3,4-diethyl-phenyl)-1-[1-(4-dimethylamino-butyl)-1H-benzimidazol-2-yl]-ethyl}-amide,

(45) 4-(2-oxo-1,2,4,5-tetrahydro-1,3-benzodiazepin-3-yl)-piperidin-1-carboxylic acid-{2-(3,4-diethyl-phenyl)-1-[1-(1-methyl-piperidin-4-yl)-1H-benzimidazol-2-yl]-ethyl}-amide,

(46) 4-(2-oxo-1,2,4,5-tetrahydro-1,3-benzodiazepin-3-yl)-piperidin-1-carboxylic acid-{2-(3,4-diethyl-phenyl)-1-[1-(3-pyrrolidin-1-yl-propyl)-1H-benzimidazol-2-yl]-ethyl}-amide,

(47) 4-(2-oxo-1,2,4,5-tetrahydro-1,3-benzodiazepin-3-yl)-piperidin-1-carboxylic acid-{2-(3,4-diethyl-phenyl)-1-[1-(1-methyl-piperidin-4-ylmethyl)-1H-benzimidazol-2-yl]-ethyl}-amide,

(48) 4-(2-oxo-1,2,4,5-tetrahydro-1,3-benzodiazepin-3-yl)-piperidin-1-carboxylic acid-[2-(3,4-diethyl-phenyl)-1-(1-pyridin-3-ylmethyl-1H-benzimidazol-2-yl)-ethyl]-amide,

(49) 4-(2-oxo-1,2,4,5-tetrahydro-1,3-benzodiazepin-3-yl)-piperidin-1-carboxylic acid-{2-(3,5-bis-trifluoromethyl-phenyl)-1-[1-(1-methyl-piperidin-4-yl)-1H-benzimidazol-2-yl]-ethyl}-amide,

(50) 4-(2-oxo-1,2,4,5-tetrahydro-1,3-benzodiazepin-3-yl)-piperidin-1-carboxylic acid-{2-(3,5-bis-trifluoromethyl-phenyl)-1-[1-(3-pyrrolidin-1-yl-propyl)-1H-benzimidazol-2-yl]-ethyl}-amide,

(51) 4-(2-oxo-1,2,4,5-tetrahydro-1,3-benzodiazepin-3-yl)-piperidin-1-carboxylic acid-{2-(3,5-bis-trifluoromethyl-phenyl)-1-[1-(1-methyl-piperidin-4-ylmethyl)-1H-benzimidazol-2-yl]-ethyl}-amide,

(52) 4-(2-oxo-1,2,4,5-tetrahydro-1,3-benzodiazepin-3-yl)-piperidin-1-carboxylic acid-{2-(3,5-bis-trifluoromethyl-phenyl)-1-[1-(3-dimethylamino-propyl)-1H-benzimidazol-2-yl]-ethyl}-amide,

(53) 2-(2-(4-amino-3-chloro-5-trifluoromethyl-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylate methyl,

(54) 2-(2-(4-amino-3-chloro-5-trifluoromethyl-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylic acid,

(55) 4-(2-oxo-1,2,4,5-tetrahydro-1,3-benzodiazepin-3-yl)-piperidin-1-carboxylic acid-{2-(4-amino-3-chloro-5-trifluoromethyl-phenyl)-1-[1-(1-methyl-piperidin-4-yl)-1H-benzimidazol-2-yl]-ethyl}-amide,

(56) 4-(2-oxo-1,2,4,5-tetrahydro-1,3-benzodiazepin-3-yl)-piperidin-1-carboxylic acid-{2-(4-amino-3-chloro-5-trifluoromethyl-phenyl)-1-[1-(3-pyrrolidin-1-yl-propyl)-1H-benzimidazol-2-yl]-ethyl}-amide,

(57) 4-(2-oxo-1,2,4,5-tetrahydro-1,3-benzodiazepin-3-yl)-piperidin-1-carboxylic acid-{2-(4-amino-3-chloro-5-trifluoromethyl-phenyl)-1-[1-(1-methyl-piperidin-4-ylmethyl)-1H-benzimidazol-2-yl]-ethyl}-amide,

(58) 4-(2-oxo-1,2,4,5-tetrahydro-1,3-benzodiazepin-3-yl)-piperidin-1-carboxylic acid-[2-(4-amino-3-chloro-5-trifluoromethyl-phenyl)-1-(1-pyridin-3-ylmethyl-1H-benzimidazol-2-yl)-ethyl]-amide,

(59) 4-(2-oxo-1,2,4,5-tetrahydro-1,3-benzodiazepin-3-yl)-piperidin-1-carboxylic acid-{2-(4-amino-3-chloro-5-trifluoromethyl-phenyl)-1-[1-(3-dimethylamino-propyl)-1H-benzimidazol-2-yl]-ethyl}-amide,

(60) 3-(1-{4-(3,4-diethyl-phenyl)-3-[1-(3-dimethylamino-propyl)-1H-benzimidazol-2-yl]-butyryl}-piperidin-4-yl)-1,3,4,5-tetrahydro-1,3-benzodiazepin-2-one,

(61) 3-(1-{4-(4-amino-3-chloro-5-trifluoromethyl-phenyl)-3-[1-(3-pyrrolidin-propyl)-1H-benzimidazol-2-yl]-butyryl}-piperidin-4-yl)-1,3,4,5-tetrahydro-1,3-benzodiazepin-2-one,

(62) 3-(1-{4-(4-amino-3-chloro-5-trifluoromethyl-phenyl)-3-[1-(3-imidazol-1-yl-propyl)-1H-benzimidazol-2-yl]-butyryl}-piperidin-4-yl)-1,3,4,5-tetrahydro-1,3-benzodiazepin-2-one,

(63) 3-(1-{4-(4-amino-3-chloro-5-trifluoromethyl-phenyl)-3-[5-(3-dimethylamino-propyl)-1-ethyl-1H-benzimidazol-2-yl]-butyryl}-piperidin-4-yl)-1,3,4,5-tetra-hydro-1,3-benzodiazepin-2-one,

(64) 3-(1-{4-(4-amino-3-chloro-5-trifluoromethyl-phenyl)-3-[1-(3-diethylamino-propyl)-1H-benzimidazol-2-yl]-butyryl}-piperidin-4-yl)-1,3,4,5-tetrahydro-1,3-benzodiazepin-2-one,

(65) 3-(1-{4-(4-amino-3-chloro-5-trifluoromethyl-phenyl)-3-[1-(4-hydroxy-butyl)-1H-benzimidazol-2-yl]-butyryl}-piperidin-4-yl)-1,3,4,5-tetrahydro-1,3-benzodiazepin-2-one,

(66) 3-(1-{4-(4-amino-3-chloro-5-trifluoromethyl-phenyl)-3-[1-(1-methyl-piperidin-3-ylmethyl)-1H-benzimidazol-2-yl]-butyryl}-piperidin-4-yl)-1,3,4,5-tetrahydro-1,3-benzodiazepin-2-one,

(67) 3-[1-(4-(4-amino-3-chloro-5-trifluoromethyl-phenyl)-3-{1-[2(4methyl-piperazin-1-yl)-ethyl]-1H-benzimidazol-2-yl}-butyryl)-piperidin-4-yl]-1,3,4,5-tetrahydro-1,3-benzodiazepin-2-one,

(68) 3-{1-[4-(4-amino-3-chloro-5-trifluoromethyl-phenyl)-3-(1-pyridin-4-ylmethyl-1H-benzimidazol-2-yl)-butyryl]-piperidin-4-yl}-1,3,4,5-tetrahydro-1,3-benzodiazepin-2-one,

(69) 3-{1-[4-(4-amino-3-chloro-5-trifluoromethyl-phenyl)-3-(1-piperidin-4-ylmethyl-1H-benzimidazol-2-yl)-butyryl]-piperidin-4-yl}-1,3,4,5-tetrahydro-1,3-benzodiazepin-2-one,

(70) 3-(1-{4-(4-amino-3-chloro-5-trifluoromethyl-phenyl)-3-[1-(3-dimethylamino-2,2-dimethyl-propyl)-1H-benzimidazol-2-yl]-butyryl}-piperidin-4-yl)-1,3,4,5-tetrahydro-1,3-benzodiazepin-2-one,

(71) 3-(1-{4-(4-amino-3-chloro-5-trifluoromethyl-phenyl)-3-[7-(3-dimethylamino-propoxy)-1H-benzimidazol-2-yl]-butyryl}-piperidin-4-yl)-1,3,4,5-tetrahydro-1,3-benzodiazepin-2-one,

(72) 3-{1-[4-(4-amino-3-chloro-5-trifluoromethyl-phenyl)-3-(1-piperidin-4-ylmethyl-1H-imidazo[4,5-c]pyridin-2-yl)-butyryl]-piperidin-4-yl}-1,3,4,5-tetrahydro-1,3-benzodiazepin-2-one,

(73) 3-(1-{4-(4-amino-3-chloro-5-trifluoromethyl-phenyl)-3-[3-(3-pyrrolidin-1-yl-propyl)-3H-imidazo[4,5-c]pyridin-2-yl]-butyryl}-piperidin-4-yl)-1,3,4,5-tetrahydro-1,3-benzodiazepin-2-one,

(74) 3-{1-[4-(4-amino-3-chloro-5-trifluoromethyl-phenyl)-3-(1-methyl-6-pyrrolidin-1-ylmethyl-1H-benzimidazol-2-yl)-butyryl]-piperidin-4-yl}-1,3,4,5-tetrahydro-1,3-benzodiazepin-2-one,

(75) enantiomer of 3-(1-{4-(4-amino-3-chloro-5-trifluoromethyl-phenyl)-3-[1-(3-diethylamino-propyl)-1H-benzimidazol-2-yl]-butyryl}-piperidin-4-yl)-1,3,4,5-tetrahydro-1,3-benzodiazepin-2-one,

(76) enantiomer of 3-[1-(4-(4-amino-3-chloro-5-trifluoromethyl-phenyl)-3-{1-[2-(4-methyl-piperazin-1-yl)-ethyl]-1H-benzimidazol-2-yl}-butyryl)-piperidin-4-yl]-1,3,4,5-tetrahydro-1,3-benzodiazepin-2-one, their stereoisomers and salts.

The compounds of general formula I are prepared by methods known in principle. The following methods have proved particularly suitable for preparing the compounds of general formula I according to the invention:

a) In order to prepare compounds of general formula I wherein X denotes the oxygen atom and Z denotes the —NR¹ group, and wherein R¹, R³ and R⁴ and A are as hereinbefore defined Reacting amines of general formula II,

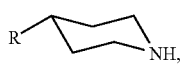

wherein
R is as hereinbefore defined, with carbonic acid derivatives of general formula III,

wherein
X¹ denotes a nucleofugic group, preferably the 1H-imidazol-1-yl, 1H-1,2,4-triazol-1-yl, trichloromethoxy or 2,5-dioxopyrrolidin-1-yloxy group, and with compounds of general formula IV,

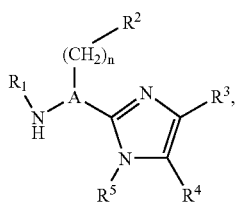

wherein
R¹, R², R³, R⁴, R⁵ and n are as hereinbefore defined, and, if necessary, subsequently cleaving any protecting groups or converting precursor functions by the methods described above.

The reactions which are theoretically two-step reactions are usually carried out as one-pot processes, preferably by reacting one of the two components II or IV with equimolar quantities of the carbonic acid derivative of general formula III in a suitable solvent at lower temperature in the first stage, then adding at least equimolar amounts of the other component IV or II and finishing the reaction at elevated temperature. The reactions with bis-(trichloromethyl)-carbonate are preferably carried out in the presence of at least 2 equivalents (based on bis-(tri-chloromethyl)-carbonate) of a tertiary base, e.g. triethylamine, N-ethyl-diisopropylamine, pyridine, 1,5-diazabicyclo[4,3,0]non-5-ene, 1,4-diazabicyclo-[2,2,2]octane or 1,8-diazabicyclo[5,4,0]undec-7-ene. Examples of solvents, which should be anhydrous, include tetrahydrofuran, dioxane, dimethyl formamide, dimethylacetamide, N-methyl-2-pyrrolidone, 1,3-dimethyl-2-imidazolidinone or acetonitrile; if bis-(trichloromethyl)-carbonate is used as the carbonyl component anhydrous chlorohydrocarbons such as dichloromethane, 1,2-dichloroethane or trichloroethylene are preferred. The reaction temperatures for the first reaction step are between −30 and +25° C., preferably −5 and +10° C., for the second reaction step they are between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Präparativen Organischen Chemie, Vol. V, p. 53-93, Verlag Chemie, Weinheim/Bergstr., 1967; P. Majer and R. S. Randad, J. Org. Chem. 59, 1937-1938 (1994); K. Takeda, Y. Akagi, A. Saiki, T. Sukahara and H. Ogura, Tetrahedron Letters 24 (42), 4569-4572 (1983)).

b) In order to prepare compounds of general formula I wherein R³ and R⁴ together represent a 1,3-butadien-1,4-ylene group wherein one, two or three methyne groups may each be replaced by a nitrogen atom, a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, di-($C_{1-3}$-alkyl)-amino-$C_{2-3}$-alkyl-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or by a 4- to 7-membered cycloalkyleneimino-carbonyl group wherein one or two hydrogen atoms may each be replaced by a $C_{1-3}$-alkyl group and/or in each case the methylene group in the 4 position of a 6- or 7-membered cycloalkyleneimino moiety may be replaced by an oxygen or sulphur atom, by a sulphinyl, sulphonyl, —NH, —N($C_{1-3}$-alkyl) or —N($C_{1-3}$-alkylcarbonyl)-group, and a second hydrogen atom may optionally additionally be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy or trifluoromethoxy group, and anellation of an amide of general formula

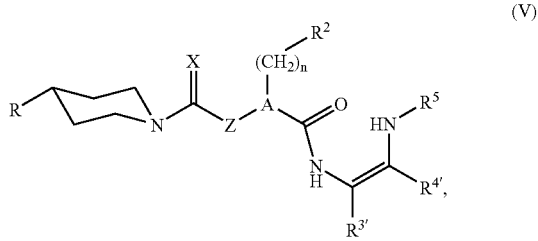

wherein R, X, Z, A, n, R² and R⁵ are as hereinbefore defined, R³' and R⁴' together represent a 1,3-butadien-1,4-ylene group wherein one, two or three methyne groups may each be replaced by a nitrogen atom, a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, di-($C_{1-3}$-alkyl)-amino-$C_{2-3}$-alkyl-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or by a 4- to 7-membered cycloalkyleneiminocarbonyl group wherein one or two hydrogen atoms may each be replaced by a $C_{1-3}$-alkyl group and/or in each case the methylene group in the 4 position of a 6- or 7-membered cycloalkyleneimino moiety may be replaced by an oxygen or sulphur atom, by a sulphinyl, sulphonyl, —NH, —N($C_{1-3}$-alkyl) or —N($C_{1-3}$-alkyl-carbonyl) group, and a second hydrogen atom may optionally additionally be replaced by a fluorine, chlorine or bromine atom, by a $C_{1-3}$-alkyl, trifluoromethyl, difluoromethyl, cyclopropyl, hydroxy, $C_{1-3}$-alkoxy, difluoromethoxy or trifluoromethoxy group, and The reaction is optionally carried out in a solvent or mixture of solvents such as dichloromethane, acetonitrile, dimethylformamide, dimethylsulphoxide, sulpholane, benzene, toluene, chlorobenzene, tetrahydrofuran, benzene/tetrahydrofuran or dioxane conveniently in the presence of an anhydrous acid such as trifluoroacetic acid, methanesulphonic acid, p-toluenesulphonic acid or sulphuric acid or in the presence of a dehydrating agent, e.g. in the presence of isobutyl chloroformate, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, N,N'-carbonyldiimidazole or triphenylphosphine/carbon tetrachloride, at temperatures between −20 and 200° C., but preferably at temperatures between -10 and 160° C.

c) In order to prepare compounds of general formula I wherein X denotes the oxygen atom and Z denotes the —$CH_2$ group:

Coupling a carboxylic acid of general formula

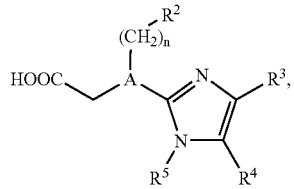

(VI)

wherein
$R^2$ to $R^5$, A and n are as hereinbefore defined,
with a compound of general formula

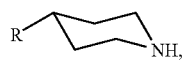

(II)

wherein
R is as hereinbefore defined.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)- N,N-N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) any possible racemisation can additionally be suppressed, if desired, or the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +20° C. If necessary, N-ethyl-diisopropylamine (DIEA) (Hünig base) is preferably used as an additional auxiliary base.

The so-called anhydride process is used as a further coupling method for synthesising compounds of general formula I (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula II which is to be coupled and monoisobutyl carbonate is obtained, using isobutyl chlorocarbonate in the presence of bases such as 4-methyl-morpholine or 4-ethylmorpholine. The preparation of this mixed anhydride and the coupling with amines are carried out in a one-pot process, using the abovementioned solvents and at temperatures between −20 and +25° C., preferably 0 and +25° C.

d) In order to prepare compounds of general formula I wherein X denotes the oxygen atom and Z denotes the —$CH_2$ group:

Coupling a compound of general formula

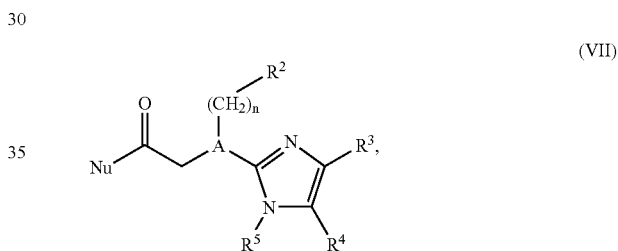

(VII)

wherein
A, n, and $R^2$ to $R^5$ are as hereinbefore defined and Nu denotes a leaving group, for example a halogen atom, such as the chlorine or bromine atom, an alkylsulphonyl-oxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, while the substituents may be identical or different, a 1H-imidazol-1-yl, a 1H-pyrazol-1-yl, 1H-1,2,4-triazol-1-yl, 1H-1,2,3-triazol-1-yl or 1H-1,2,3,4-tetrazol-1-yl group optionally substituted in the carbon skeleton by 1 or 2 methyl groups, a vinyl, propargyl, p-nitrophenyl, 2,4-dinitrophenyl, trichlorophenyl, pentachlorophenyl, pentafluorophenyl, pyranyl or pyridinyl, dimethylaminyloxy, 2(1H)-oxopyridin-1-yloxy, 2,5-dioxopyrrolidin-1-yloxy, phthalimidyloxy, 1H-benzotriazol-1-yloxy or azide group, with a compound of general formula

(II)

wherein
R is as hereinbefore defined.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2] octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

e) In order to prepare compounds of general formula I wherein X denotes the oxygen atom and Z denotes the group —NH—:

Reacting isocyanates of general formula VIII,

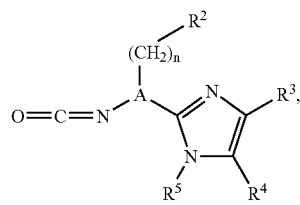

(VIII)

wherein $R^2$ to $R^5$, A and n are as hereinbefore defined with amines of general formula II,

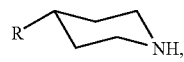

(II)

wherein

R is as hereinbefore defined, and, if necessary, subsequently cleaving protecting groups or treating precursor functions by the methods described above.

The reaction is carried out at temperatures between 0° C. and 150° C., preferably between 20° C. and 100° C., and optionally in the presence of anhydrous solvents, e.g. tetrahydrofuran, 1,4-dioxane, dimethylformamide, dimethylacetamide, N-methyl-2-pyrrolidone or 1,3-dimethyl-2-imidazolidinone or mixtures thereof.

f) In order to prepare compounds of general formula I wherein X denotes one of the groups =N—CN or =N—SO$_2$—R$^6$ and Z denotes the group —NR$^1$—, where R$^1$ and R$^6$ are as hereinbefore defined:

Reacting compounds of general formula

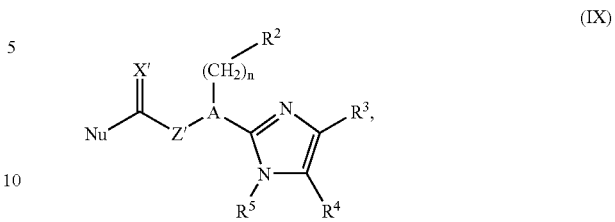

(IX)

wherein A, n and $R^2$ to $R^5$ are as hereinbefore defined, X' denotes one of the groups =N—CN or =N—SO$_2$—R$^6$, Z' denotes the group —NR$^1$, while R$^1$ and R$^6$ are as hereinbefore defined, and Nu is a leaving group, for example an alkoxy, aryloxy, alkylthio, alkylsulphinyl or alkylsulphonyl group each with up to 10 carbon atoms, e.g. the methoxy, ethoxy, phenyloxy, methylthio, ethylthio, methylsulphinyl, ethylsulphinyl, propylsulphinyl, isopropylsulphinyl, methylsulphonyl or ethylsulphonyl group, the chlorine or bromine atom, the SO$_2$H, SO$_3$H or OPOCl$_2$-group, but preferably the phenoxy group, with secondary amines of general formula

(II)

wherein R is as hereinbefore defined.

The reactions are carried out analogously to methods known from the literature (cf. G. B. L. Smith, J. Amer. Chem. Soc. 51, 476 [1929]; B. Rathke, Chem. Ber. 17, 297 [1884]; R. Phillips and H. T. Clarke, J. Amer. Chem. Soc. 45, 1755 [1923]; S. J. Angyal and W. K. Warburton, J. Amer. Chem. Soc. 73, 2492 [1951]; H. Lecher and F. Graf, Chem. Ber. 56, 1326 [1923]; J. Wityak, S. J. Gould, S. J. Hein and D. A. Keszler, J. Org. Chem. 52, 2179 [1987]; T. Teraji, Y. Nakai, G. J. Durant, WO-A-81/00109, Chem. Abstr. 94, 192336z [1981]; C. A. Maryanoff, R. C. Stanzione, J. N. Plampin and J. E. Mills, J. Org. Chem. 51, 1882-1884 [1986]; A. E. Miller and J. J. Bischoff, Synthesis 1986, 777; R. A. B. Bannard, A. A. Casselman, W. F. Cockburn and G. M. Brown, Can. J. Chem. 36, 1541 [1958]; Aktieselskabet Grea, Kopenhagen, DE2826452-C2; K. Kim, Y. T. Lin and H. S. Mosher, Tetrah. Letters 29, 3183-3186 [1988]; H. B. Arzeno et al., Synth. Commun. 20, 3433-3437 [1990]; H. Bredereck and K. Bredereck, Chem. Ber. 94, 2278 [1961]; H. Eilingsfeld, G. Neubauer, M. Seefelder and H. Weidinger, Chem. Ber. 97, 1232 [1964]; P. Pruszynski, Can. J. Chem. 65, 626 [1987]; D. F. Gavin, W. J. Schnabel, E. Kober and M. A. Robinson, J. Org. Chem. 32, 2511 [1967]; N. K. Hart, S. R. Johns, J. A. Lamberton and R. I. Willing, Aust. J. Chem. 23, 1679 [1970]; CIBA Ltd., Belgian Patent 655403; Chem. Abstr. 64, 17481 [1966]; J. P. Greenstein, J. Org. Chem. 2, 480 [1937]; F. L. Scott and J. Reilly, J. Amer. Chem. Soc. 74, 4562 [1952]; W. R. Roush and A. E. Walts, J. Amer. Chem. Soc. 106, 721 [1984]; M. S. Bernatowicz, Y. Wu and G. R. Matsueda, J. Org. Chem. 57, 2497-2502 [1992]; H. Tsunematsu, T. Imamura and S. Makisumi, J. Biochem. 94, 123-128 [1983]; R. Mohr, A. Buschauer and W. Schunack, Arch. Pharm. 321, 221-227 [1988]; K. Atwal, F. N. Ferrara and S. Z. Ahmed, Tetrah. Lett. 35, 8085-8088 [1994]; P. J. Garratt, C. J. Hobbs and R. Wrigglesworth, J. Org. Chem. 54, 1062-1069 [1989]; P. J.

Garratt and S. N. Thorn, Tetrahedron 49, 6885-6898 [1993]) at temperatures between 0° C. and +100° C., preferably +40° C. and +80° C., and using inert solvents, for example dichloromethane, tetrahydrofuran, 1,4-dioxane, acetonitrile, dimethylformamide, 2-pentanol, dimethylacetamide, N-methylpyrrolidone or mixtures thereof and generally in the presence of auxiliary bases, particularly alkali metal carbonates, such as sodium or potassium carbonate, or tertiary amines, preferably N-ethyl-diisopropylamine or triethylamine.

In the reactions described above, any reactive groups present such as hydroxy, carboxy, amino or imino groups may be protected during the reaction by methods known from the literature by conventional protecting groups which are cleaved again after the reaction; the protecting groups conventionally used in peptide chemistry may be used, in particular. Information on this may be found in WO 98/11128 for example.

Alternatively, compounds of type (I) may also be prepared as follows:

separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula (I) is reacted with one of the abovementioned optically active acids or bases in equimolar amounts in a solvent and the resulting crystalline, diastereomeric, optically active salts thereof are separated using their different solubilities. This reaction may

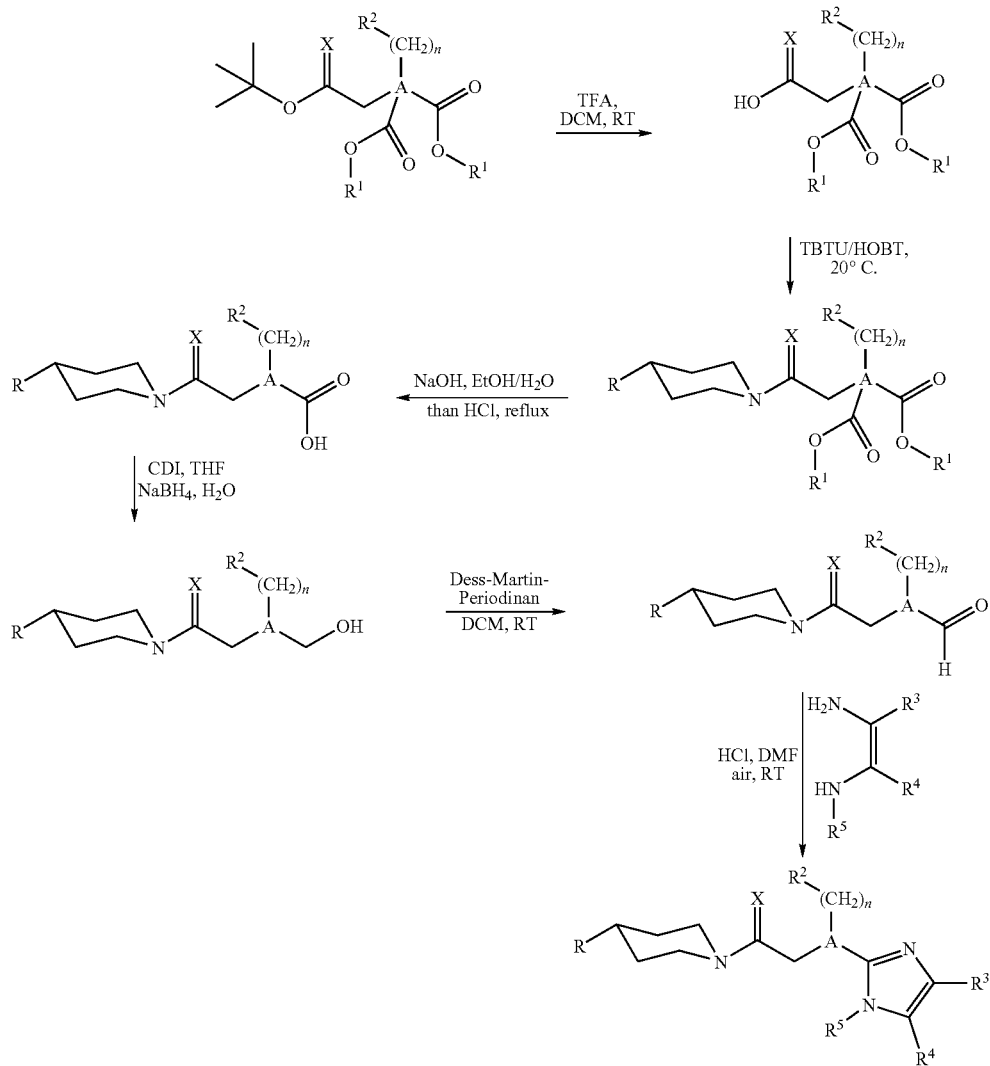

Stereoisomeric compounds of formula (I) may be separated by conventional methods. The diastereomers may be be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, neutralised with a base such as sodium carbonate or potassium carbonate, sodium hydroxide solution or potassium hydroxide solution and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The starting compounds of general formulae II and III are commercially available or are prepared by methods known from the literature. Starting compounds of general formula (II) may be obtained according to the methods described in WO 98/11128, WO 00/55154 and DE 199 52 146.

Isocyanates of general formula VIII may readily be obtained from corresponding α-amino acid derivatives or the hydrochlorides thereof by reacting with phosgene, diphosgene or triphosgene in the presence of pyridine (cf. also: J. S. Nowick, N. A. Powell, T. M. Nguyen and G. Noronha, J. Org. Chem. 57, 7364-7366 [1992]).

Starting compounds of general formula IV are obtained for example according to the following synthesis diagram, in which A denotes a carbon atom substituted by a hydrogen atom or a $C_{1-3}$-alkyl group:

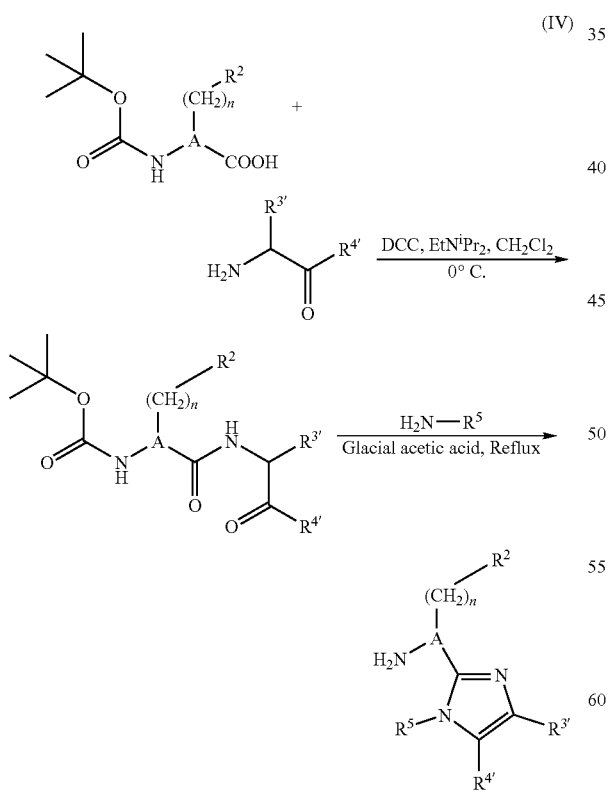

Starting compounds of general formula V are obtained for example according to the following synthesis diagram:

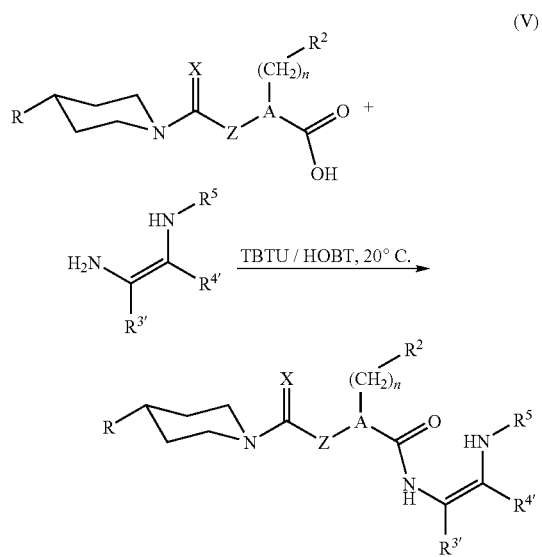

The starting materials required are either described in WO 98/11128 or obtained starting from 1-fluoro-2-nitro-aryl or heteroaryl compounds by reacting with corresponding amines and subsequently reducing the nitro to the amino group.

Compounds of type VI are obtained for example according to the following synthesis diagram, while $R^3$ and $R^4$ together may not form a 1,3-butadien-1,4-ylene group.

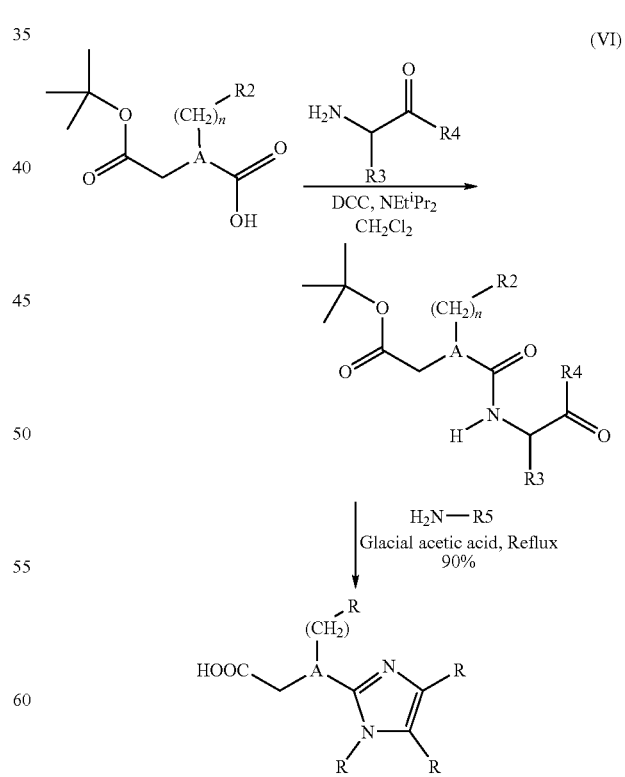

Compounds of type VII are obtained by reactions known from the literature starting from the corresponding carboxylic acids (VI).

Compounds of type IX are obtained for example by reacting the amines of general formula

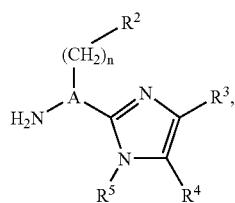

(IX)

wherein A, n, $R^2$ to $R^5$ are as hereinbefore defined with iminocarbonates of general formula Nu-X'-Nu'' wherein X' denotes one of the abovementioned groups =N—CN or =N—$SO_2$—$R^6$, Nu is a leaving group, for example an alkoxy, aryloxy, alkylthio, alkylsulphinyl or alkylsulphonyl group with in each case up to 10 carbon atoms, e.g. the methoxy, ethoxy, phenyloxy, methylthio, methylsulphinyl, methylsulphonyl, the chlorine or bromine atom, the $SO_2H$, $SO_3H$ or $OPOCl_2$— group and Nu'', which may be different from Nu or may also be the same as Nu, may assume the same meanings as Nu.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula (I), if they contain an acid function, for example a carboxy group, may if desired be converted into the addition salts thereof with inorganic or organic bases, particularly for pharmaceutical use into the physiologically acceptable addition salts thereof. Suitable bases for this include, for example, sodium hydroxide, potassium hydroxide, ammonia, cyclohexylamine, dicyclohexylamine, ethanolamine, diethanolamine and triethanolamine.

The new compounds of general formula I and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of compounds of general formula I for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution"[BSS (in mM): NaCl 120, KCl 5.4, NaHCO3 16.2, MgSO4 0.8, NaHPO4 1.0, CaCl2 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl2, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl2, 1 mM EDTA, pH 7.40) and homogenised for 30 seconds with an Ultra-Turrax. 230 μl of the homogenised product are incubated for 180 minutes at ambient temperature with 50 pM 1251-iodotyrosyl-Calcitonin-Gene-Related Peptide (Amersham) and increasing concentrations of the test substances in a total volume of 250 μl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 μM human CGRP-alpha during incubation.

The concentration binding curves are analysed using computer-aided non-linear curve matching.

The compounds of general formula I show IC50 values≦10000 nM in the test described.

B. CGRP Antagonism in SK-N-MC Cells

SK-N-MC cells (1 million cells) are washed twice with 250 μl incubation buffer (Hanks' HEPES, 1 mM 3-isobutyl-1-methylxanthine, 1% BSA, pH 7.4) and pre-incubated at 37° C. for 15 minutes. After the addition of CGRP (10 μl) as agonist in increasing concentrations (10-11 to 10-6 M), or additionally the substance in 3 to 4 different concentrations, the mixture is incubated for another 15 minutes.

Intracellular cAMP is then extracted by the addition of 20 μl of 1 M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA2 values of antagonistically acting substances are determined graphically.

The compounds of general formula I exhibit CGRP-antagonistic properties in the in vitro test model described, in a dosage range of between $10^{-11}$ to $10^{-5}$ M.

In view of their pharmacological properties the compounds of general formula I and the salts thereof with physiologically acceptable acids or bases are thus suitable for the acute and prophylactic treatment of headaches, particularly migraine or cluster headaches. Moreover, the compounds of general formula I also have a positive effect on the following diseases: complex regional pain syndrome, non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and consequent reduced circulation of blood through the tissues, e.g. shock and sepsis. In addition, the compounds according to the invention have a general pain-relieving effect. The symptoms of menopausal hot flushes caused by vasodilatation and increased blood flow in oestrogen-deficient women and hormone-treated patients with prostate carcinoma are favourably affected by the CGRP-antagonists of the present application in a preventive and acute-therapeutic capacity, this therapeutic approach being distinguished from hormone replacement by the absence of side effects.

The dosage required to achieve a corresponding effect is conveniently 0.0001 to 3 mg/kg of body weight, preferably 0.01 to 1 mg/kg of body weight, when administered intravenously or subcutaneously and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone substitution, it is advisable to reduce the doses specified above, in which case the dosage may be from ⅕ of the lower limits mentioned above up to 1/1 of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. antiemetics, prokinetics, neuroleptics, antidepressants, neurokinine antagonists, anticonvulsants, histamine-H1 receptor antagonists, antimuscarinics, β-blockers, α-agonists and α-antagonists, ergot alkaloids, mild analgesics, non-steroidal antiinflammatories, corticosteroids, calcium antagonists, 5-$HT_{1B/1D}$ agonists or other anti-migraine agents, which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the nonsteroidal antiinflammatories acclofenac, acemetacin, acetylsalicylic acid, azathioprin, diclofenac, diflunisal, fenbufen, fenoprofen, flurbiprofen, ibuprofen, indometacin, ketoprofen, feflunomid, lornoxicam, mefenaminic acid, naproxen, phenylbutazone, piroxicam, sulphasalazin, zomepirac or the pharmaceutically acceptable salts thereof as well as meloxicam and other selective COX2-inhibitors, such as for example rofecoxib and celecoxib.

It is also possible to use ergotamine, dihydroergotamine, metoclopramide, domperidone, diphenhydramine, cyclizine, promethazine, chlorpromazine, vigabatrin, timolol, isomethepten, pizotifen, botox, gabapentin, topiramat, riboflavin, montelukast, lisinopril, prochloroperazine, dexamethasone, flunarizine, dextropropoxyphene, meperidine, metoprolol, propranolol, nadolol, atenolol, clonidine, indoramine, carbamazepine, phenytoin, valproate, amitryptilin, lidocaine or diltiazem and other 5-$HT_{1B/1D}$-agonists such as, for example, almotriptan, avitriptan, eletriptan, frovatriptan, naratriptan, rizatriptan, sumatriptan and zolmitriptan.

The dosage of these active substances is expediently ⅕ of the lowest recommended dose to 1/1 of the normally recommended dose, i.e. for example 20 to 100 mg of sumatriptan.

The invention further relates to the use of the compounds of general formula I as valuable adjuvants for the production and purification (by affinity chromatography) of antibodies as well as in RIA and ELISA assays, after suitable radioactive labelling, for example by direct labelling with $^{125}I$ or $^{131}I$ or by tritiation of suitable precursors, for example by replacing halogen atoms with tritium, and as a diagnostic or analytical adjuvant in neurotransmitter research.

The Examples which follow are intended to illustrate the invention:

Preliminary Remarks:

As a rule, melting points, IR, UV, $^1$H-NMR and/or mass spectra have been obtained for the compounds prepared. Unless otherwise stated, Rf values were obtained using ready-made silica gel TLC plates 60 $F_{254}$ (E. Merck, Darmstadt, Item no. 1.05714) without chamber saturation. The $R_f$ values obtained under the name Alox were obtained using ready-made aluminium oxide 60 $F_{254}$ TLC plates (E. Merck, Darmstadt, item no. 1.05713) without chamber saturation. The ratios given for the eluants relate to units by volume of the solvent in question. For chromatographic purification, silica gel made by Millipore (MATREX™, 35-70 my) was used. If no detailed information is given as to the configuration, it is not clear whether it is a pure enantiomer or whether partial or even complete racemisation has occurred.

The following abbreviations are used in the description of the experiments:

abs. absolute
Alox aluminium oxide (neutral or basic)
Boc tert.-butoxycarbonyl
CDI N,N'-carbonyldiimidazole
CDT N,N'-carbonylditriazole
DMF N,N-dimethylformamide
ether diethyl ether
EtOAc ethyl acetate
EtOH ethanol
sat. saturated
semiconc. semiconcentrated
HCl hydrochloric acid
HOAc acetic acid
HOBt 1-hydroxybenzotriazole-hydrate
Hönig base N,N-diisopropyl-ethylamine
i. vac. in vacuo (in a vacuum)
KOH potassium hydroxide
conc. concentrated
MeOH methanol
MTBE methyl-tert.-butylether
NaCl sodium chloride
NaOH sodium hydroxide
org. organic
RT ambient temperature
TBTU 2-(1H-benzotriazol-1-yl)-1,1,3,3-tetramethyluronium-tetrafluoroborate
TFA trifluoroacetic acid
THF tetrahydrofuran The compounds are named in accordance with English nomenclature. For example "4-(2-oxo-1,2,4,5-tetrahydro-1,3-benzodiazepin-3-yl)-piperidin-1-carboxylic acid-{(R)-2-(4-amino-3,5-dibromo-phenyl)-1-[1-(3-dimethylamino-propyl)-1H-benzimidazol-2-yl]-ethyl}-amide" denotes the compound of the following formula:

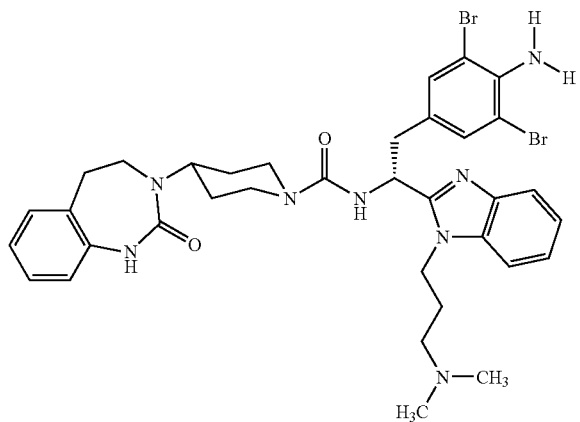

Preparation of intermediate compounds

Intermediate Product 1

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[2-(3-dimethylamino-propylamino)-phenylcarbamoyl]-ethyl}-amide 4.8 mL propanephosphonic acid cycloanhydride was added to an ice-cooled suspension of 1.0 g (1.64 mmol) (R)-3-(4-amino-3,5-dibromo-phenyl)-2-{[4-(2-oxo-1,2,4,5-tetrahydro-benzo[d][1,3]diazepin-3-yl)-piperidin-1-carbonyl]-amino}-propionic acid, 0.305 g (1.70 mmol) N-(3-dimethylamino-propyl)-phenyl-1,2-diamine and 0.9 mL (8.1 mmol) N-methylmorpholine in 50 mL dichloromethane with stirring. The solution was then stirred for 2 hours at 0° C. and 16 hours at RT. The solvent was evaporated i. vac. and the product formed (1.0 g; Yield: 78% of theory) was further reacted in its crude state.

Intermediate Product 2

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[2-(2-dimethylamino-ethylamino)-phenylcarbamoyl]-ethyl}-amide The intermediate product was obtained analogously to intermediate product 1 starting from (R)-3-(4-amino-3,5-dibromo-phenyl)-2-{[4-(2-oxo-1,2,4,5-tetrahydro-benzo[d][1,3]diazepin-3-yl)-piperidin-1-carbonyl]-amino}-propionic acid and N-(2-dimethylamino-ethyl)-benzene-1,2-diamine.

Intermediate Product 3

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(2-methylamino-phenylcarbamoyl)-ethyl]-amide The intermediate product was obtained analogously to intermediate product 1 starting from (R)-3-(4-amino-3,5-dibromo-phenyl)-2-{[4-(2-oxo-1,2,4,5-tetrahydro-benzo[d][1,3]diazepin-3-yl)-piperidin-1-carbonyl]-amino}-propionic acid and N-methyl-benzene-1,2-diamine.

Intermediate Product 4

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(2-amino-phenylcarbamoyl)-ethyl]-amide The intermediate product was obtained analogously to intermediate product 1 starting from (R)-3-(4-amino-3,5-dibromo-phenyl)-2-{[4-(2-oxo-1,2,4,5-tetrahydro-benzo[d][1,3]diazepin-3-yl)-piperidin-1-carbonyl]-amino}-propionic acid and benzene-1,2-diamine.

Intermediate Product 5

Methyl 4-amino-3-((R)-3-(4-amino-3,5-dibromo-phenyl)-2-{[4-(2-oxo-1,4-dihydro-2H-quinazolin-3-yl)-piperidin-1-carbonyl]-amino}-propionylamino)-benzoate The intermediate product was obtained analogously to intermediate product 1 starting from (R)-3-(4-amino-3,5-dibromo-phenyl)-2-{[4-(2-oxo-1,4-dihydro-2H-quinazolin-3-yl)-piperidin-1-carbonyl]-amino}-propionic acid and methyl 3,4-diamino-benzoate.

Intermediate Product 6

Methyl-4-amino-3-((R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionylamino)-benzoate The intermediate product was obtained analogously to intermediate product 1 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and methyl 3,4-diaminobenzoate.

Intermediate Product 7

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(2-butylamino-phenylcarbamoyl)-ethyl]-amide The intermediate product was obtained analogously to intermediate product 1 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and N-butyl-benzene-1,2-diamine.

Intermediate Product 8

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[2-(3-pyrrolidin-1-yl-propylamino)-phenylcarbamoyl]-ethyl}-amide The intermediate product was obtained analogously to intermediate product 1 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and N-(3-pyrrolidin-1-yl-propyl)-benzene-1,2-diamine (Intermediate product 15).

Intermediate Product 9

4-(2-Oxo-1,2,4,5-tetrahydro-1,3-benzodiazepin-3-yl)-piperidin-1-carboxylic acid-((R)-2-(4-amino-3,5-dibromo-phenyl)-1-{2-[(pyridin-3-ylmethyl)-amino]-phenylcarbamoyl}-ethyl)-amide The intermediate product was obtained analogously to intermediate product 1 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and N-pyridin-3-ylmethyl-benzene-1,2-diamine (Intermediate product 16).

Intermediate Product 10

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(2-benzylamino-phenylcarbamoyl)-ethyl]-amide The intermediate product was obtained analogously to intermediate product 1 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and N-benzyl-benzene-1,2-diamine.

Intermediate Product 11

4-(2-Oxo-1,2,4,5-tetrahydro-1,3-benzodiazepin-3-yl)-piperidin-1-carboxylic acid-((R)-2-(4-amino-3,5-dibromo-phenyl)-1-{2-[(1-methyl-piperidin-4-ylmethyl)-amino]-phenylcarbamoyl}-ethyl)-amide The intermediate product was obtained analogously to intermediate product 1 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and N-(1-methyl-piperidin-4-ylmethyl)-benzene-1,2-diamine (Intermediate product 17).

Intermediate Product 12 tert. Butyl [(R)-2-(4-amino-3,5-dibromo-phenyl)-1-(2-oxo-2-phenyl-ethylcarbamoyl)-ethyl]-carbaminate 0.92 g (4.8 mmol) 1-(3-dimethylaminpropyl)-3-ethylcarbodiimid-hydrochloride and 0.822 mL (4.8 mmol) Hönig base were added to an ice-cooled mixture of 1.752 g (4.0 mmol) (R)-3-(4-amino-3,5-dibromo-phenyl)-2-tert.-butoxycarbonylamino-propionic acid, 0.8 g (4.7 mmol) 2-amino-1-phenyl-ethanone-hydrochloride and 50 mL dichloromethane. The reaction mixture was stirred for 1 week at RT, combined with sat. aqueous sodium bicarbonate solution and repeatedly extracted with dichloromethane. The combined organic extracts were washed with water, sat. aqueous NaCl solution and dried over magnesium sulphate. After evaporation of the solvent 2.35 g of a solid was obtained which was purified by column chromatography on silica gel using petroleum ether/EtOAc. 0.54 g (24% of theory) pale yellow crystals were obtained.

ESI-MS: $(M-H)^-=552/554/556$ $(Br_2)$

Intermediate Product 13 tert. Butyl {(R)-2-(4-amino-3,5-dibromo-phenyl)-1-[1-(3-dimethylamino-propyl)-5-phenyl-1H-imidazol-2-yl]-ethyl}-carbaminate A mixture of 3.37 g (6.1 mmol) tert. butyl [(R)-2-(4-amino-3,5-dibromo-phenyl)-1-(2-oxo-2-phenyl-ethylcarbamoyl)-ethyl]-carbaminate (Intermediate product 12), 2.17 g (21.2 mmol) 3-dimethylamino-1-propylamine and 35 mL xylene was combined with 3.5 mL (61.2 mmol) HOAc and refluxed for 50 minutes using a water separator. After the addition of a further 2.17 g (21.2 mmol) 3-dimethylamino-1-propylamine and 3.5 mL (61.2 mmol) HOAc the mixture was refluxed for a further 50 minutes using the water separator and the reaction mixture was combined with EtOAc and 30 mL sat. aqueous sodium carbonate solution. The organic phase was separated off, washed with sat. aqueous NaCl solution, dried over magnesium sulphate and concentrated by evaporation i. vac. The residue was purified by column chromatography on silica gel using petroleum ether/EtOAc (1/1 v/v) and dichloromethane/MeOH (9/1 v/v). 0.54 g (14% of theory) of the desired product was obtained.

ESI-MS: $(M-H)^-=619/621/623$ $(Br_2)$

Intermediate Product 14

Methyl 3-((R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionylamino)-4-(3-pyrrolidin-1-yl-propylamino)-benzoate To a solution of 800 mg (1.313 mmol) (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acidin 70 mL DMF was added at RT 450 mg (1.401 mmol) TBTU and 0.245 mL (1.406 mmol) Honig base and the mixture was stirred for 30 minutes at RT. 370 mg (1.334 mmol) methyl 3-amino-4-(3-pyrrolidin-1-yl-propylamino)-benzoate (Intermediate product 26) was added and the mixture was stirred for 16 hours at RT. The solvent was evaporated i. vac., the residue was combined with 15% aqueous potassium carbonate solution. The precipitate formed was filtered off and dried i. vac.

Yield: 1.10 g (96% of theory) $R_f=0.22$ (silica gel, dichloromethane/MeOH/cyclohexane/conc. aqueous ammonia 70/15/15/2 v/v/v/v) ESI-MS: $(M-H)^-=867/869/871$ $(Br_2)$

Intermediate Products 15

N-(3-Pyrrolidin-1-yl-propyl)-benzene-1,2-diamine

To a solution of 3.700 g (28.857 mmol) 3-pyrrolidin-1-yl-propylamine and 4.000 g (28.941 mmol) potassium carbonate in 20 mL DMF, 1-fluoro-2-nitro-benzene was added dropwise and the mixture was stirred for 16 hours at RT. The reaction mixture was filtered through basic Alox and evaporated i. vac. The residue was dissolved in EtOAc, the org. phase was washed with water, dried over sodium sulphate and evaporated i. vac. The crude product was used in the next reaction step without any further purification (7.080 g, quantitative yield).

The crude product was added to a suspension of 0.700 g Pd/C (10%) in 50 mL THF and the mixture was hydrogenated at 50° C. and 3 bar $H_2$-press.ure for 1.5 hours. The catalyst was removed by filtration and the filtrate evaporated i. vac. and stored under argon at −20° C.

Yield: 6.08 g (99% of theory) $R_f=0.68$ (silica gel, petroleum ether/EtOAc 4/1 v/v) ESI-MS: $(M+H)^+=250$

Intermediate Product 16

N-Pyridin-3-ylmethyl-benzene-1,2-diamine

The product was obtained analogously to intermediate product 15 starting from C-pyridin-3-yl-methylamine and 1-fluoro-2-nitro-benzene. The hydrogenation was carried out with Raney nickel at 50° C. and 3 bar $H_2$-pressure in 4 hours.

Yield: 71% of theory ESI-MS: $(M+H)^+=200$

Intermediate Product 17

N-(1-Methyl-piperidin-4-ylmethyl)-benzene-1,2-diamine

The product was obtained analogously to intermediate product 15 starting from C-(1-methyl-piperidin-4-yl)-methylamine and 1-fluoro-2-nitro-benzene.

Yield: 86% of theory $R_f=0.09$ (Alox, dichloromethane/MeOH/conc. aqueous ammonia 90/10/1 v/v/v) ESI-MS: $(M+H)^+=220$

Intermediate Product 18

N-(4-Dimethylamino-butyl)-benzene-1,2-diamine

The product was obtained analogously to intermediate product 15 starting from N-(4-dimethylamino-butyl)-benzene-1,2-diamine and 1-fluoro-2-nitro-benzene.

Yield: 97% of theory $R_f=0.09$ (silica gel, dichloromethane/MeOH/conc. aqueous ammonia 90/10/1 v/v/v) ESI-MS: $(M+H)^+=208$

Intermediate Product 19

N-(1-Methyl-piperidin-4-yl)-benzene-1,2-diamine

The product was obtained analogously to intermediate product 15 starting from 1-methyl-piperidin-4-ylamine and 1-fluoro-2-nitro-benzene.

Yield: 96% of theory $R_f=0.08$ (silica gel, dichloromethane/MeOH/conc. aqueous ammonia 90/10/1 v/v/v) ESI-MS: $(M+H)^+=206$

Intermediate Product 20

N-(5-Dimethylamino-pentyl)-benzene-1,2-diamine

The product was obtained analogously to intermediate product 15 starting from N-(4-dimethylamino-pentyl)-benzene-1,2-diamine and 1-fluoro-2-nitro-benzene.

Yield: 97% of theory $R_f$=0.05 (silica gel, dichloromethane/MeOH/conc. aqueous ammonia 90/10/1 v/v/v) ESI-MS: $(M+H)^+$=222

Intermediate Product 21

Methyl-4-(2-amino-phenylamino)-butyrate

The product was obtained analogously to intermediate product 15 starting from methyl-4-aminobutyrate -hydrochloride and 1-fluoro-2-nitro-benzene. Yield: 80% of theory $R_f$=0.74 (silica gel, dichloromethane/MeOH/conc. aqueous ammonia 90/10/1 v/v/v) ESI-MS: $(M+H)^+$=209

Intermediate Product 22

4-Chloro-$N^2$-(3-dimethylamino-propyl)-benzene-1,2-diamine

To a solution of 3.500 mL (27.814 mmol) $N^1,N^1$-dimethyl-propane-1,3-diamine and 4.000 g (28.941 mmol) potassium carbonate in 40 mL DMF was added 4.800 g (27.343 mmol) 2,5-difluoro-1-nitro-benzene and the mixture was stirred for 16 hours at RT. The reaction mixture was filtered through basic Alox and evaporated down i. vac. The residue was dissolved in EtOAc, the org. phase washed with water, dried over sodium sulphate and evaporated i. vac. The crude product was used in the next reaction step without any further purification (6.900 g, 98% of theory).

The crude product was added to a suspension of 0.700 g Raney nickel in 50 mL THF and the mixture was hydrogenated at 50° C. and 50 psi $H_2$-pressure for 2 hours. The catalyst was filtered off and the filtrate evaporated down i. vac. and stored under argon at −20° C.

Yield: quantitative $R_f$=0.25 (silica gel, dichloromethane/MeOH/conc. aqueous ammonia 90/10/1 v/v/v) $R_f$=0.13 (silica gel, dichloromethane/MeOH/conc. aqueous ammonia 90/10/1 v/v/v) ESI-MS: $(M+H)^+$=212 (Cl)

Intermediate Product 24

$N^1$-(3-Dimethylamino-propyl)-4-fluoro-benzene-1,2-diamine The product was obtained analogously to intermediate product 22 starting from $N^1,N^1$-dimethyl-propane-1,3-diamine and 2,5-difluoro-1-nitro-benzene.

Yield: 97% of theory $R_f$=0.13 (silica gel, dichloromethane/MeOH/conc. aqueous ammonia 90/10/1 v/v/v) ESI-MS: $(M+H)^+$=212

Intermediate Product 25

4,5-Dichloro-N-(3-dimethylamino-propyl)-benzene-1,2-diamine

The product was obtained analogously to intermediate product 22 starting from $N^1,N^1$-dimethyl-propane-1,3-diamine and 4,5-dichloro-2-fluoro-phenylamine.

Yield: quantitative $R_f$=0.21 (silica gel, dichloromethane/MeOH/conc. aqueous ammonia 90/10/1 v/v/v) ESI-MS: $(M+H)^+$=262/264/266 ($Cl_2$)

Intermediate Product 26

Methyl-3-amino-4-(3-pyrrolidin-1-yl-propylamino)-benzoate

The product was obtained analogously to intermediate product 22 starting from 3-pyrrolidin-1-yl-propylamine and methyl-4-fluoro-3-nitro-benzoate.

Yield: 79% of theory $R_f$=0.21 (silica gel, dichloromethane/MeOH/conc. aqueous ammonia 90/10 /1 v/v/v) ESI-MS: $(M+H)^+$=278

Intermediate Product 27

3-Chloro-$N^2$-(3-dimethylamino-propyl)-benzene-1,2-diamine

The product was obtained analogously to intermediate product 22 starting from $N^1,N^1$-dimethyl-propane-1,3-diamine and 1-chloro-2-fluoro-3-nitro-benzene.

Yield: 98% of theory $R_f$=0.29 (silica gel, dichloromethane/MeOH/conc. aqueous ammonia 90/10/1 v/v/v) ESI-MS: $(M+H)^+$=228/230 (Cl)

Intermediate Product 28

N-(3-lmidazol-1-yl-propyl)-benzene-1,2-diamine-trihydrochloride

The product was obtained analogously to intermediate product 22 starting from 3-imidazol-1-yl-propylamine and 1-fluoro-2-nitro-benzene and after the addition of 20 mL of 5 M HCl in isopropanol isolated as the trihydrochloride salt.

Yield: 98% of theory ESI-MS: $(M+H)^+$=217

Intermediate Product 29

4-(3-Dimethylamino-propyl)-$N^1$-ethyl-benzene-1,2-diamine

To a solution of 2.500 g (9.912 mmol) 3-(4-acetylamino-3-nitro-phenyl)-propionic acid and 3.400 g (10.589 mmol) TBTU in 50 mL THF was added 4.40 mL (25.007 mmol) Hünig base and the mixture was stirred for 30 minutes at RT. 1.000 g (12.263 mmol) dimethylamine-hydrochloride was added and the mixture was stirred for a further 16 hours at RT. The reaction mixture was evaporated i. vac., the residue combined with 15% aqueous potassium carbonate solution and exhaustively extracted with dichloromethane. The combined org. phases were dried over sodium sulphate and evaporated i. vac. The crude product was purified by column chromatography (silica gel, dichloromethane/MeOH/conc. aqueous ammonia 90/10/3 v/v/v) (2.600 g, 94% of theory). The intermediate product was dissolved in 50 mL THF, 10.00 mL (78.821 mmol) trichlorosilane was added dropwise at RT and the suspension was stirred for 30 minutes. 1.400 g (61.009 mmol) lithium borohydride was added batchwise and the mixture was stirred for 1 hour at RT and refluxed for 2 hours. 10 mL semiconc. HCl in 40 mL water was slowly added dropwise and the mixture was refluxed for another hour. The mixture was left to stand for 16 hours, combined with EtOAc and stirred vigorously. The org. phase was separated off, the aqueous phase was made basic with conc. aqueous ammonia and exhaustively extracted with EtOAc. The combined org. extracts were dried over magnesium sulphate and evaporated i. vac. The residue was purified by column chromatography (silica gel, dichloromethane/MeOH/conc. aqueous ammonia 90/10/3 v/v/v).

Yield: 0.350 g (16% of theory) $R_f$=0.49 (silica gel, dichloromethane/cyclohexane/MeOH/conc. aqueous ammonia 70/15/15/1 v/v/v/v) EI-MS: M+=221

Intermediate Product 30

4-(2-Amino-phenylamino)-butan-1-ol

The product was obtained analogously to intermediate product 22 starting from 4-amino-butanol and 1-fluoro-2-nitro-benzene and after the addition of 20 mL of 5 M HCl in isopropanol, isolated as the dihydrochloride salt.

Yield: 73% of theory $R_f$=0.49 (silica gel, dichloromethane/MeOH 50/1 v/v) ESI-MS: $(M+H)^+$=211

Intermediate Product 31

N-(1-Methyl-piperidin-3-ylmethyl)-benzene-1,2-diamine

The product was obtained analogously to intermediate product 22 starting from C-(1-methyl-piperidin-3-yl)-methylamine and 1-fluoro-2-nitro-benzene and after the addition of 3 mL of 5 M HCl in isopropanol isolated as the trihydrochloride salt.

Yield: 19% of theory $R_f$=0.70 (Alox, dichloromethane/MeOH 50/1 v/v) ESI-MS: $(M+H)^+$=220

Intermediate Product 32

N-[2-(4-Methyl-piperazin-1-yl)-ethyl]-benzene-1,2-diamine

The product was obtained analogously to intermediate product 22 starting from 2-(4-methyl-piperazin-1-yl)-ethylamine and 1-fluoro-2-nitro-benzene and after the addition of 15 mL of 5 M HCl in isopropanol isolated as the trihydrochloride salt.

Yield: 72% of theory ESI-MS: $(M+H)^+$=235

Intermediate Product 33

N-Pyridin-4-ylmethyl-benzene-1,2-diamine 4.000 g (24.380 mmol) 4-chloromethyl-pyridine-hydrochloride and 8.000 g (44.180 mmol) benzene-1,2-diamine was added at RT to a suspension of 7.000 g (50.650 mmol) potassium carbonate in 80 mL DMF and the mixture was stirred for 48 hours at RT. The reaction mixture was evaporated i. vac., 100 mL water was added and the resulting mixture was exhaustively extracted with EtOAc. The combined org. phases were dried over sodium sulphate and evaporated down i. vac. The crude product was purified by column chromatography (silica gel, Gradient EtOAc/MeOH 10:0→10:1 v/v). The product was isolated as the trihydrochloride salt by dissolving in MeOH, adding 4 mL of 5 M HCl in isopropanol and drying i. vac.

Yield: 2.320 g (31% of theory) ESI-MS: $(M+H)^+$=200

Intermediate Product 34 tert. Butyl-4-[(2-amino-phenylamino)-methyl]-piperidin-1-carboxylate

The product was obtained analogously to intermediate product 22 starting from tert. butyl-4-aminomethyl-piperidin-1-carboxylate and 1-fluoro-2-nitro-benzene.

Yield: 88% of theory $R_f$=0.51 (Alox, petroleum ether/EtOAc 1/1 v/v) ESI-MS: $(M+H)^+$=306

Intermediate Product 35

3-{1-[4-(4-Amino-3-chloro-5-trifluoromethyl-phenyl)-3-hydroxymethyl-butyryl]-piperidin-4-yl}-1,3,4,5-tetrahydro-1,3-benzodiazepin-2-one To a solution of 3.00 g (5.425 mmol) 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyric acid (intermediate product 68) in 100 mL THF was added 1.054 g (6.500 mmol) CDI and the mixture was stirred for 2 hours at RT. This solution was added dropwise under a nitrogen atmosphere over 5 minutes to an ice-cooled solution of 0.728 g (19.250 mmol) sodium borohydride in 50 mL water and the mixture was stirred for 16 hours at RT. The reaction mixture was acidified with 1 N aqueous HCl to pH 2 and exhaustively extracted with EtOAc. The combined org. phases were washed with sat. aqueous NaCl solution, dried over sodium sulphate and evaporated i. vac.

Yield: 2.900 g (quantitative) ESI-MS: $(M+H)^+$=539/541 (Cl).

Intermediate Product 36

2-(4-Amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde To a solution of 0.539 g (1.000 mmol) 3-{1-[4-(4-amino-3-chloro-5-trifluoromethyl-phenyl)-3-hydroxymethyl-butyryl]-piperidin-4-yl}1,3,4,5-tetrahydro-1,3-benzodiazepin-2-one (Intermediate product 35) in 10 mL dichloromethane was added 0.933 g (2.200 mmol) Dess-Martin-Periodinane and the mixture was stirred for 3 hours at RT. The reaction mixture was washed with sat. aqueous sodium thiosulphate solution and sat. aqueous NaCl solution, dried over sodium sulphate and evaporated down i. vac. The crude product was purified by column chromatography (silica gel, gradient dichloromethane/MeOH 50:1→25:1 v/v).

Yield: 0.320 g (60% of theory) ESI-MS: $(M+H)^+$=537/539 (Cl).

Intermediate Product 37

Dimethylamino-2,2-dimethyl-propyl)-benzene-1,2-diamine

The product was obtained analogously to intermediate product 22 starting from 2,2,$N^1$,$N^1$-tetramethyl-propan-1,3-diamine and 1-fluoro-2-nitro-benzene and after the addition of 25 mL of 5 M HCl in isopropanol isolated as the trihydrochloride salt.

Yield: 89% of theory ESI-MS: $(M+H)^+$=222

Intermediate Product 38

3-(3-Dimethylamino-propoxy)-benzene-1,2-diamine

The product was obtained analogously to intermediate product 22 starting from (3-chloro-propyl)-dimethyl-amine and 2-amino-3-nitro-phenol and after the addition of 5 mL of 5 M HCl in isopropanol isolated as the trihydrochloride salt.

Yield: 74% of theory ESI-MS: $(M+H)^+$=210

Intermediate Product 39

N-(3-Diethylamino-propyl)-benzene-1,2-diamine

The product was obtained analogously to intermediate product 22 starting from $N^1$,$N^1$-diethyl-propane-1,3-diamine and 1-fluoro-2-nitro-benzene and after the addition of 28 mL of 5 M HCl in isopropanol isolated as the trihydrochloride salt.

Yield: 96% of theory ESI-MS: $(M+H)^+$=222

Intermediate Product 40 tert. Butyl-4-[(3-amino-pyridin-4-ylamino)-methyl]-piperidin-1-carboxylate

A solution of 643 mg (3.00 mmol) tert. butyl-4-aminomethyl-piperidin-1-carboxylate and 471 mg (3.00 mmol) 4-methoxy-3-nitro-pyridine in 5 mL MeOH was refluxed for 2 hours and then evaporated down i. vac. The crude product was purified by column chromatography (silica gel, gradient dichloromethane/MeOH 100:0→19:1 v/v) (Yield: 1.010 g, quantitative).

The intermediate product was added to a suspension of 500 mg Raney nickel in 30 mL MeOH and the mixture was hydrogenated for 6 hours at 50° C. and 50 psi $H_2$-pressure. The catalyst was filtered off and the filtrate evaporated i. vac. The crude product was purified by column chromatography (Alox (neutral, activity II-III), Gradient dichloromethane/MeOH 99:1→19:1 v/v) purified.

Yield: 0.480 g (53% of theory) $R_f$=0.15 (silica gel, dichloromethane/MeOH 19/1 v/v) ESI-MS: $(M+H)^+$=307

Intermediate Product 41

N³-(3-Pyrrolidin-1-yl-propyl)-pyridine-3,4-diamine 1.300 g (5.940 mmol) 3-bromo-4-nitro-pyridine-1-oxide and 0.980 g (7.430 mmol) 3-pyrrolidin-1-yl-propylamine was added to a suspension of 0.820 g (5.940 mmol) potassium carbonate in 20 mL DMF and the mixture was stirred for 3 hours at 90° C. The solvent was evaporated i. vac. and the residue purified by column chromatography (Alox (neutral, activity II-III), gradient dichloromethane/MeOH 100:0→95:5 v/v) (0.950 g, 60% of theory). 0.900 g (3.380 mmol) of the intermediate product was added to a suspension of 300 mg Pd/C in 10 mL EtOH and the mixture was hydrogenated for 4.5 hours at RT and 50 psi H₂-pressure. The catalyst was removed by filtration and the filtrate evaporated i. vac. The product is present in admixture with the corresponding pyridine-N-oxide and was used in the next reaction step without any further purification.

Yield: 35% of theory ESI-MS: (M+H)⁺=221

Intermediate Product 42

N²-Methyl-4-pyrrolidin-1-ylmethyl-benzene-1,2-diamine

To a solution of 0.700 g (3.569 mmol) 3-methylamino-4-nitro-benzoic acid and 0.58 mL (7.000 mmol) pyrrolidine in 40 mL THF was added 1.156 g (3.600 mmol) TBTU and the mixture was stirred for 3 hours at RT. The reaction mixture was diluted with EtOAc, the org. phase was washed with semisat. aqueous sodium bicarbonate solution, dried over magnesium sulphate and evaporated i. vac. (0.700 g, 79% of theory).

Under a nitrogen atmosphere a solution of the intermediate product in 15 mL THF was slowly added dropwise to a suspension of 76 mg (2.000 mmol) lithium aluminium hydride in 15 mL THF and the mixture was refluxed for 16 hours. After cooling another 35 mg lithium aluminium hydride were added and the mixture was refluxed for a further 8 hours. Excess lithium aluminium hydride was decomposed by the Fieser method with water and aqueous NaOH solution and filtered off. The filtrate was diluted with EtOAc, the org. phase was washed with sat. aqueous NaCl solution, dried over magnesium sulphate and evaporated i. vac. The crude product was purified by column chromatography (silica gel, gradient dichloromethane/MeOH/sat. aqueous ammonia 100:0:0→90:10:1 v/v/v).

Yield: 60 mg (21% of theory) R_f=0.20 (silica gel, dichloromethane/MeOH/sat. aqueous ammonia 90/10/1 v/v/v) ESI-MS: (M+H)⁺=206

Intermediate Product 43

Ethyl-2-amino-3-(3,4-dibromo-phenyl)-propionate 10.69 g (40.00 mmol) Ethyl-(benzhydrylidene-amino)-acetate, 1.87 g (5.80 mmol) tetrabutylammonium bromide and 20.00 g (45.12 mmol) of 1,2-dibromo-4-bromomethyl-benzene were added to a suspension of 14.00 g (101.30 mmol) potassium carbonate in 300 mL acetonitrile and 2.7 mL water and the mixture was refluxed for 20 hours. The reaction mixture was cooled, filtered and the filtrate evaporated i. vac. The residue was taken up in 120 mL ether, combined with semiconc. aqueous HCl and the mixture was stirred vigorously for 1 hour. The ethereal phase was separated off and the aqueous phase washed with ether. The aqueous phase was neutralised with sat. aqueous sodium bicarbonate solution and exhaustively extracted with EtOAc. The combined org. extracts were dried over sodium sulphate and evaporated down i. vac. The crude product was purified by column chromatography (silica gel, EtOAc).

Yield: 8.27 g (59% of theory) R_f=0.59 (silica gel, EtOAc)

Intermediate Product 44

Ethyl 3-(3,4-dibromo-phenyl)-2-[4-(2-oxo-1,2,4,5-tetrahydro-1,3-benzodiazepin-3-yl)-piperidin-1-yl]-propionate A solution of 8.27 g (23.56 mmol) ethyl 2-amino-3-(3,4-dibromo-phenyl)-propionate (Intermediate product 43) in 30 mL DMF was slowly added dropwise to a solution 10 of 4.20 g (24.31 mmol) CDT in 50 mL DMF at 0° C. and the mixture was stirred for 30 minutes at 0° C. and for 30 minutes at RT. 5.90 g (24.05 mmol) 3-Piperidin-4-yl-1,3,4,5-tetrahydro-1,3-benzodiazepin-2-one was added and the mixture was stirred for 16 hours at RT. The reaction mixture was poured onto 250 mL ice water, 150 mL EtOAc was added and stirred vigorously for 1 hour. The precipitate formed was filtered off and dried in the air.

Yield: 10.20 g (68% of theory) R_f=0.45 (silica gel, EtOAc)

Intermediate Product 45

3-(3,4-Dibromo-phenyl)-2-[4-(2-oxo-1,2,4,5-tetrahydro-1, 3-benzodiazepin-3-yl)-piperidin-1-yl]-propionic acid To a solution of 11.62 g (18.67 mmol) ethyl 3-(3,4-dibromo-phenyl)-2-[4-(2-oxo-1,2,4,5-tetrahydro-1,3-benzodiazepin-3-yl)-piperidin-1-yl]-propionate (Intermediate product 44) in 100 mL EtOH was added a solution of 5.00 g (125.00 mmol) sodium hydroxide in 50 mL water and the mixture was refluxed for 1 hour. Ethanol was evaporated i. vac. and the residue was diluted with 50 mL water. 65 mL of 2 M aqueous HCl was slowly added dropwise, the precipitate formed was filtered off and dried i. vac.

Yield: 11.09 g (quantitative yield) ESI-MS: (M–H)⁻=591/593/595 (Br₂)

Intermediate Product 46

Diethyl 2-acetylamino-2-(3,4-diethyl-benzyl)-malonate

Under a nitrogen atmosphere 8.14 g (354 mmol) of sodium was added in batches to 200 mL abs. EtOH and stirred until fully dissolved. 76.9 g (354 mmol) diethyl 2-acetylaminomalonate was then added to this solution, whereupon the sodium salt formed was precipitated. After the addition of 150 mL 1,4-dioxane a solution of 80 g (352 mmol) of 4-bromomethyl-1,2-diethyl-benzene in 500 mL of 1,4-dioxane was added dropwise to this suspension. The reaction solution was kept at 50° C for 2 hours and then stirred for 16 hours at RT. The solvent was distilled off i. vac., the oily residue was combined with water, while the product was obtained in the form of white crystals. These were suction filtered, washed with water and reacted without any further purification.

R_f=0.35 (silica gel, petroleum ether/EtOAc 2/1 v/v)

Intermediate Product 47

2-Amino-3-(3,4-diethyl-phenyl)-propionic acid

The crude Intermediate product 46 was dissolved in 250 mL AcOH and combined with 250 mL conc. aqueous HCl and 150 mL water. The reaction solution was refluxed for 3 hours, the solvents were evaporated i. vac., the residue taken up in EtOH, the precipitate formed was suction filtered and washed with diethyl ether.

Yield: 45 g (57% of theory) R_f=0.35 (silica gel, EtOAc/MeOH/AcOH 90/10/3 v/v/v) ESI-MS: (M+H)⁺=222

Intermediate Product 48

Methyl-2-amino-3-(3,4-diethyl-phenyl)-propionate 41 g (159 mmol) 2-Amino-3-(3,4-diethyl-phenyl)-propionic acid (Intermediate product 47) was combined with 300 mL HCl-sat. MeOH and left to stand for 16 hours at RT, during which time the desired hydrochloride was precipitated. The mixture was heated to 50° C., whereupon HCl was given off and the product went back into solution. The solution was evaporated down i. vac. to 1/3 of its original volume, the product precipitated was stirred with ether, suction filtered and washed twice with ether. The crude product was reacted without any further purification.

Yield: 42 g (97% of theory) $R_f$=0.7 (silica gel, MeOH)

ESI-MS: $(M+H)^+$=236

Intermediate Product 49

Methyl-3-(3,4-diethyl-phenyl)-2-{[4-(2-oxo-1,2,4,5-tetrahydro-1,3-benzodiazepin-3-yl)-piperidin-1-carbonyl]-amino}-propionate 7.4 g (45 mmol) of CDT was added to a solution of 10.5 g (44.6 mmol) methyl-2-amino-3-(3,4-diethyl-phenyl)-propionate (Intermediate product 48) in 250 mL THF cooled to 0° C. and the resulting mixture was stirred for a further 30 minutes at this temperature. Then 10.9 g (44.6 mmol) 3-piperidin-4-yl-1,3,4,5-tetrahydro-1,3-benzodiazepin-2-one was added, while the reaction solution was kept at this temperature for a further 20 minutes, before being refluxed for 30 minutes. The solvent was eliminated in vacuo, the residue was taken up in sat. sodium bicarbonate solution, exhaustively extracted with ether/EtOAc (1:1) and dried over magnesium sulphate. After removal of the drying agent and solvent the crude product was reacted without any further purification.

Yield: quantitative $R_f$=0.6 (silica gel, EtOAc/petroleum ether 6/4 v/v)

Intermediate Product 50

3-(3,4-Diethyl-phenyl)-2-{[4-(2-oxo-1,2,4,5-tetrahydro-1,3-benzodiazepin-3-yl)-piperidin-1-carbonyl]-amino}-propionic acid 26 g of the crude intermediate product 49 was dissolved in 200 mL EtOH, combined with 2.3 g (55 mmol) lithium hydroxide and stirred for 16 hours. The reaction solution was evaporated down i. vac., the residue taken up with water, extracted with ether, acidified with 15% aqueous citric acid solution and exhaustively extracted with EtOAc. The combined org. phases were dried over magnesium sulphate and after removal of the drying agent and solvent reacted without any further purification.

Yield: 19 g (75% of theory) $R_f$=0.1 (silica gel, EtOAc/petroleum ether 6/4 v/v)

Intermediate Product 51

Ethyl 2-amino-3-(3,5-bis-trifluoromethyl-phenyl)-propionate

The intermediate product was obtained analogously to intermediate product 43 starting from ethyl (benzhydrylidene-amino)-acetate and 1-bromomethyl-3,5-bis-trifluoromethyl-benzene as the hydrochloride salt.

Yield: 91% of theory ESI-MS: $(M+H)^+$=330

Intermediate Product 52

Ethyl 3-(3,5-bis-trifluoromethyl-phenyl)-2-{[4-(2-oxo-1,2,4,5-tetrahydro-1,3-benzodiazepin-3-yl)-piperidine-1-carbonyl]-amino}-propionate The intermediate product was obtained analogously to intermediate product 44 starting from ethyl 2-amino-3-(3,5-bis-trifluoromethyl-phenyl)-propionate (Intermediate product 51), 1 equivalent Honig base and 3-piperidin-4-yl-1,3,4,5-tetrahydro-1,3-benzodiazepin-2-one. The crude product was purified by column chromatography (silica gel, EtOAc/cyclohexane 4/1 v/v) purified.

Yield: 19% of theory $R_f$=0.63 (silica gel, EtOAc) ESI-MS: $(M+H)^+$=601

Intermediate product 53

3-(3,5-Bis-trifluoromethyl-phenyl)-2-{[4-(2-oxo-1,2,4,5-tetrahydro-1,3-benzodiazepin-3-yl)-piperidine-1-carbonyl]-amino}-propionic acid The intermediate product was obtained analogously to intermediate product 45 starting from ethyl 3-(3,5-bis-trifluoromethyl-phenyl)-2-{[4-(2-oxo-1,2,4,5-tetrahydro-1,3-benzodiazepin-3-yl)-piperidine-1-carbonyl]-amino}-propionate (Intermediate product 52).

Yield: quantitative ESI-MS: $(M+H)^+$=573

Intermediate Product 54

(4-Amino-3-chloro-5-trifluoromethyl-phenyl)-methanol

To a solution of 10.0 g (41.7 mmol) 4-amino-3-chloro-5-trifluoromethyl-benzoic acid (Arzneim. Forsch. 1984, 1612-1624.) in 100 mL THF was added 7.13 g (44.0 mmol) CDI and the mixture was stirred at 40° C. until the development of gas had ended. While cooling 4.64 g (120 mmol) sodium borohydride was added to 300 mL water and the mixture was then stirred for 2 hours at RT. The reaction mixture was acidified with 10% aqueous HCl, stirred for 1 hour, neutralised with sat. aqueous sodium bicarbonate solution and exhaustively extracted with EtOAc. The combined org. extracts were washed with sat. aqueous sodium bicarbonate solution, dried over sodium sulphate and evaporated down i. vac. Column chromatography (silica gel, gradient dichloromethane/MeOH/conc. aqueous ammonia 100/0/0→87/10/3 v/v/v) yielded the product.

Yield: 5.4 g (57% of theory)

Intermediate Product 55

2-Chloro-4-chlormethyl-6-trifluoromethyl-phenylamine

To a solution of 1.00 g (4.43 mmol) (4-amino-3-chloro-5-trifluoromethyl-phenyl)-methanol (Intermediate product 54) in 50 mL dichloromethane was added at RT 0.94 mL (13.00 mmol) thionyl chloride and the mixture was stirred for 3 hours at RT. The reaction mixture was poured onto ice and the aqueous phase exhaustively extracted with dichloromethane. The combined org. phases were washed with ice-cold sodium bicarbonate solution, dried over sodium sulphate, filtered through activated charcoal and evaporated down i. vac. The crude product was used in the next reaction step without any further purification.

Yield: 1.08 g (quantitative yield) EI-MS: $M^+$=243/245/247 ($Cl_2$) $R_f$=0.81 (silica gel, petroleum ether/EtOAc 2/1 v/v/)

Intermediate Product 56

Diethyl 2-acetylamino-2-(4-amino-3-chloro-5-trifluoromethyl-benzyl)-malonate 24.11 g (0.11 mol) diethyl 2-acetylamino-malonate was added to a freshly prepared solution of 2.55 g (0.11 mol) sodium in 200 mL abs. EtOH under a nitrogen atmosphere and the mixture was stirred for 15 minutes at RT. A solution of 27.00 g (0.11 mol) 2-chloro-4-chlormethyl-6-trifluoromethyl-phenylamine (Intermediate product 55) in 100 mL 1,4-dioxane was rapidly added dropwise and the mixture was stirred for 4 hours at RT. 500 mL water were added and the mixture was stirred for a further 16 hours. The precipitate formed was filtered off, washed with water and dried i. vac.

Yield: 40.0 g (84% of theory) $R_f$=0.14 (silica gel, petroleum ether/EtOAc 2/1 v/v)

Intermediate Product 57

2-Amino-3-(4-amino-3-chloro-5-trifluoromethyl-phenyl)-propionic acid-hydrochloride To a solution of 40.0 g (94.16 mmol) diethyl 2-acetylamino-2-(4-amino-3-chloro-5-trifluoromethyl-benzyl)-malonate (Intermediate product 56) in 110 mL AcOH and 150 mL water was added 50 mL conc. aqueous HCl and the reaction mixture was heated to 140° C. for 4 hours. The precipitate formed was filtered off and discarded. The filtrate was evaporated i. vac., combined with 100 mL EtOH and stirred for 15 minutes at RT. The precipitate formed was filtered off, washed with EtOH and dried i. vac. The crude product was used in the next reaction step without any further purification.

Yield: 16 g (53% of theory) ESI-MS: $(M-H)^-=281/283$ (Cl)

Intermediate Product 58

Ethyl 2-amino-3-(4-amino-3-chloro-5-trifluoromethyl-phenyl)-propionate 16 g (50.14 mmol) 2-amino-3-(4-amino-3-chloro-5-trifluoromethyl-phenyl)-propionic acid-hydrochloride (Intermediate product 57) were dissolved in 350 mL HCl (12 M in EtOH) and stirred for 5 hours at RT. The reaction mixture was evaporated to 100 mL i. vac. and combined with 200 mL ether. The precipitate formed was filtered off, washed with ether and dried i. vac.

Yield: 12.2 g (70% of theory) ESI-MS: $(M+H)^+=311/313$ (Cl)

Intermediate Product 59

Ethyl 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionate 4.15 g (23.04 mmol) CDT was added to a suspension of 8.00 g (23.04 mmol) ethyl 2-amino-3-(4-amino-3-chloro-5-trifluoromethyl-phenyl)-propionate (Intermediate product 58) and 16.0 mL (115.00 mmol) triethylamine in 100 mL DMF at 0° C. and the mixture was stirred for 1.5 hours at 0° C. A solution of 5.64 g (23.00 mmol) 3-piperidin-4-yl-1,3,4,5-tetrahydro-1,3-benzodiazepin-2-one in 200 mL DMF was added and the mixture was heated to 100° C. for 2 hours. The reaction mixture was cooled to RT, diluted with 1.5 L water and stirred for a further 10 minutes. The precipitate formed was filtered off, washed with water and dried i. vac.

Yield: 13.0 g (97% of theory) ESI-MS: $(M+H)^+=582/584$ (Cl)

Intermediate Product 60

3-(4-Amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid To a solution of 13.00 g (22.34 mmol) ethyl 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionate (Intermediate product 59) in 100 mL EtOH was added 45 mL aqueous NaOH (1 M) and the mixture was stirred for 16 hours at RT. EtOH was evaporated i. vac., 45 mL aqueous HCl (1M) was added and 15 minutes stirred. The precipitate formed was filtered off, washed with water and dried i. vac. at 75° C.

Yield: 10.5 g (85% of theory) ESI-MS: $(M-H)^-=552/554$ (Cl)

Intermediate Product 61 tert. Butyl-4-(3,4-diethyl-phenyl)-3,3-bis-ethoxycarbonyl-butyrate

To a solution of 14.70 g (53.59 mmol) 1-tert.-butyl-4-ethyl 3-ethoxycarbonyl-succinate in 100 mL abs. THF was added batchwise under a nitrogen atmosphere and while cooling with ice 2.40 g (55.00 mmol) NaH (55% in mineral oil) and the mixture was stirred for 1 hour at RT. 11.00 g (48.43 mmol) of 4-bromomethyl-1,2-diethyl-benzene, dissolved in 50 mL abs. THF, was added dropwise and the mixture was stirred for 3 hours at RT. The reaction mixture was filtered and the filtrate evaporated i. vac. The residue was combined with water and the aqueous phase exhaustively extracted with EtOAc. The org. phase was with washed 1 M aqueous potassium hydrogen sulphate solution and water, dried over $MgSO_4$ and evaporated down i. vac. The crude product was used in the next reaction step without any further purification.

Yield: 20.30 g (quantitative yield) ESI-MS: $(M+Na)^+=423$ $R_f=0.48$ (eluant: petroleum ether/EtOAc 4/1 v/v)

Intermediate Product 62

4-(3,4-Diethyl-phenyl)-3,3-bis-ethoxycarbonyl-butyric acid

To a solution of 20.30 g (48.27 mmol) tert. butyl 4-(3,4-diethyl-phenyl)-3,3-bis-ethoxycarbonyl-butyrate (Intermediate product 61) in 100 mL $CH_2Cl_2$ was added 40 mL TFA while cooling with ice and the mixture was refluxed for 1 hour. The reaction mixture was evaporated down i. vac., the residue was combined with water and the aqueous phase exhaustively extracted with EtOAc. The combined org. extracts were washed with sat. aqueous NaCl solution, dried over sodium sulphate and evaporated i. vac.

Yield: 17.10 g (97% of theory) ESI-MS: $(M-H)^-=363$

Intermediate Product 63

Diethyl-2-(3,4-diethyl-benzyl)-2-{2-oxo-2-[4-(2-oxo-1,2,4,5-tetrahydro-1,3-benzodiazepin-3-yl)-piperidin-1-yl]-ethyl}-malonate 10.00 mL (56.83 mmol) of Hünig base was added dropwise to a solution of 17.00 g (46.65 mmol) 4-(3,4-diethyl-phenyl)-3,3-bis-ethoxycarbonyl-butyric acid (Intermediate product 62), 12.00 g (48.91 mmol) 3-piperidin-4-yl-1,3,4,5-tetrahydro-1,3-benzodiazepin-2-one, 16.00 g (49.84 mmol) TBTU and 6.50 g (47.14 mmol) HOBT in 300 mL THF and the mixture was stirred for 5 hours at RT. The reaction mixture was evaporated i. vac., the residue combined with sat. aqueous sodium bicarbonate solution and the aqueous phase exhaustively extracted with dichloromethane. The combined org. extracts were washed with water, dried over sodium sulphate and evaporated i. vac.

Yield: 14.00 g (51% of theory) ESI-MS: $(M+H)^+=592$

Intermediate Product 64

To a solution of 14.00 g (23.66 mmol) diethyl 2-(3,4-diethyl-benzyl)-2-{2-oxo-2-[4-(2-oxo-1,2,4,5-tetrahydro-1,3-benzodiazepin-3-yl)-piperidin-1-yl]-ethyl}-malonate (Intermediate product 63) in 150 mL EtOH was added 6.30 g (95.62 mmol) KOH, dissolved in 100 mL water, and the mixture was refluxed for 16 hours. EtOH was evaporated off i. vac., the reaction mixture was acidified to pH 4 with conc. aqueous HCl and 1 hour at RT. The precipitate formed was filtered off, washed with water and diisopropyl ether and dried i. vac.

Yield: 10.90 g (94% of theory) ESI-MS: $(M+H)^+=492$

45

Intermediate Product 65 tert. Butyl 4-(4-amino-3-chloro-5-trifluoromethyl-phenyl)-3,3-bis-ethoxycarbonyl-butyrate To a solution of 1.20 g (4.43 mmol) 1-tert.butyl-4-ethyl 3-ethoxycarbonyl-succinate in 50 mL abs. THF was added batchwise under a nitrogen atmosphere and while cooling with ice 193 mg (4.43 mmol) NaH (55% in mineral oil) and the mixture was stirred for 1 hour at RT. 1.1 g (4.43 mmol) of 2-chloro-4-chlormethyl-6-trifluoromethyl-phenylamine, dissolved in 10 mL abs. THF, was added dropwise and the mixture was stirred for 16 hours at RT. The reaction mixture was diluted with water and the aqueous phase extracted with EtOAc. The org. phase was dried over magnesium sulphate and evaporated down i. vac. The crude product was used in the next reaction step without any further purification.

Yield: 2.1 g (98% of theory) ESI-MS: (M+H)$^+$=482/484 (Cl) $R_f$=0.48 (silica gel, petroleum ether/EtOAc 4/1 v/v)

Intermediate Product 66

4-(4-Amino-3-chloro-5-trifluoromethyl-phenyl)-3,3-bis-ethoxycarbonyl-butyric acid To a solution of 30.0 g (62.25 mmol) tert. butyl 4-(4-amino-3-chloro-5-trifluoromethyl-phenyl)-3,3-bis-ethoxycarbonyl-butyrate (Intermediate product 65) in 200 mL CH$_2$Cl$_2$ was added 20 mL TFA while cooling with ice and the mixture was stirred for 16 hours at RT. The reaction mixture was evaporated i. vac. and the residue recrystallised from petroleum ether. The precipitate was filtered off, washed with petroleum ether and dried.

Yield: 23.6 g (89% of theory) ESI-MS: (M–H)$^-$=424/426 (Cl)

Intermediate Product 67

Diethyl-2-(4-amino-3-chloro-5-trifluoromethyl-benzyl)-2-{2-oxo-2-[4-(2-oxo-1,2,4,5-tetrahydro-1,3-benzodiazepin-3-yl)-piperidin-1-yl]-ethyl}-malonate To a solution of 13.00 g (30.53 mmol) 4-(4-amino-3-chloro-5-trifluoromethyl-phenyl)-3,3-bis-ethoxycarbonyl-butyric acid (Intermediate product 66) and 9.7 mL (70.00 mmol) triethylamine in 70 mL DMF was added at 0° C. 10.60 g (33.00 mmol) TBTU and the mixture was stirred for 1.5 hours at 0° C. A solution of 7.482 g (30.50 mmol) 3-piperidin-4-yl-1,3,4,5-tetrahydro-1,3-benzodiazepin-2-one in 50 mL DMF was added and the mixture was stirred for 16 hours at RT. The reaction mixture was evaporated down i. vac. and the residue was combined with saturated aqueous sodium bicarbonate solution and EtOAc. The precipitate formed was filtered off, suspended in acetone, filtered off again, washed with acetone and dried i. vac.

Yield: 17.90 g (90% of theory) ESI-MS: (M+H)$^+$=653/655 (Cl)

Intermediate Product 68

2-(4-Amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyric acid To a solution of 17.90 g (27.41 mmol) diethyl 2-(4-amino-3-chloro-5-trifluoromethyl-benzyl)-2-{2-oxo-2-[4-(2-oxo-1,2,4,5-tetrahydro-1,3-benzodiazepin-3-yl)-piperidin-1-yl]-ethyl}-malonate (Intermediate product 67) in 1200 mL EtOH was added 5.48 g (137.00 mmol) NaOH in 500 mL water and the mixture was refluxed for 4 hours. EtOH was evaporated off i. vac. and the aqueous phase was acidified to pH 2 with conc. aqueous HCl. The precipitate formed was filtered off, washed with water and dried i. vac.

Yield: 14.80 g (98% of theory) ESI-MS: (M–H)$^-$=551/553 (Cl)

46

Preparation of the End Compounds:

EXAMPLE 1

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[1-(3-dimethylamino-propyl)-1H-benzimidazol-2-yl]-ethyl}-amide

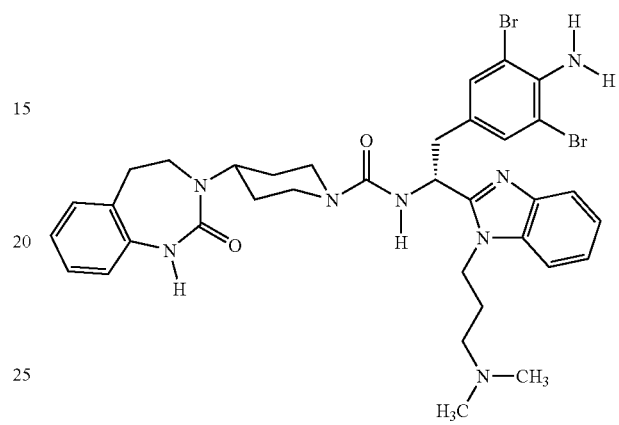

The solution of 1.0 g (1.30 mmol) 4-(2-oxo-1,2,4,5-tetrahydro-1,3-benzodiazepin-3-yl)-piperidin-1-carboxylic acid-{(R)-2-(4-amino-3,5-dibromo-phenyl)-1-[2-(3-dimethylamino-propylamino)-phenylcarbamoyl]-ethyl}-amide (Intermediate product 1) in 60 mL 1,4-dioxane was combined with 200 mg of p-toluenesulphonic acid and refluxed for 15 minutes. The solvent was eliminated i. vac., the residue taken up in water and made alkaline by the addition of aqueous sodium bicarbonate solution. The precipitate formed was filtered off, triturated with acetone and dried. 0.35 g (36% of theory) of colourless crystals were obtained, $R_f$=0.55 (silica gel, dichloromethane/MeOH/cyclohexane/conc. aqueous ammonia 70/15/15/2 v/v/v/v).

ESI-MS: (M+H)$^+$=751/753/755 (Br$_2$).

EXAMPLE 2

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[1-(2-dimethylamino-ethyl)-1H-benzimidazol-2-yl]-ethyl}-amide

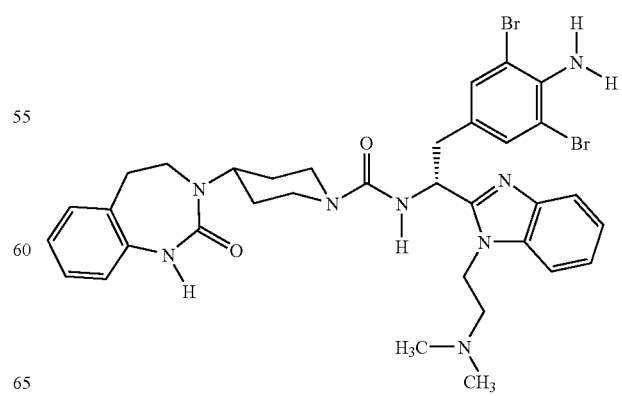

The product was obtained analogously to Example 1 from 4-(2-oxo-1,2,4,5-tetrahydro-1,3-benzodiazepin-3-yl)-piperidin-1-carboxylic acid-{(R)-2-(4-amino-3,5-dibromo-phenyl)-1-[2-(2-dimethylamino-ethylamino)-phenylcarbamoyl]-ethyl}-amide (Intermediate product 2).

Yield: 36% of theory $R_f$=0.55 (silica gel, dichloromethane/MeOH/cyclohexane/conc. aqueous ammonia 70/15/15/2 v/v/v/v) ESI-MS: (M+H)$^+$=751/753/755 (Br$_2$)

EXAMPLE 3

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(1-methyl-1H-benzimidazol-2-yl)-ethyl]-amide

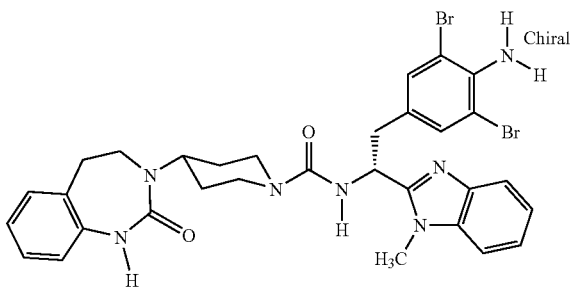

The product was obtained analogously to Example 1 from 4-(2-oxo-1,2,4,5-tetrahydro-1,3-benzodiazepin-3-yl)-piperidin-1-carboxylic acid-[(R)-2-(4-amino-3,5-dibromo-phenyl)-1-(2-methylamino-phenylcarbamoyl)-ethyl]-amide (Intermediate product 3).

Yield: 46% of theory $R_f$=0.64 (silica gel, dichloromethane/MeOH/cyclohexane/conc. aqueous ammonia 70/15/15/2 v/v/v/v) ESI-MS: (M+H)$^+$=694/696/698 (Br$_2$)

EXAMPLE 4

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(1H-benzimidazol-2-yl)-ethyl]-amide

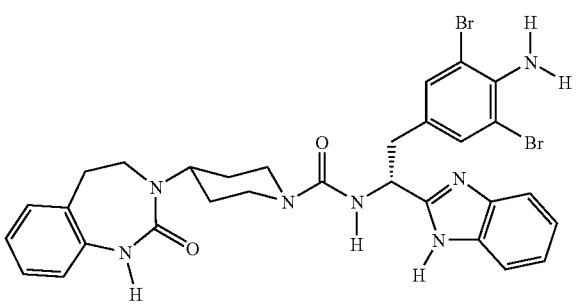

The product was obtained analogously to Example 1 from 4-(2-oxo-1,2,4,5-tetrahydro-1,3-benzodiazepin-3-yl)-piperidin-1-carboxylic acid-[(R)-2-(4-amino-3,5-dibromo-phenyl)-1-(2-amino-phenylcarbamoyl)-ethyl]-amide (Intermediate product 4).

Yield: 27% of theory $R_f$=0.69 (silica gel, dichloromethane/MeOH/cyclohexane/conc. aqueous ammonia 70/15/15/2 v/v/v/v) ESI-MS: (M+H)$^+$=680/682/684 (Br$_2$)

EXAMPLE 5

Methyl-2-((R)-2-(4-amino-3,5-dibromo-phenyl)-1-{[4-(2-oxo-1,4-dihydro-2H-quinazolin-3-yl)-piperidin-1-carbonyl]-amino}-ethyl)-1H-benzimidazole-5-carboxylate

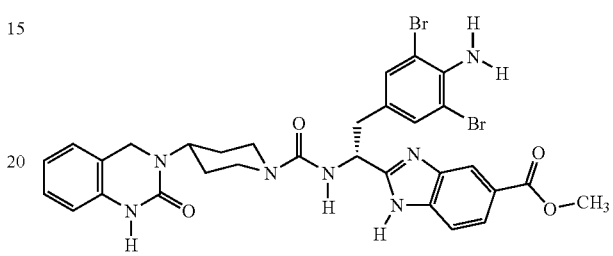

The product was obtained analogously to Example 1 from methyl 4-amino-3-((R)-3-(4-amino-3,5-dibromo-phenyl)-2-{[4-(2-oxo-1,4-dihydro-2H-quinazolin-3-yl)-piperidin-1-carbonyl]-amino}-propionylamino)-benzoate (Intermediate product 5).

Yield: 95% of theory ESI-MS: (M+H)$^+$=724/726/728 (Br$_2$)

EXAMPLE 6

Methyl-2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylate

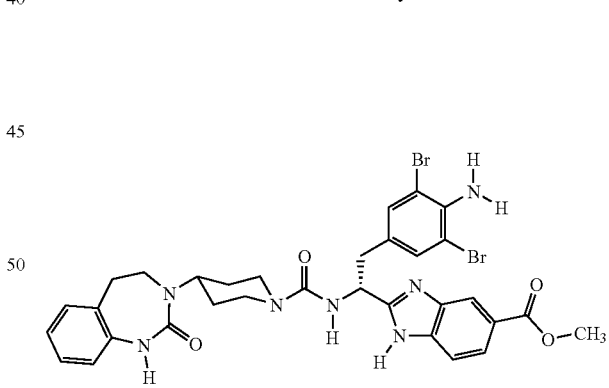

The product was obtained analogously to Example 1 from 4-amino-3-((R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionylamino)-benzoate methyl (Intermediate product 6).

Yield: 85% of theory ESI-MS: (M+H)$^+$=738/740/742 (Br$_2$)

EXAMPLE 7

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(1-butyl-1H-benzimidazol-2-yl)-ethyl]-amide

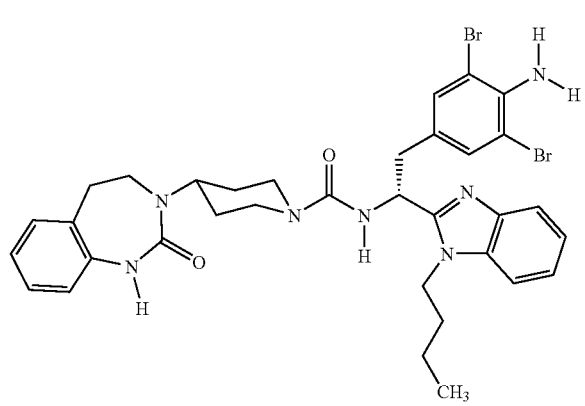

The product was obtained analogously to Example 1 from 4-(2-oxo-1,2,4,5-tetrahydro-1,3-benzodiazepin-3-yl)-piperidin-1-carboxylic acid-[(R)-2-(4-amino-3,5-dibromo-phenyl)-1-(2-butylamino-phenylcarbamoyl)-ethyl]-amide (intermediate product 7).

Yield: 20% of theory ESI-MS: (M+H)$^+$=736/738/740 (Br$_2$)

EXAMPLE 8

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[1-(3-pyrrolidin-1-yl-propyl)-1H-benzimidazol-2-yl]-ethyl}-amide

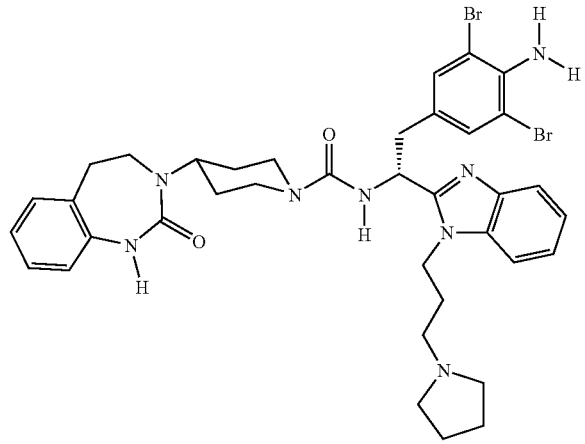

The product was obtained analogously to Example 1 from 4-(2-oxo-1,2,4,5-tetrahydro-1,3-benzodiazepin-3-yl)-piperidin-1-carboxylic acid-{(R)-2-(4-amino-3,5-dibromo-phenyl)-1-[2-(3-pyrrolidin-1-yl-propylamino)-phenylcarbamoyl]-ethyl}-amide (Intermediate product 8).

Yield: 9% of theory ESI-MS: (M+H)$^+$=791/793/795 (Br$_2$)

EXAMPLE 9

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(1-pyridin-3-ylmethyl-1H-benzimidazol-2-yl)-ethyl]-amide

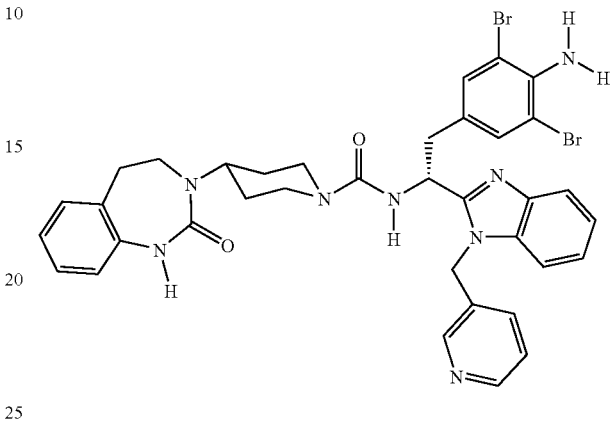

The product was obtained analogously to Example 1 from 4-(2-oxo-1,2,4,5-tetrahydro-1,3-benzodiazepin-3-yl)-piperidin-1-carboxylic acid-((R)-2-(4-amino-3,5-dibromo-phenyl)-1-{2-[(pyridin-3-ylmethyl)-amino]-phenylcarbamoyl}-ethyl)-amide (Intermediate product 9).

Yield: 31% of theory ESI-MS: (M+H)+=771/773/775 (Br$_2$)

EXAMPLE 10

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(1-benzyl-1H-benzimidazol-2-yl)-ethyl]-amide

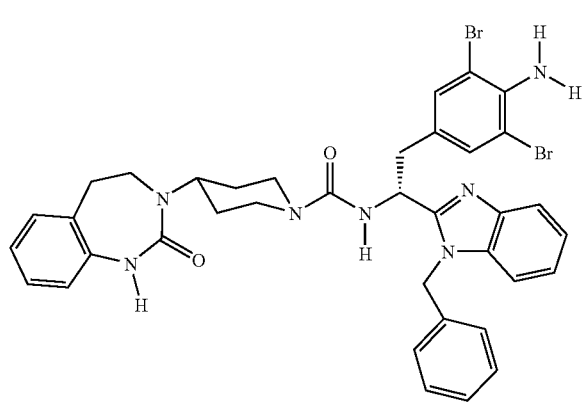

The product was obtained analogously to Example 1 from 4-(2-oxo-1,2,4,5-tetrahydro-1,3-benzodiazepin-3-yl)-piperidin-1-carboxylic acid-[(R)-2-(4-amino-3,5-dibromo-phenyl)-1-(2-benzylamino-phenylcarbamoyl)-ethyl]-amide (Intermediate product 10).

Yield: 47% of theory ESI-MS: (M+H)$^+$=770/772/774 (Br$_2$)

EXAMPLE 11

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[1-(1-methyl-piperidin-4-ylmethyl)-1H-benzimidazol-2-yl]-ethyl}-amide

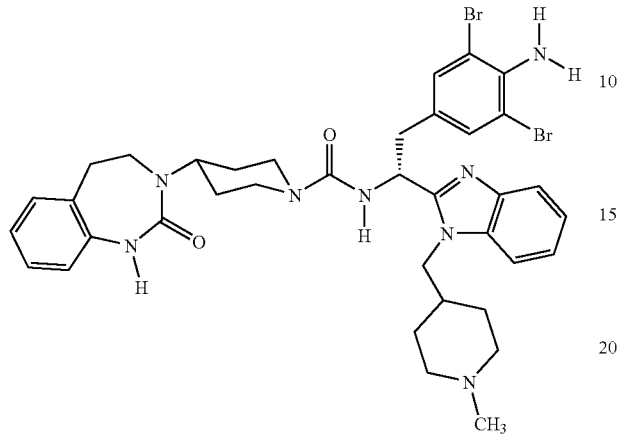

The product was obtained analogously to Example 1 from 4-(2-oxo-1,2,4,5-tetrahydro-1,3-benzodiazepin-3-yl)-piperidin-1-carboxylic acid-((R)-2-(4-amino-3,5-dibromo-phenyl)-1-{2-[(1-methyl-piperidin-4-yl methyl)-amino]-phenylcarbamoyl}-ethyl)-amide (Intermediate product 11).

Yield: 25% of theory ESI-MS: (M+H)$^+$=791/793/795 (Br$_2$)

EXAMPLE 12

2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acid

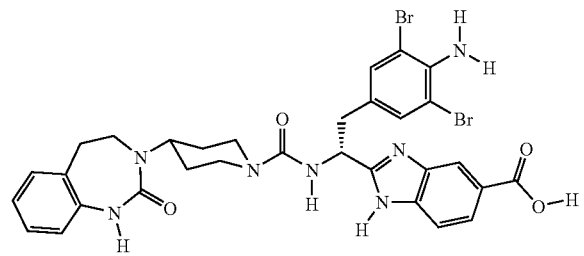

To a solution of 1.5 g (2.03 mmol) methyl 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylate in 100 mL MeOH was added a solution of 0.4 g lithium hydroxide in 50 mL water and the mixture was stirred for 2 days at RT. The organic solvent was eliminated i. vac. and the aqueous residue was extracted three times with in each case 20 mL dichloromethane. The aqueous phase was then acidified by the addition of 25 mL of a 1 N hydrochloric acid and the product precipitated was filtered off and dried. 1.1 g (75% of theory) of colourless crystals were obtained, R$_f$=0.22 (silica gel, dichloromethane/MeOH/cyclohexane/conc. aqueous ammonia 70/15/15/2 v/v/v/v).

ESI-MS: (M+H)$^+$=724/726/728 (Br$_2$).

EXAMPLE 13

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[6-(4-methyl-piperazin-1-carbonyl)-1H-benzimidazol-2-yl]-ethyl}-amide

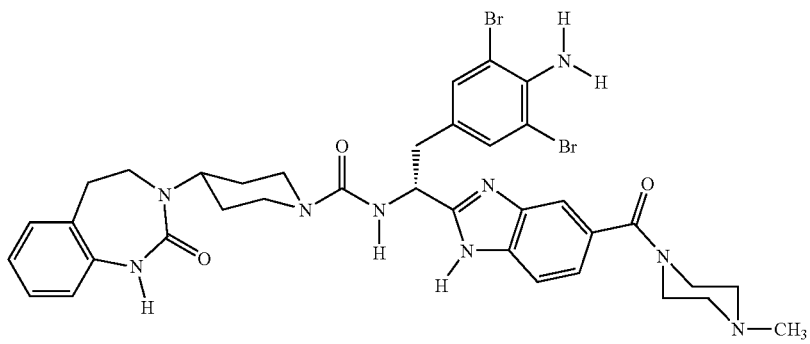

To a solution of 0.20 g (0.276 mmol) 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acid in 50 mL THF was added 0.10 g (0.311 mmol) TBTU, 0.042 g (0.305 mmol) HOBt and 0.2 mL Hünig base and this mixture was stirred for 20 minutes at RT. To this mixture was added 34 pL (0.30 mmol) 1-methylpiperazine and the mixture was stirred for 2 days at RT. The solvent was eliminated i. vac., the residue combined with sat. aqueous sodium bicarbonate solution and exhaustively extracted with dichloromethane. The combined dichloromethane extracts were combined with aqueous potassium hydrogen sulphate solution and the precipitate formed was filtered off and dried. 0.12 g (54% of theory) of colourless solid was obtained, R$_f$=0.40 (silica gel, dichloromethane/MeOH/cyclohexane/conc. aqueous ammonia 70/15/15/2 v/v/v/v).

ESI-MS: (M+H)$^+$=806/808/810 (Br$_2$)

EXAMPLE 14

2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acid-(3-dimethylamino-propyl)-amide

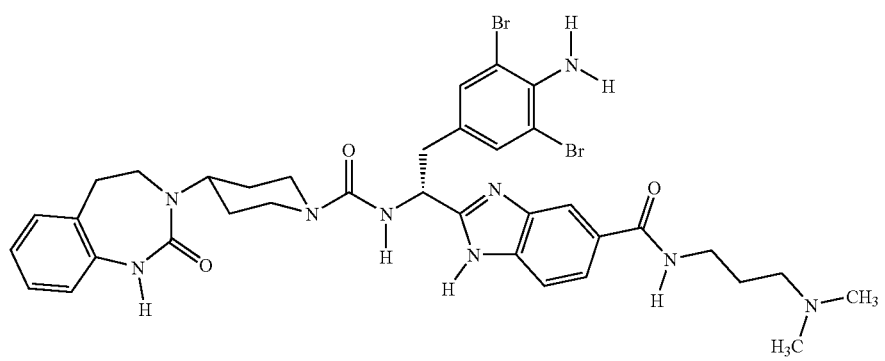

To a mixture of 0.30 g (0.414 mmol) 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acidin 50 mL THF was added 0.16 g (0.498 mmol) TBTU, 0.065 g (0.47 mmol) HOBt and 0.2 mL Hünig base and this mixture was stirred for 30 minutes at RT. The undissolved fraction of this mixture was dissolved by the addition of DMF, then 55 µL (0.433 mmol) 3-dimethylamino-1-propylamine was added dropwise and the resulting mixture was stirred for 16 hours. The solvent was eliminated i. vac., the residue taken up in sat. aqueous sodium bicarbonate solution and exhaustively extracted with dichloromethane. The combined extracts were washed with water, dried over sodium sulphate and evaporated down i. vac. The residue was purified by column chromatography on silica gel using dichloromethane/MeOH. 0.11 g (33% of theory) colourless crystals were obtained, $R_f$=0.22 (silica gel, dichloromethane/MeOH/cyclohexane/conc. aqueous ammonia 70/15/15/2 v/v/v/v). ESI-MS: (M−H)=806/808/810 (Br$_2$).

EXAMPLE 15

2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acid-(2-dimethylamino-ethyl)-amide

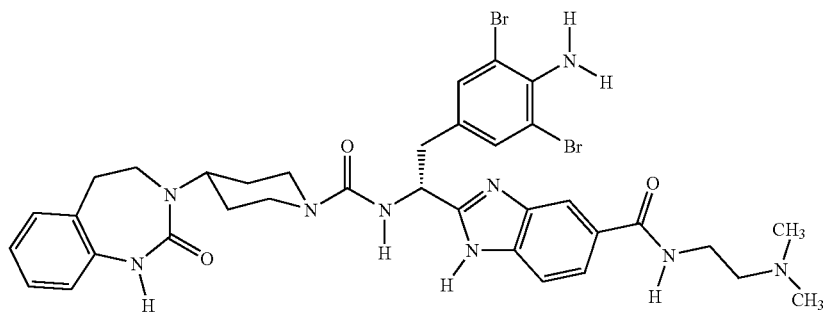

The product was prepared analogously to Example 14 starting from 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1H-benzimidazole-5-carboxylic acid and $N^1,N^1$-dimethyl-ethan-1,2-diamine.

Yield: 24% of theory $R_f$=0.36 (silica gel, dichloromethane/MeOH/cyclohexane/conc. aqueous ammonia 70/15/15/2 v/v/v/v) ESI-MS: (M+H)$^+$=794/796/798 (Br$_2$)

EXAMPLE 16

4-(2-Oxo-1,4-dihydro-2H-quinazolin-3-yl)-piperidin--carboxylic acid-{(R)-2-(4-amino-3,5-dibromo-phenyl)-1-[1-(3-dimethylamino-propyl)-5-phenyl-1H-imidazol-2-yl]-ethyl}-amide

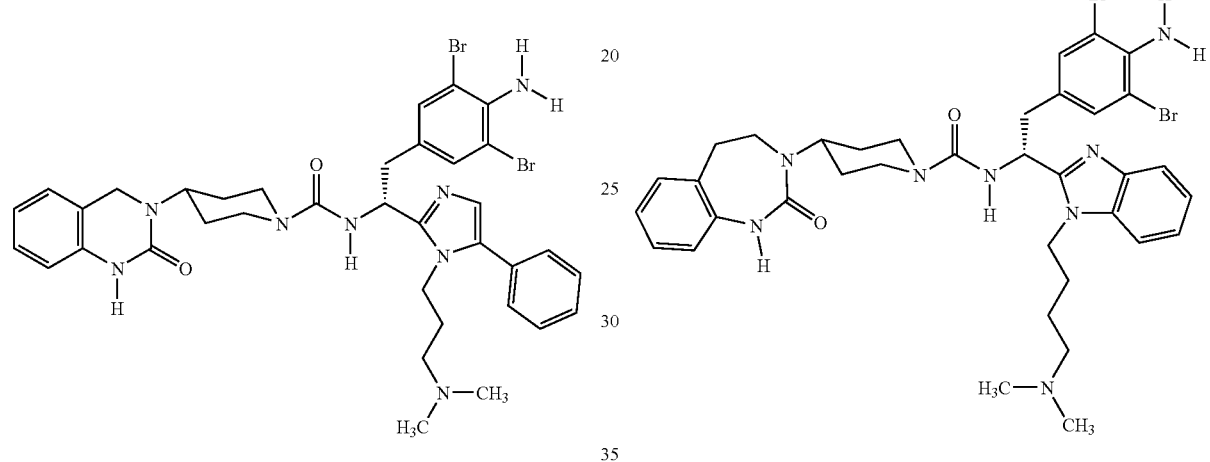

A mixture of 0.185 g (0.30 mmol) tert. butyl {(R)-2-(4-amino-3,5-dibromo-phenyl)-1-[1-(3-dimethylamino-propyl)-5-phenyl-1H-imidazol-2-yl]-ethyl}-carbaminate (Intermediate product 13), 0.065 g (0.60 mmol) anisol and 3 mL dichloromethane was combined with 0.58 mL (7.45 mmol) TFA and stirred for 2.5 hours at RT. The solvents were eliminated i. vac., the crude 4-{(R)-2-amino-2-[1-(3-dimethylamino-propyl)-5-phenyl-1H-imidazol-2-yl]-ethyl}-2,6-dibromo-phenylamine formed was taken up in 5 mL THF, and 0.153 mL (0.89 mmol) Hünig base and 0.054 g (0.328 mmol) CDT were added with stirring and cooling over an ice bath. The mixture was stirred for 30 minutes while cooling with ice and for 30 minutes at RT, combined with 0.69 g (0.30 mmol) 3-piperidin-4-yl-3,4-dihydro-1H-quinazoline-2-one, mL THF and 2 mL DMF and refluxed for 2.5 hours. The reaction mixture was evaporated down i. vac., the residue dissolved in EtOAc, washed repeatedly with water and sat. aqueous NaCl solution and dried over magnesium sulphate. After elimination of the solvent an oily residue remained which was purified by column chromatography on silica gel using dichloromethane/MeOH/conc. aqueous ammonia 90/9/1. 0.03 g (13% of theory) of the desired product was obtained.

ESI-MS: (M−H)=777/779/781 (Br$_2$).

EXAMPLE 17

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[1-(4-dimethylamino-butyl)-1H-benzimidazol-2-yl]-ethyl}-amide

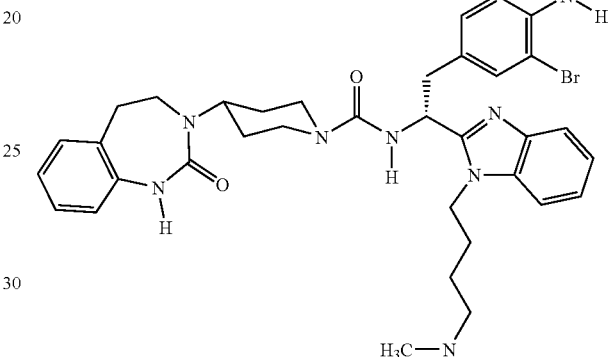

To a solution of 200 mg (0.609 mmol) (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid in 10 mL DMF/THF (2:1 v/v) was added at RT 116 mg (0.361 mmol) TBTU and 65 µL (0.369 mmol) Hünig base and the mixture was stirred for 20 minutes. 75 mg (0.362 mmol) N-(4-dimethylamino-butyl)-benzene-1,2-diamine (Intermediate product 18) was added and stirred for 16 hours at RT. The mixture was filtered through basic Alox, washed again with 10 mL DMF and evaporated down i. vac. The residue was dissolved in 20 mL dioxane, combined with 100 mg p-toluenesulphonic acid and refluxed for 45 minutes. The solvent was evaporated off i. vac. and the residue taken up in dichloromethane. The org. phase was washed with 15% aqueous potassium carbonate solution, dried over sodium sulphate and evaporated down i. vac. The crude product was purified by HPLC-MS (Zorbax Bonus C18 amide-phase 5 µm, gradient 0.15% formic acid in water/acetonitrile 10/90→90/10 v/v) and then lyophilised. Yield: 10 mg (4% of theory) $R_f$=0.43 (silica gel, dichloromethane/MeOH/cyclohexane/conc. aqueous ammonia 70/15/15/2 v/v/v/v) ESI-MS: (M+H)$^+$=779/781/783 (Br$_2$)

EXAMPLE 18

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[1-(1-methyl-piperidin-4-yl)-1H-benzimidazol-2-yl]-ethyl}-amide

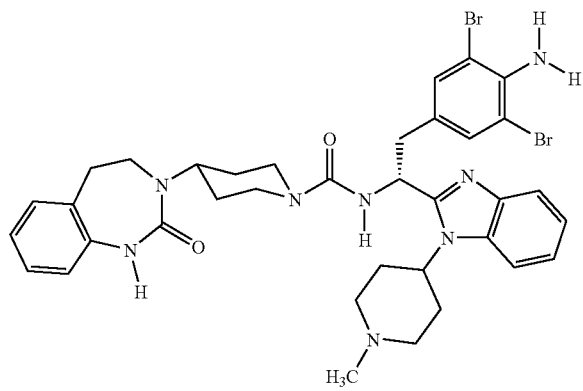

The product was obtained analogously to Example 17 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and N-(1-methyl-piperidin-4-yl)-benzene-1,2-diamine (Intermediate product 19).

Yield: 9% of theory $R_f$=0.50 (silica gel, dichloromethane/MeOH/cyclohexane/conc. aqueous ammonia 70/15/15/2 v/v/v/v) ESI-MS: $(M+H)^+$=777/779/781 (Br$_2$)

EXAMPLE 19

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(1-cyclohexyl-1H-benzimidazol-2-yl)-ethyl]-amide

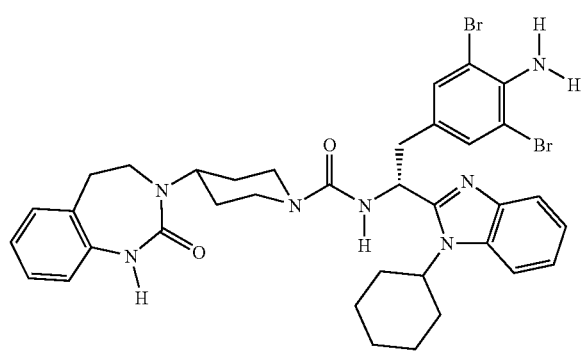

The product was obtained analogously to Example 17 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid N-cyclohexyl-benzene-1,2-diamine. The crude product was purified by column chromatography (silica gel, dichloromethane/MeOH/conc. aqueous ammonia 90/10/1 v/v/v) and triturated with diisopropylether.

Yield: 21% of theory $R_f$=0.81 (silica gel, dichloromethane/MeOH/cyclohexane/conc. aqueous ammonia 70/15/15/2 v/v/v/v) ESI-MS: $(M+H)^+$=762/764/766 (Br$_2$)

EXAMPLE 20

4-(2-Oxo-1,2,4,5-tetrahydro-1,3-benzodiazepin-3-yl)-piperidin-1-carboxylic acid-[(R)-2-(4-amino-3,5-dibromo-phenyl)-1-(1-cyclopentyl-1H-benzimidazol-2-yl)-ethyl]-amide

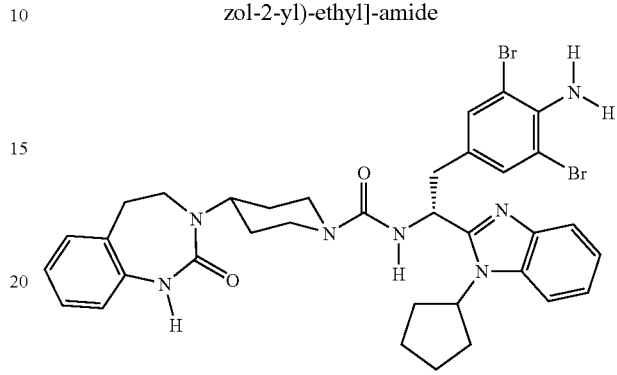

The product was obtained analogously to Example 17 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and N-cyclopentyl-benzene-1,2-diamine. The crude product was purified by column chromatography (silica gel, dichloromethane/MeOH/conc. aqueous ammonia 90/10/1 v/v/v) purified and triturated with diisopropylether.

Yield: 31% of theory $R_f$=0.78 (silica gel, dichloromethane/MeOH/cyclohexane/conc. aqueous ammonia 70/15/15/2 v/v/v/v) ESI-MS: $(M+H)^+$=748/750/752 (Br$_2$)

EXAMPLE 21

4-(2-Oxo-1,2,4,5-tetrahydro-1,3-benzodiazepin-3-yl)-piperidin-1-carboxylic acid{(R)-2-(4-amino-3,5-dibromo-phenyl)-1-[1-(5-dimethylamino-pentyl)-1H-benzimidazol-2-yl]-ethyl}-amide

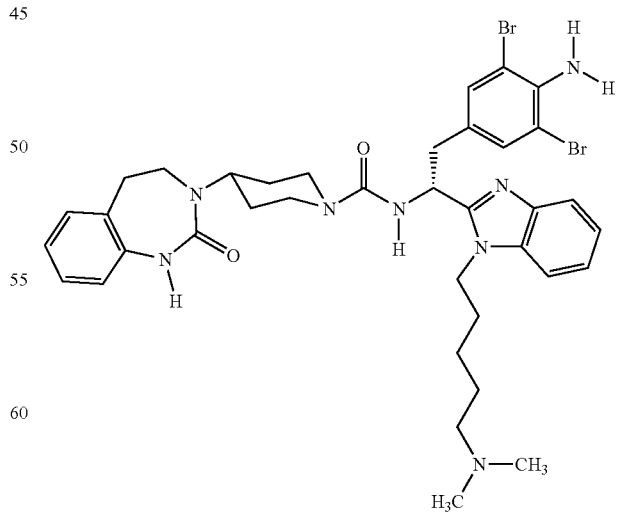

The product was obtained analogously to Example 17 starting from (R)-3-(4-amino-3,5-dibromo-phenyl)-2-{[4-

(2-oxo-1,2,4,5-tetrahydro-1,3-benzodiazepin-3-yl)-piperidin-1-carbonyl]-amino}-propionic acid and N-(5-dimethylamino-pentyl)-benzene-1,2-diamine (Intermediate product 20). The crude product was purified by column chromatography (silica gel, dichloromethane/MeOH/conc. aqueous ammonia 90/10/ 1 v/v/v) and triturated with diisopropylether.

Yield: 67% of theory $R_f$=0.55 (silica gel, dichloromethane/MeOH/cyclohexane/conc. aqueous ammonia 70/15/15/2 v/v/v/v) ESI-MS: (M+H)$^+$=793/795/797 (Br$_2$)

EXAMPLE 22

4-[2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-benzimidazol-1-yl]-butyrate methyl

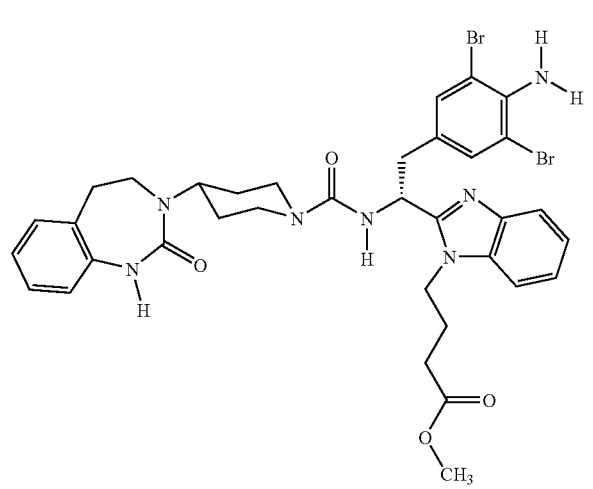

The product was obtained analogously to Example 17 starting from methyl (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and 4-(2-aminophenylamino)-butyrate (Intermediate product 21). The crude product was purified by column chromatography (silica gel, dichloromethane/MeOH/conc. aqueous ammonia 90/10/1 v/v/v) and triturated with diisopropylether.

Yield: 55% of theory $R_f$=0.80 (silica gel, dichloromethane/MeOH/cyclohexane/conc. aqueous ammonia 70/15/15/2 v/v/v/v) ESI-MS: (M+H)$^+$=780/782/784 (Br$_2$)

EXAMPLE 23

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[6-chloro-1-(3-dimethylamino-propyl)-1H-benzimidazol-2-yl]-ethyl}-amide

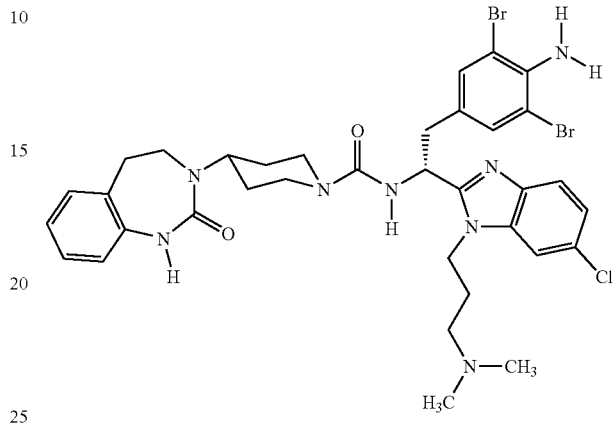

The product was obtained analogously to Example 17 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and 4-chloro-N$^2$-(3-dimethylamino-propyl)-benzene-1,2-diamine (Intermediate product 22). After being purified by column chromatography (silica gel, dichloromethane/MeOH/conc. aqueous ammonia 90/10/1 v/v/v) and triturated with diisopropylether the crude product was isolated as the p-toluenesulphonic acid salt.

Yield: 27% of theory $R_f$=0.61 (silica gel, dichloromethane/MeOH/cyclohexane/conc. aqueous ammonia 70/15/15/2 v/v/v/v) ESI-MS: (M+H)$^+$=799/781/783/785 (Br$_2$Cl)

EXAMPLE 24

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[1-(3-dimethylamino-propyl)-6-fluoro-1H-benzimidazol-2-yl]-ethyl}-amide

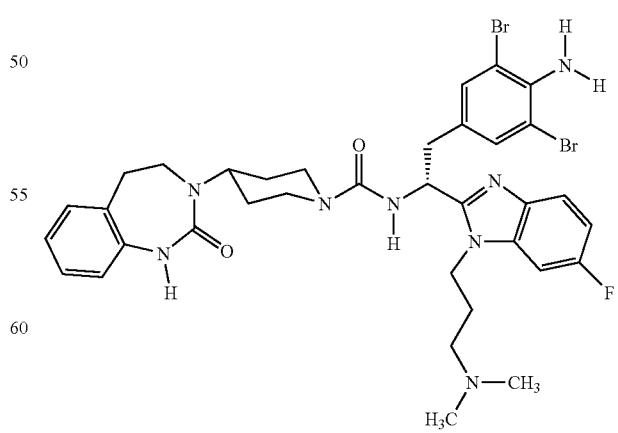

The product was obtained analogously to Example 17 starting from (R)-3-(4-amino-3,5-dibromo-phenyl)-2-{[4-

(2-oxo-1,2,4,5-tetrahydro-1,3-benzodiazepin-3-yl)-piperidin-1-carbonyl]-amino}-propionic acid and N²-(3-dimethylamino-propyl)-4-fluoro-benzene-1,2-diamine (Intermediate product 23). After being purified by column chromatography (silica gel, dichloromethane/MeOH/conc. aqueous ammonia 90/10/1 v/v/v) and triturated with diisopropylether the crude product was isolated as the p-toluenesulphonic acid salt.

Yield: 13% of theory $R_f$=0.18 (silica gel, dichloromethane/MeOH/cyclohexane/conc. aqueous ammonia 70/15/15/2 v/v/v/v) ESI-MS: $(M+H)^+$=783/785/787 (Br$_2$)

EXAMPLE 25

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[1-(3-dimethylamino-propyl)-5-fluoro-1H-benzimidazol-2-yl]-ethyl}-amide

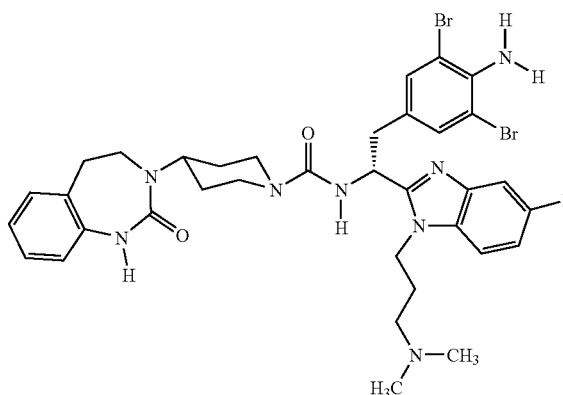

The product was obtained analogously to Example 17 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and N¹-(3-dimethylamino-propyl)-4-fluoro-benzene-1,2-diamine (Intermediate product 24). After being purified by column chromatography (silica gel, dichloromethane/MeOH/conc. aqueous ammonia 90/10/1 v/v/v) and triturated with diisopropylether the crude product was isolated as the p-toluenesulphonic acid salt.

Yield: 57% of theory $R_f$=0.45 (silica gel, dichloromethane/MeOH/cyclohexane/conc. aqueous ammonia 70/15/15/2 v/v/v/v) ESI-MS: $(M+H)^+$=783/785/787 (Br$_2$)

EXAMPLE 26

4-(2-Oxo-1,2,4,5-tetrahydro-1,3-benzodiazepin-3-yl)-piperidin-1-carboxylic acid-{(R)-2-(4-amino-3,5-dibromo-phenyl)-1-[5,6-dichloro-1-(3-dimethylamino-propyl)-1H-benzimidazol-2-yl]-ethyl}-amide

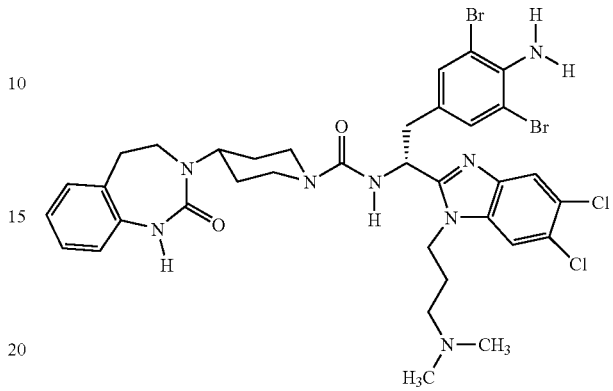

The product was obtained analogously to Example 17 starting from (R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionic acid and 4,5-dichloro-N-(3-dimethylamino-propyl)-benzene-1,2-diamine (Intermediate product 25). After being purified by column chromatography (silica gel, dichloromethane/MeOH/conc. aqueous ammonia 90/10/1 v/v/v) and triturated with diisopropylether the crude product was isolated as the p-toluenesulphonic acid salt.

Yield: 18% of theory $R_f$=0.31 (silica gel, dichloromethane/MeOH/cyclohexane/conc. aqueous ammonia 70/15/15/2 v/v/v/v) ESI-MS: $(M+H)^+$=833/835/837/839/841 (Br$_2$Cl$_2$)

EXAMPLE 27

Methyl-2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylate

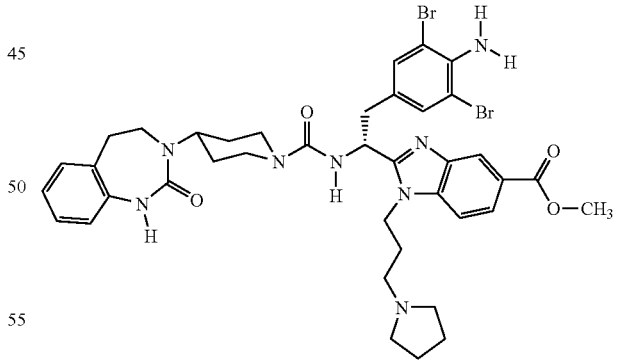

A solution of 1.00 g (1.151 mmol) methyl 3-((R)-3-(4-amino-3,5-dibromo-phenyl)-2-{[4-(2-oxo-1,2,4,5-tetrahydro-1,3-benzodiazepin-3-yl)-piperidin-1-carbonyl]-amino}-propionylamino)-4-(3-pyrrolidin-1-yl-propylamino)-benzoate (Intermediate product 14) in 20 mL glacial acetic acid was refluxed for 2 hours and then the solvent was evaporated i. vac. The crude product was purified by column chromatography (silica gel, dichloromethane/MeOH/conc. aqueous ammonia 90/10/1 v/v/v) and triturated with diisopropyl ether.

Yield: 410 mg (42% of theory) $R_f$=0.39 (silica gel, dichloromethane/MeOH/cyclohexane/conc. aqueous ammonia 70/15/15/2 v/v/v/v) ESI-MS: (M+H)$^+$=849/851/853 (Br$_2$)

EXAMPLE 28

2-(2-(4-Amino-3-chloro-5-trifluoromethyl-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylic acid

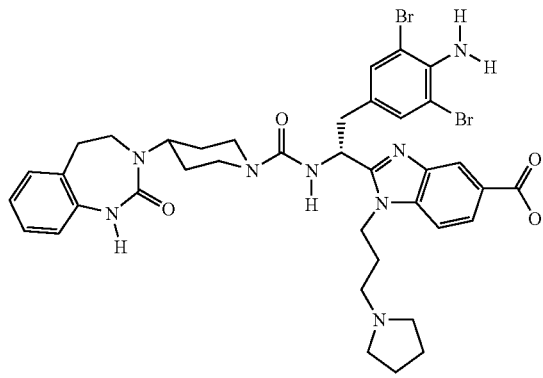

To a solution of 320 mg (0.376 mmol) methyl 2-((R)-2-(4-amino-3,5-dibromo-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylate (Example 27) in 20 mL THF was added at RT a solution of 64 mg (1.525 mmol) lithium hydroxide-monohydrate in 2 mL water and the mixture was stirred for 2 days at RT. The organic solvent was evaporated off i. vac. and the aqueous residue was washed with dichloromethane. The aqueous phase was acidified to pH 2 with 1 M aqueous HCl, the product precipitated was filtered off and dried i. vac.

Yield: 240 mg (76% of theory) $R_f$=0.28 (silica gel, dichloromethane/MeOH/cyclohexane/conc. aqueous ammonia 70/15/15/2 v/v/v/v) ESI-MS: (M+H)$^+$=835/837/839 (Br$_2$)

EXAMPLE 29

4-(2-Oxo-1,2,4,5-tetrahydro-1,3-benzodiazepin-3-yl)-piperidin-1-carboxylic acid-{(R)-2-(3,5-dibromo-4-hydroxy-phenyl)-1-[1-(1-methyl-piperidin-4-ylmethyl)-1H-benzimidazol-2-yl]-ethyl}-amide

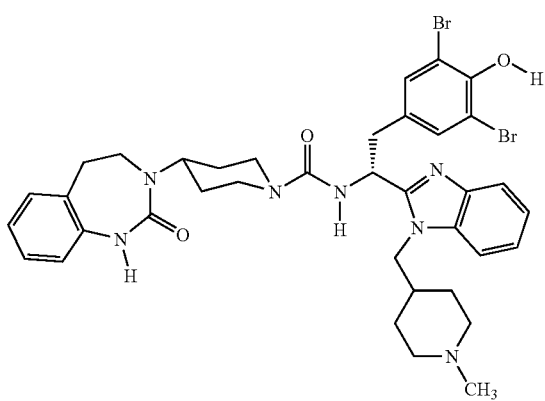

To a solution of 500 mg (0.819 mmol) (R)-3-(3,5-dibromo-4-hydroxy-phenyl)-2-{[4-(2-oxo-1,2,4,5-tetrahydro-1,3-benzodiazepin-3-yl)-piperidin-1-carbonyl]-amino}-propionic acid, 321 mg (1.000 mmol) TBTU and 0.277 mL (2.000 mmol) triethylamine in 10 mL DMF was added 197 mg (0.900 mmol) N-(1-methyl-piperidin-4-ylmethyl)-benzene-1,2-diamine (Intermediate product 17) and the mixture was stirred for 16 hours at RT. The reaction mixture was poured onto 150 mL of sat. aqueous sodium bicarbonate solution and stirred for 15 minutes at RT. The precipitate formed was filtered off, washed with water and dried i. vac. The intermediate product was dissolved in 30 mL dioxane and 5 mL isopropanol, 10 mg of p-toluenesulphonic acid were added and the mixture was heated to 115° C. for 40 minutes. The solvent was evaporated off i. vac., the residue taken up in dichloromethane and the org. phase washed with 15% aqueous potassium carbonate solution. The org. phase was dried over sodium sulphate and evaporated down i. vac. The residue was purified by HPLC-MS (Zorbax Bonus C18 amide-phase 5 μm, gradient 0.15% formic acid in water/acetonitrile 10/90→90/10 v/v) and the product was lyophilised.

Yield: 36 mg (6% of theory) EI-MS: M$^+$=792/794/796 (Br$_2$)

EXAMPLE 30

4-(2-Oxo-1,2,4,5-tetrahydro-1,3-benzodiazepin-3-yl)-piperidin-1-carboxylic acid-{(R)-2-(3,5-dibromo-4-hydroxy-phenyl)-1-[1-(1-methyl-piperidin-4-yl)-1H-benzimidazol-2-yl]-ethyl}-amide

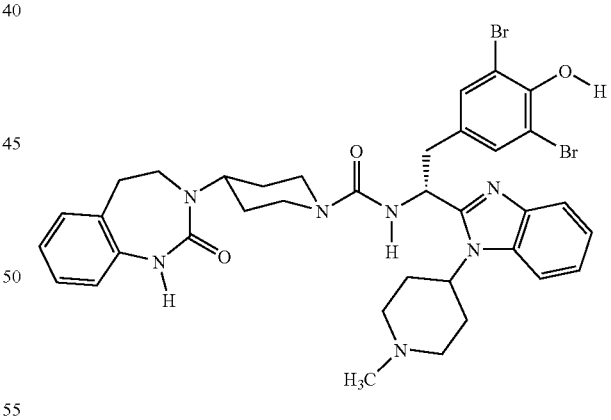

The product was obtained analogously to Example 29 starting from (R)-3-(3,5-dibromo-4-hydroxy-phenyl)-2-{[4-(2-oxo-1,2,4,5-tetrahydro-1,3-benzodiazepin-3-yl)-piperidin-1-carbonyl]-amino}-propionic acid and N-(1-methyl-piperidin-4-yl)-benzene-1,2-diamine (Intermediate product 19).

Yield: 24 mg (4% of theory) EI-MS: M$^+$=778/780/782 (Br$_2$)

EXAMPLE 31

4-(2-Oxo-1,2,4,5-tetrahydro-1,3-benzodiazepin-3-yl)-piperidin-1-carboxylic acid-{(R)-2-(3,5-dibromo-4-hydroxy-phenyl)-1-[1-(3-dimethylamino-propyl)-1H-benzimidazol-2-yl]-ethyl}-amide

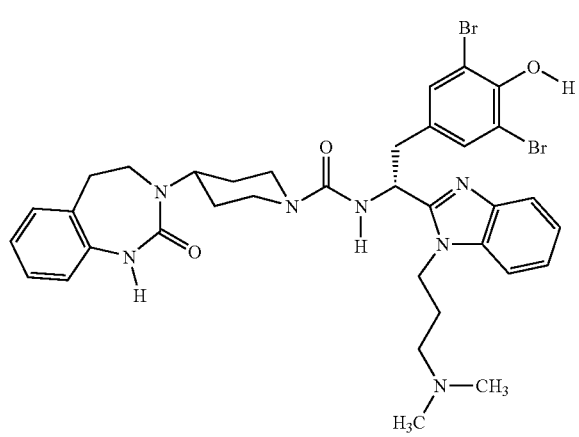

The product was obtained analogously to Example 29 starting from (R)-3-(3,5-dibromo-4-hydroxy-phenyl)-2-{[4-(2-oxo-1,2,4,5-tetrahydro-1,3-benzodiazepin-3-yl)-piperidin-1-carbonyl]-amino}-propionic acid and N-(3-dimethylamino-propyl)-benzene-1,2-diamine.

Yield: 42 mg (7% of theory) EI-MS: $M^+=766/768/770$ ($Br_2$)

EXAMPLE 32

4-(2-Oxo-1,2,4,5-tetrahydro-1,3-benzodiazepin-3-yl)-piperidin-1-carboxylic acid-{(R)-2-(3,5-dibromo-4-hydroxy-phenyl)-1-[1-(3-pyrrolidin-1-yl-propyl)-1H-benzimidazol-2-yl]-ethyl}-amide

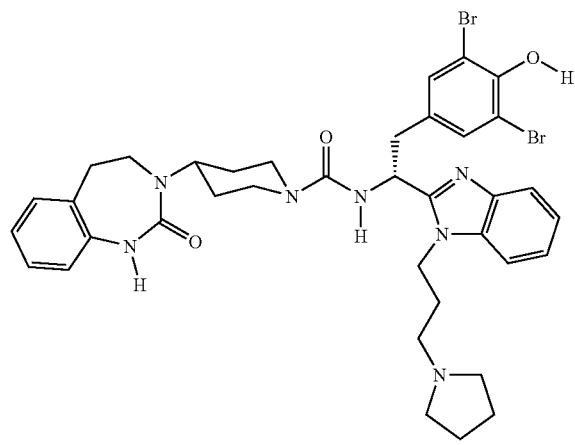

The product was obtained analogously to Example 29 starting from (R)-3-(3,5-dibromo-4-hydroxy-phenyl)-2-{[4-(2-oxo-1,2,4,5-tetrahydro-1,3-benzodiazepin-3-yl)-piperidin-1-carbonyl]-amino}-propionic acid and N-(3-pyrrolidin-1-yl-propyl)-benzene-1,2-diamine (Intermediate product 15).

Yield: 21 mg (3% of theory) EI-MS: $M^+=792/794/796$ ($Br_2$)

EXAMPLE 33

4-(2-Oxo-1,2,4,5-tetrahydro-1,3-benzodiazepin-3-yl)-piperidin-1-carboxylic acid-[1-[6-chloro-1-(3-dimethylamino-propyl)-1H-benzimidazol-2-yl]-2-(3,4-dibromo-phenyl)-ethyl]-amide

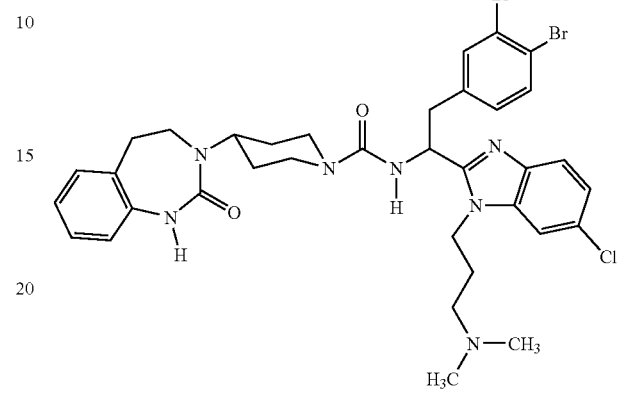

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and 4-chloro-$N^2$-(3-dimethylamino-propyl)-benzene-1,2-diamine (Intermediate product 22). The crude product was purified by column chromatography (silica gel, dichloromethane/MeOH/conc. aqueous ammonia 90/10/1 v/v/v) and triturated with diisopropyl ether.

Yield: 30% of theory ESI-MS: $(M+H)^+=784/786/788$ ($Br_2$)

EXAMPLE 34

4-(2-Oxo-1,2,4,5-tetrahydro-1,3-benzodiazepin-3-yl)-piperidin-1-carboxylic acid-{2-(3,4-dibromo-phenyl)-1-[5,6-dichloro-1-(3-dimethylamino-propyl)-1H-benzimidazol-2-yl]-ethyl}-amide

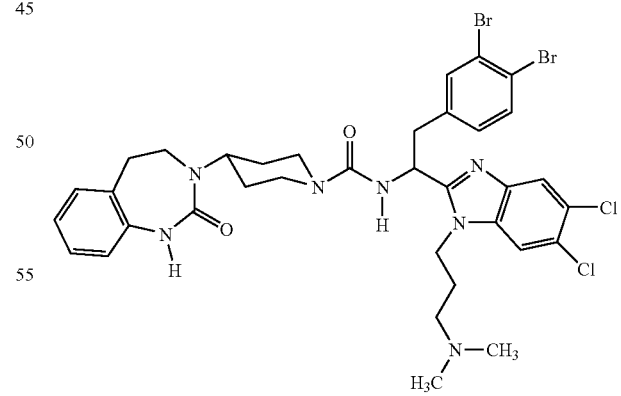

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and 4,5-dichloro-N-(3-dimethylamino-propyl)-benzene-1,2-diamine (Intermediate product 25). The crude product was purified by column chromatography (silica gel, dichloromethane/

MeOH/conc. aqueous ammonia 90/10/1 v/v/v) purified and triturated with diisopropyl ether.

Yield: 7% of theory ESI-MS: (M+H)$^+$=818/820/822/824/826 (Br$_2$Cl$_2$)

EXAMPLE 35

4-(2-Oxo-1,2,4,5-tetrahydro-1,3-benzodiazepin-3-yl)-piperidin-1-carboxylic acid-[1-[7-chloro-1-(3-dimethylamino-propyl)-1H-benzimidazol-2-yl]-2-(3, 4-dibromo-phenyl)-ethyl]-amide

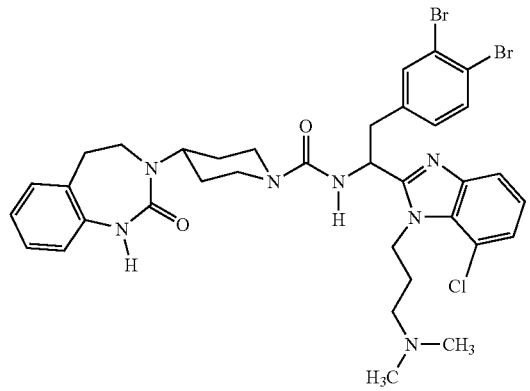

The product was obtained analogously to Example 17 starting from 3-(3,4-dibromo-phenyl )-2-{[4-(2-oxo-1,2,4,5-tetrahydro-1,3-benzodiazepin-3-yl)-piperidin-1-carbonyl]-amino}-propionic acid (Intermediate product 45) and 3-chloro-N$^2$-(3-dimethylamino-propyl)-benzene-1,2-diamine (Intermediate product 27). The crude product was purified by column chromatography (silica gel, dichloromethane/MeOH/conc. aqueous ammonia 90/10/1 v/v/v) purified and triturated with diisopropyl ether.

Yield: 15% of theory ESI-MS: (M+H)$^+$=784/786/788/790 (Br$_2$Cl)

EXAMPLE 36

4-(2-Oxo-1,2,4,5-tetrahydro-1,3-benzodiazepin-3-yl)-piperidin-1-carboxylic acid-{2-(3,4-dibromo-phenyl)-1-[1-(3-dimethylamino-propyl)-6-fluoro-1H-benzimidazol-2-yl]-ethyl}-amide

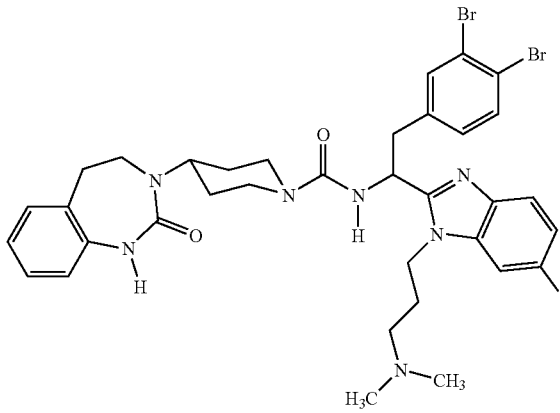

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and N$^2$-(3-dimethylamino-propyl)-4-fluoro-benzene-1,2-diamine (Intermediate product 23). The crude product was purified by column chromatography (silica gel, dichloromethane/MeOH/conc. aqueous ammonia 90/10/1 v/v/v) purified and triturated with diisopropylether.

Yield: 19% of theory ESI-MS: (M+H)$^+$=768/770/72 (Br$_2$)

EXAMPLE 37

4-(2-Oxo-1,2,4,5-tetrahydro-1,3-benzodiazepin-3-yl)-piperidin-1-carboxylic acid-{2-(3,4-dibromo-phenyl)-1-[1-(1-methyl-piperidin-4-yl)-1H-benzimidazol-2-yl]-ethyl}-amide

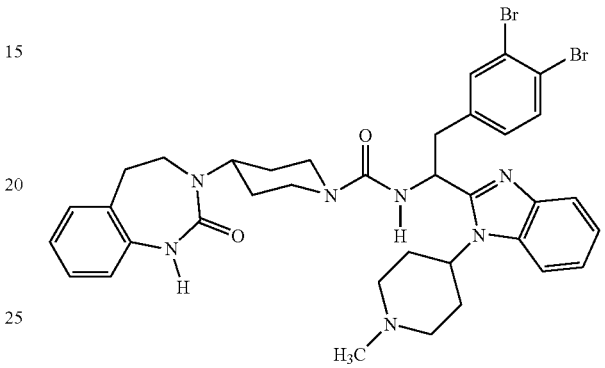

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and N-(1-methyl-piperidin-4-yl)-benzene-1,2-diamine (Intermediate product 19). The crude product was purified by column chromatography (silica gel, dichloromethane/MeOH/conc. aqueous ammonia 90/10/1 v/v/v) and triturated with diisopropylether.

Yield: 19% of theory ESI-MS: (M+H)$^+$=762/764/766 (Br$_2$)

EXAMPLE 38

4-(2-Oxo-1,2,4,5-tetrahydro-1,3-benzodiazepin-3-yl)-piperidin-1-carboxylic acid-{2-(3,4-dibromo-phenyl)-1-[1-(3-pyrrolidin-1-yl-propyl)-1H-benzimidazol-2-yl]-ethyl}-amide

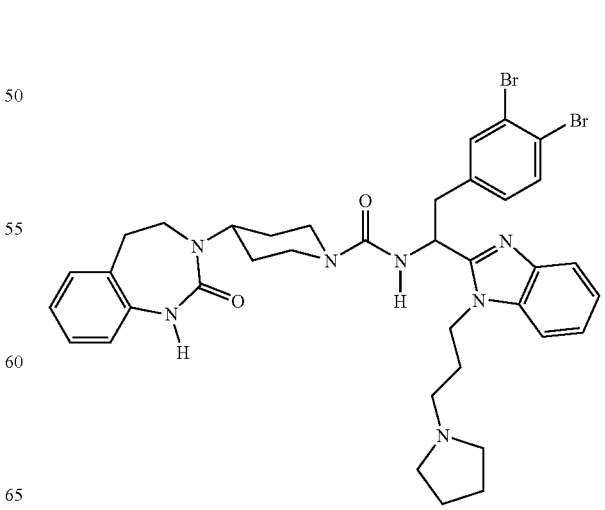

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and N-(3-pyrrolidin-1-yl-propyl)-benzene-1,2-diamine (Intermediate product 15). The crude product was purified by column chromatography (silica gel, dichloromethane/MeOH/conc. aqueous ammonia 90/10/1 v/v/v) and triturated with diisopropylether.

Yield: 19% of theory ESI-MS: (M+H)⁺=776/778/780 (Br₂)

EXAMPLE 39

4-(2-Oxo-1,2,4,5-tetrahydro-1,3-benzodiazepin-3-yl)-piperidin-1-carboxylic acid-{2-(3,4-dibromo-phenyl)-1-[1-(1-methyl-piperidin-4-ylmethyl)-1H-benzimidazol-2-yl]-5 ethyl}-amide

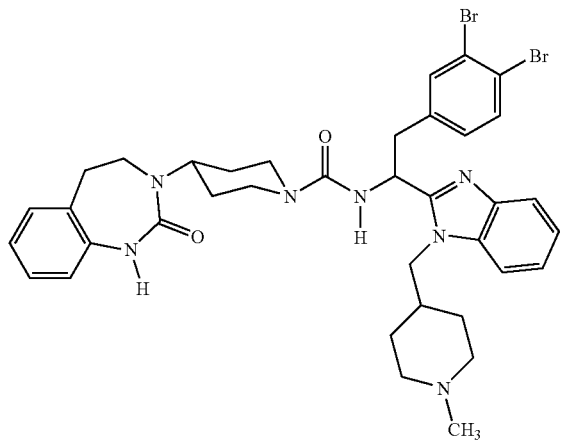

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and N-(1-methyl-piperidin-4-ylmethyl)-benzene-1,2-diamine (Intermediate product 19). The crude product was purified by column chromatography (silica gel, dichloromethane/MeOH/conc. aqueous ammonia 90/10/1 v/v/v) purified and triturated with diisopropyl ether.

Yield: 11% of theory ESI-MS: (M+H)⁺=776/778/780 (Br₂)

EXAMPLE 40

4-(2-Oxo-1,2,4,5-tetrahydro-1,3-benzodiazepin-3-yl)-piperidin-1-carboxylic acid-[2-(3,4-dibromo-phenyl)-1-(1-pyridin-3-ylmethyl-1H-benzimidazol-2-yl)-ethyl]-amide

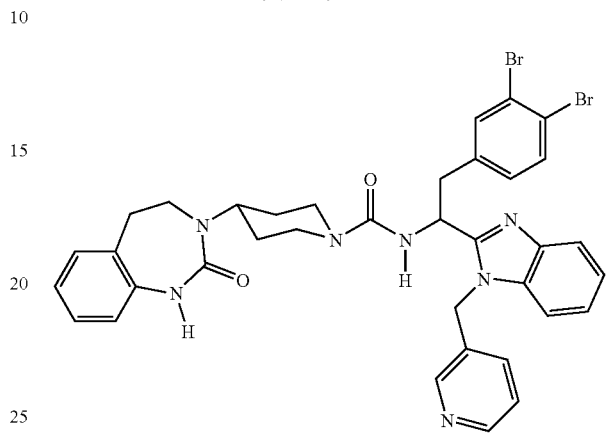

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and N-pyridin-3-ylmethyl-benzene-1,2-diamine (Intermediate product 16). The crude product was purified by column chromatography (silica gel, dichloromethane/MeOH/conc. aqueous ammonia 90/10/1 v/v/v) purified and triturated with diisopropyl ether.

Yield: 12% of theory ESI-MS: (M+H)⁺=756/758/760 (Br₂)

EXAMPLE 41

4-(2-Oxo-1,2,4,5-tetrahydro-1,3-benzodiazepin-3-yl)-piperidin-1-carboxylic acid-{2-(3,4-dibromo-phenyl)-1-[1-(3-dimethylamino-propyl)-1H-benzimidazol-2-yl]-ethyl}-amide

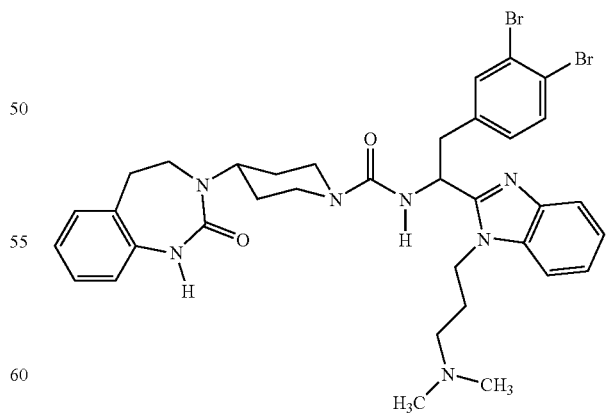

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and N-(3-dimethylamino-propyl)-benzene-1,2-diamine. The crude product was purified by column chromatography (silica gel, dichloromethane/MeOH/conc. aqueous ammonia 90/10/1 v/v/v) purified and triturated with diisopropyl ether.

Yield: 20% of theory ESI-MS: (M+H)⁺=750/752/754 (Br₂)

EXAMPLE 42

4-(2-Oxo-1,2,4,5-tetrahydro-1,3-benzodiazepin-3-yl)-piperidin-1-carboxylic acid-{2-(3,4-dibromo-phenyl)-1-[1-(4-dimethylamino-butyl)-1H-benzimidazol-2-yl]-ethyl}-amide

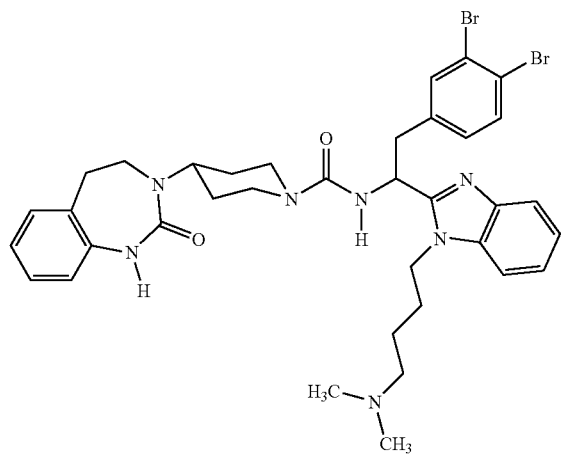

The product was obtained analogously to Example 17 starting from 3-(3,4-dibromo-phenyl)-2-{[4-(2-oxo-1,2,4,5-tetrahydro-1,3-benzodiazepin-3-yl)-piperidin-1-carbonyl]-amino}-propionic acid (Intermediate product 45) and N-(3-dimethylamino-butyl)-benzene-1,2-diamine (Intermediate product 18). The crude product was purified by column chromatography (silica gel, dichloromethane/MeOH/conc. aqueous ammonia 90/10/1 v/v/v) purified and triturated with diisopropyl ether.

Yield: 16% of theory ESI-MS: (M+H)⁺=764/766/768 (Br₂)

EXAMPLE 43

4-(2-Oxo-1,2,4,5-tetrahydro-1,3-benzodiazepin-3-yl)-piperidin-1-carboxylic acid-{2-(3,4-diethyl-phenyl)-1-[1-(3-dimethylamino-propyl)-1H-benzimidazol-2-yl]-ethyl}-amide

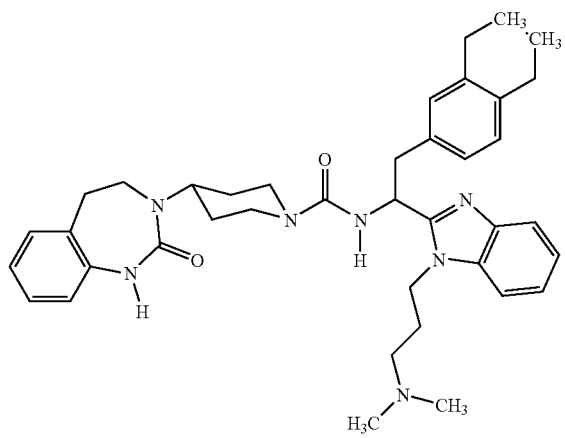

To a solution of 150 mg (0.304 mmol) 3-(3,4-diethyl-phenyl)-2-{[4-(2-oxo-1,2,4,5-tetrahydro-1,3-benzodiazepin-3-yl)-piperidin-1-carbonyl]-amino}-propionic acid (Intermediate product 50), 105 mg (0.327 mmol) TBTU and 44 mg (0.326 mmol) HOBt in 50 mL THF was added 58 µL (0.327 mmol) Hünig base and the mixture was stirred for 30 minutes at RT. 60 mg (0.310 mmol) of N-(3-dimethylamino-propyl)-benzene-1,2-diamine was added and the mixture was stirred for 16 hours at RT. The solvent was evaporated i. vac., the residue taken up in dichloromethane and the org. phase washed with sat. aqueous sodium bicarbonate solution. The org. phase was dried over sodium sulphate and evaporated i. vac. 30 mL dioxane and 100 mg p-toluenesulphonic acid was added and the mixture was refluxed for 15 minutes. The solvent was evaporated off i. vac. and dichloromethane was added. The org. phase was washed with sat. aqueous sodium bicarbonate solution, dried over sodium sulphate and evaporated i. vac. Purification by HPLC-MS (Zorbax Bonus C18 amide-phase 5 pm, gradient 0.15% formic acid in water/acetonitrile 10/90→90/10 v/v) yielded the product.

Yield: 80 mg (40% of theory) R_f=0.51 (silica gel, dichloromethane/MeOH/cyclohexane/conc. aqueous ammonia 70/15/15/2 v/v/v/v) ESI-MS: (M+H)⁺=650

EXAMPLE 44

4-(2-Oxo-1,2,4,5-tetrahydro-1,3-benzodiazepin-3-yl)-piperidin-1-carboxylic acid-{2-(3,4-diethyl-phenyl)-1-[1-(4-dimethylamino-butyl)-1H-benzimidazol-2-yl]-ethyl}-amide

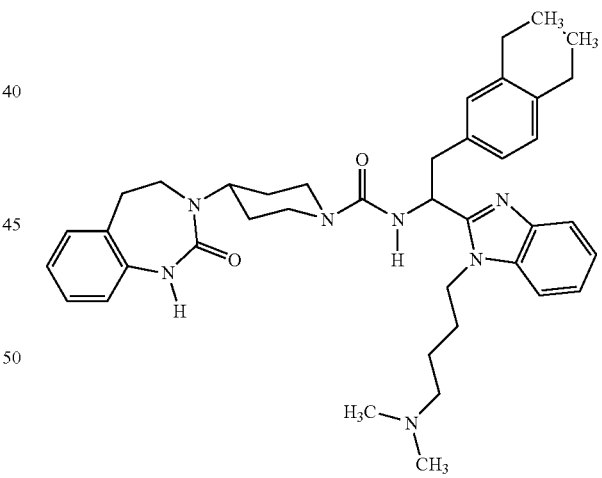

The product was obtained analogously to Example 17 starting from 3-(3,4-diethyl-phenyl)-2-{[4-(2-oxo-1,2,4,5-tetrahydro-1,3-benzodiazepin-3-yl)-piperidin-1-carbonyl]-amino}-propionic acid (Intermediate product 50) and N-(3-dimethylamino-butyl)-benzene-1,2-diamine (Intermediate product 18). The crude product was purified by column chromatography (silica gel, dichloromethane/MeOH/conc. aqueous ammonia 90/10/1 v/v/v) and triturated with diisopropyl ether.

Yield: 29% of theory ESI-MS: (M+H)⁺=664

EXAMPLE 45

4-(2-Oxo-1,2,4,5-tetrahydro-1,3-benzodiazepin-3-yl)-piperidin-1-carboxylic acid-{2-(3,4-diethyl-phenyl)-1-[1-(1-methyl-piperidin-4-yl)-1H-benzimidazol-2-yl]-ethyl}-amide

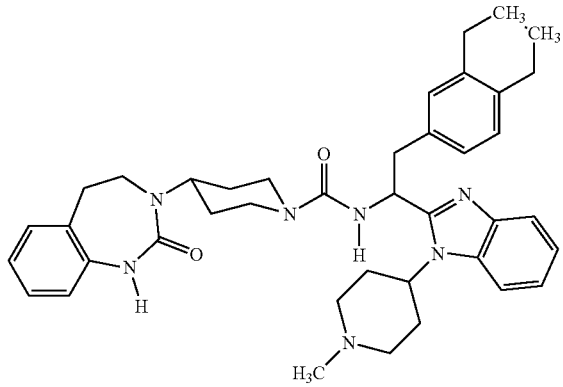

The product was obtained analogously to Example 17 starting from 3-(3,4-diethyl-phenyl)-2-{[4-(2-oxo-1,2,4,5-tetrahydro-1,3-benzodiazepin-3-yl)-piperidin-1-carbonyl]-amino}-propionic acid (Intermediate product 50) and N-(1-methyl-piperidin-4-yl)-benzene-1,2-diamine (Intermediate product 19). The crude product was purified by column chromatography (silica gel, dichloromethane/MeOH/conc. aqueous ammonia 90/10/1 v/v/v) and triturated with diisopropyl ether.

Yield: 6% of theory ESI-MS: $(M+H)^+=662$

EXAMPLE 46

4-(2-Oxo-1,2,4,5-tetrahydro-1,3-benzodiazepin-3-yl)-piperidin-1-carboxylic acid-{2-(3,4-diethyl-phenyl)-1-[1-(3-pyrrolidin-1-yl-propyl)-1H-benzimidazol-2-yl]-ethyl}-amide

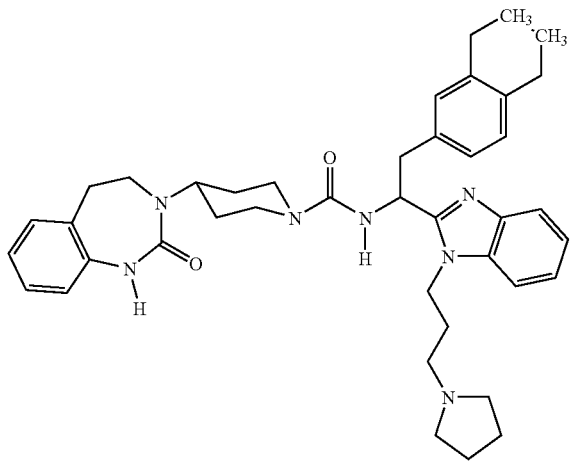

The product was obtained analogously to Example 17 starting from 3-(3,4-diethyl-phenyl)-2-{[4-(2-oxo-1,2,4,5-tetrahydro-1,3-benzodiazepin-3-yl)-piperidin-1-carbonyl]-amino}-propionic acid (Intermediate product 50) and N-(3-pyrrolidin-1-yl-propyl)-benzene-1,2-diamine (Intermediate product 15). The crude product was purified by column chromatography (silica gel, dichloromethane/MeOH/conc. aqueous ammonia 90/10/1 v/v/v) and triturated with diisopropyl ether.

Yield: 16% of theory ESI-MS: $(M+H)^+=676$

EXAMPLE 47

4-(2-Oxo-1,2,4,5-tetrahydro-1,3-benzodiazepin-3-yl)-piperidin-1-carboxylic acid-{2-(3,4-diethyl-phenyl)-1-[1-(1-methyl-piperidin-4-ylmethyl)-1H-benzimidazol-2-yl]-ethyl}-amide

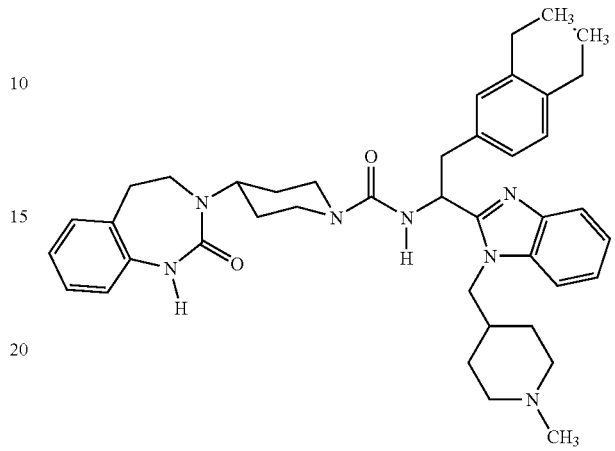

The product was obtained analogously to Example 17 starting from 3-(3,4-diethyl-phenyl)-2-{[4-(2-oxo-1,2,4,5-tetrahydro-1,3-benzodiazepin-3-yl)-piperidin-1-carbonyl]-amino}-propionic acid (Intermediate product 50) and N-(1-methyl-piperidin-4-ylmethyl)-benzene-1,2-diamine (Intermediate product 17). The crude product was purified by column chromatography (silica gel, dichloromethane/MeOH/conc. aqueous ammonia 90/10/1 v/v/v) and triturated with diisopropyl ether.

Yield: 28% of theory ESI-MS: $(M+H)^+=676$

EXAMPLE 48

4-(2-Oxo-1,2,4,5-tetrahydro-1,3-benzodiazepin-3-yl)-piperidin-1-carboxylic acid-[2-(3,4-diethyl-phenyl)-1-(1-pyridin-3-ylmethyl-1H-benzimidazol-2-yl)-ethyl]-amide

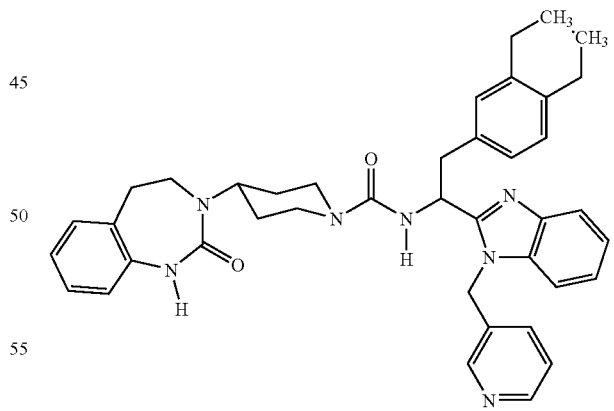

The product was obtained analogously to Example 17 starting from 3-(3,4-diethyl-phenyl)-2-{[4-(2-oxo-1,2,4,5-tetrahydro-1,3-benzodiazepin-3-yl)-piperidin-1-carbonyl]-amino}-propionic acid (Intermediate product 50) and N-pyridin-3-ylmethyl-benzene-1,2-diamine (Intermediate product 16). The crude product was purified by column chromatography (silica gel, dichloromethane/MeOH/conc. aqueous ammonia 90/10/1 v/v/v) and triturated with diisopropyl ether.

Yield: 17% of theory ESI-MS: $(M+H)^+=656$

EXAMPLE 49

4-(2-Oxo-1,2,4,5-tetrahydro-1,3-benzodiazepin-3-yl)-piperidin-1-carboxylic acid-{2-(3,5-bis-trifluoromethyl-phenyl)-1-[1-(1-methyl-piperidin-4-yl)-1H-benzimidazol-2-yl]-ethyl}-amide

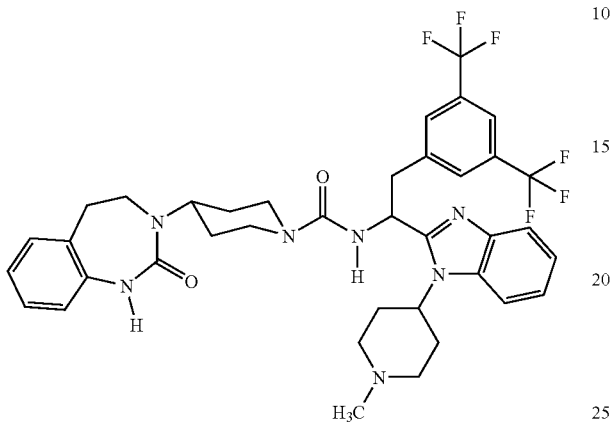

The product was obtained analogously to Example 17 starting from 3-(3,5-bis-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 53) and N-(1-methyl-piperidin-4-yl)-benzene-1,2-diamine (Intermediate product 19). The crude product was purified by column chromatography (silica gel, dichloromethane/MeOH/conc. aqueous ammonia 90/10/1 v/v/v) and triturated with petroleum ether.

Yield: 8% of theory ESI-MS: (M+H)$^+$=742

EXAMPLE 50

4-(2-Oxo-1,2,4,5-tetrahydro-1,3-benzodiazepin-3-yl)-piperidin-1-carboxylic acid-{2-(3,5-bis-trifluoromethyl-phenyl)-1-[1-(3-pyrrolidin-1-yl-propyl)-1H-benzimidazol-2-yl]-ethyl}-amide

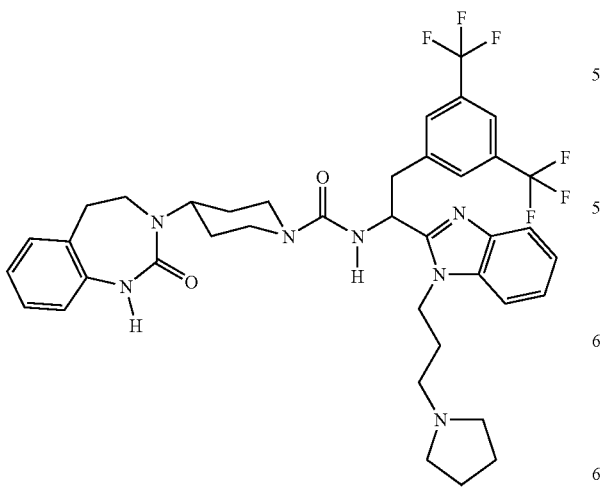

The product was obtained analogously to Example 17 starting from 3-(3,5-bis-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 53) and N-(3-pyrrolidin-1-yl-propyl)-benzene-1,2-diamine (Intermediate product 15). The crude product was purified by column chromatography (silica gel, dichloromethane/MeOH/conc. aqueous ammonia 90/10/1 v/v/v) and triturated with petroleum ether.

Yield: 11% of theory ESI-MS: (M+H)$^+$=756

EXAMPLE 51

4-(2-Oxo-1,2,4,5-tetrahydro-1,3-benzodiazepin-3-yl)-piperidin-1-carboxylic acid-{2-(3,5-bis-trifluoromethyl-phenyl)-1-[1-(1-methyl-piperidin-4-ylmethyl)-1H-benzimidazol-2-yl]-ethyl}-amide

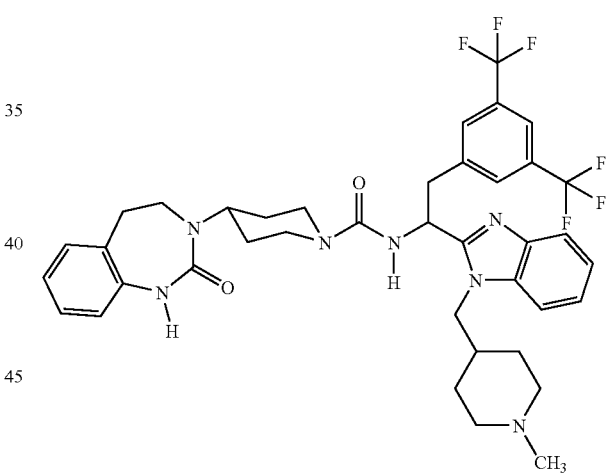

The product was obtained analogously to Example 17 starting from 3-(3,5-bis-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 53) and N-(1-methyl-piperidin-4-ylmethyl)-benzene-1,2-diamine (Intermediate product 17). The crude product was purified by column chromatography (silica gel, dichloromethane/MeOH/conc. aqueous ammonia 90/10/1 v/v/v) and triturated with petroleum ether.

Yield: 23% of theory ESI-MS: (M+H)$^+$=756

EXAMPLE 52

4-(2-Oxo-1,2,4,5-tetrahydro-1,3-benzodiazepin-3-yl)-piperidin-1-carboxylic acid-{2-(3,5-bis-trifluoromethyl-phenyl)-1-[1-(3-dimethylamino-propyl)-1H-benzimidazol-2-yl]-ethyl}-amide

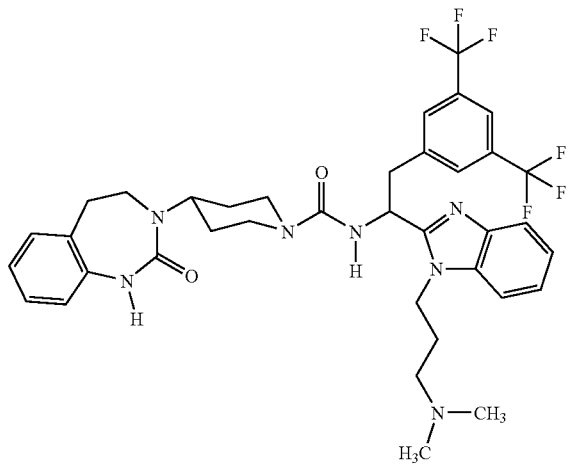

The product was obtained analogously to Example 17 starting from 3-(3,5-bis-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 53) and N-(3-dimethylamino-propyl)-benzene-1,2-diamine. The crude product was purified by column chromatography (silica gel, dichloromethane/MeOH/conc. aqueous ammonia 90/10/1 v/v/v) and triturated with petroleum ether.

Yield: 35% of theory ESI-MS: (M+H)$^+$=730

EXAMPLE 53

Methyl-2-(2-(4-amino-3-chloro-5-trifluoromethyl-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylate

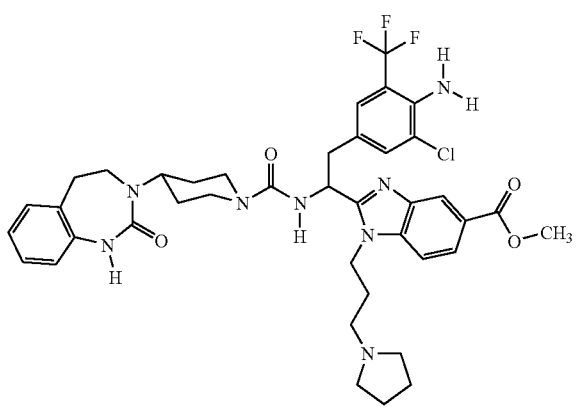

To a solution of 800 mg (1.444 mmol) 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 60) and 500 mg (1.557 mmol) TBTU in 70 mL DMF was added 0.27 mL (1.550 mmol) Hünig base and the mixture was stirred for 30 minutes at RT. 410 mg (1.478 mmol) methyl 3-amino-4-(3-pyrrolidin-1-yl-propylamino)-benzoate (Intermediate product 26) was added and the mixture was stirred for 16 hours at RT. The reaction mixture was evaporated i. vac. and the residue combined with 15% aqueous potassium carbonate solution. The precipitate formed was filtered off and dried i. vac. The precipitate was dissolved in 20 mL glacial acetic acid and refluxed for 2 hours. The solvent was evaporated i. vac. and the crude product purified by column chromatography (silica gel, dichloromethane/MeOH/conc. aqueous ammonia 90/10/1 v/v/v) and triturated with diisopropyl ether.

Yield: 430 mg (41% of theory) $R_f$=0.36 (silica gel, dichloromethane/MeOH/cyclohexane/conc. aqueous ammonia 70/15/15/2 v/v/v/v) ESI-MS: (M+H)$^+$=795/797 (Cl)

EXAMPLE 54

2-(2-(4-Amino-3-chloro-5-trifluoromethyl-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylic acid

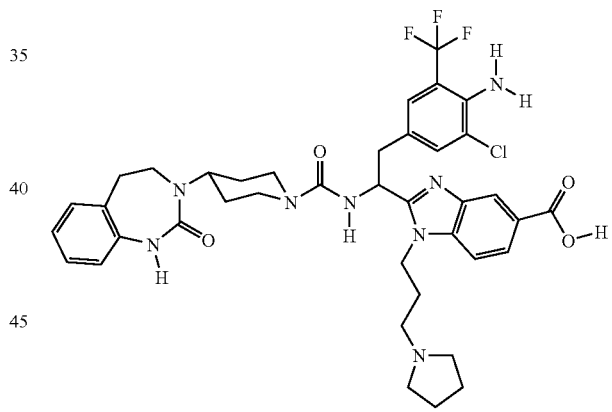

To a solution of 310 mg (0.390 mmol) methyl 2-(2-(4-amino-3-chloro-5-trifluoromethyl-phenyl)-1-{[4-(2-oxo-1,2,4,5-tetrahydro-1,3-benzodiazepin-3-yl)-piperidin-1-carbonyl]-amino}-ethyl)-1-(3-pyrrolidin-1-yl-propyl)-1H-benzimidazole-5-carboxylate (Example 53) in 20 mL THF was added a solution of 72 mg (1.716 mmol) lithium hydroxide-monohydrate in 5 mL water and the mixture was stirred for 2 days at RT. THF was evaporated i. vac., the residue was dissolved in water and 1.7 mL of 1 M aqueous HCl was added. The precipitate formed was filtered off and dried i. vac.

Yield: 190 mg (62% of theory) $R_f$=0.22 (silica gel, dichloromethane/MeOH/cyclohexane/conc. aqueous ammonia 70/15/15/2 v/v/v/v) ESI-MS: (M+H)$^+$=781/783 (Cl)

EXAMPLE 55

4-(2-Oxo-1,2,4,5-tetrahydro-1,3-benzodiazepin-3-yl)-piperidin-1-carboxylic acid-{2-(4-amino-3-chloro-5-trifluoromethyl-phenyl)-1-[1-(1-methyl-piperidin-4-yl)-1H-benzimidazol-2-yl]-ethyl}-amide

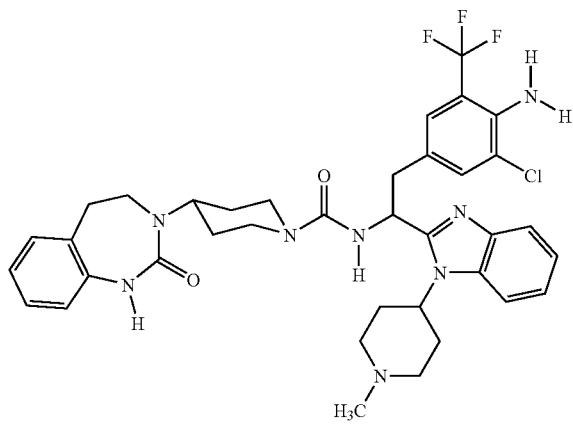

The product was obtained analogously to Example 17 starting from 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 60) and N-(1-methyl-piperidin-4-yl)-benzene-1,2-diamine (Intermediate product 19). The crude product was purified by column chromatography (silica gel, dichloromethane/MeOH/conc. aqueous ammonia 90/10/1 v/v/v) and triturated with petroleum ether.

Yield: 2% of theory ESI-MS: (M+H)$^+$=723/725 (Cl)

EXAMPLE 56

4-(2-Oxo-1,2,4,5-tetrahydro-1,3-benzodiazepin-3-yl)-piperidin-1-carboxylic acid-{2-(4-amino-3-chloro-5-trifluoromethyl-phenyl)-1-[1-(3-pyrrolidin-1-yl-propyl)-1H-benzimidazol-2-yl]-ethyl}-amide

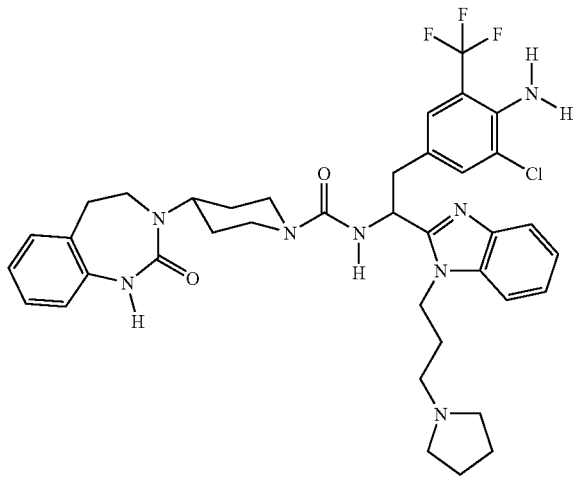

The product was obtained analogously to Example 17 starting from 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 60) and N-(3-pyrrolidin-1-yl-propyl)-benzene-1,2-diamine (Intermediate product 15). The crude product was purified by column chromatography (silica gel, dichloromethane/MeOH/conc. aqueous ammonia 90/10/1 v/v/v) and triturated with petroleum ether.

Yield: 19% of theory ESI-MS: (M+H)$^+$=737/739 (Cl)

EXAMPLE 57

4-(2-Oxo-1,2,4,5-tetrahydro-1,3-benzodiazepin-3-yl)-piperidin-1-carboxylic acid-{2-(4-amino-3-chloro-5-trifluoromethyl-phenyl)-1-[1-(1-methyl-piperidin-4-ylmethyl)-1H-benzimidazol-2-yl]-ethyl}-amide

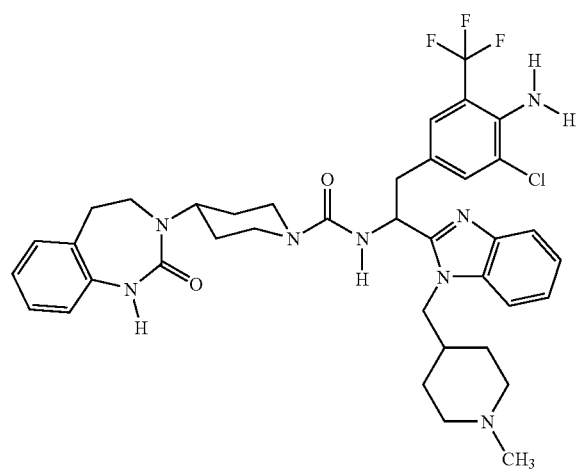

The product was obtained analogously to Example 17 starting from 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 60) and N-(1-methyl-piperidin-4-ylmethyl)-benzene-1,2-diamine (Intermediate product 17). The crude product was purified by column chromatography (silica gel, dichloromethane/MeOH/conc. aqueous ammonia 90/10/1 v/v/v) and triturated with petroleum ether.

Yield: 26% of theory ESI-MS: (M+H)$^+$=737/739 (Cl)

EXAMPLE 58

4-(2-Oxo-1,2,4,5-tetrahydro-1,3-benzodiazepin-3-yl)-piperidin-1-carboxylic acid-[2-(4-amino-3-chloro-5-trifluoromethyl-phenyl)-1-(1-pyridin-3-ylmethyl-1H-benzimidazol-2-yl)-ethyl]-amide

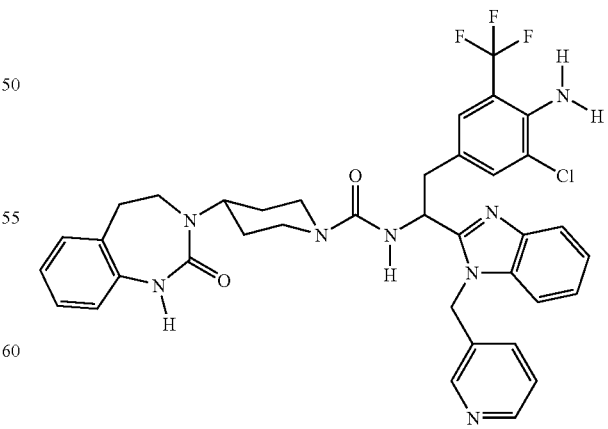

The product was obtained analogously to Example 17 starting from 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 60) and N-pyridin-3-ylmethyl-benzene-1,2-diamine (Intermediate product 16) . The crude product was purified by column chromatography (silica gel, dichloromethane/MeOH/conc. aqueous ammonia 90/10/1 v/v/v) and triturated with petroleum ether.

Yield: 6% of theory ESI-MS: (M+H)$^+$=717/719 (Cl)

EXAMPLE 59

4-(2-Oxo-1,2,4,5-tetrahydro-1,3-benzodiazepin-3-yl)-piperidin-1-carboxylic acid-{2-(4-amino-3-chloro-5-trifluoromethyl-phenyl)-1-[1-(3-dimethylamino-propyl)-1H-benzimidazol-2-yl]-ethyl}-amide

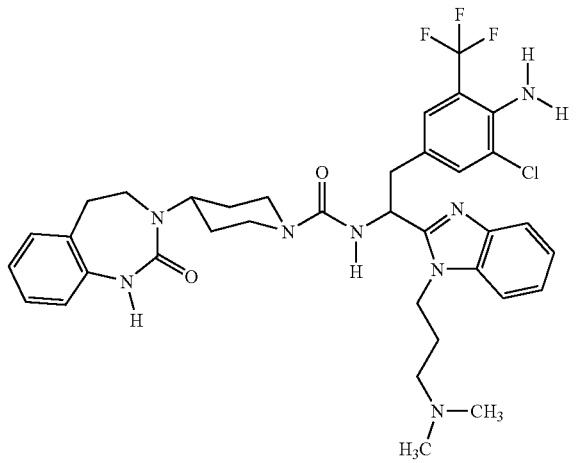

The product was obtained analogously to Example 17 starting from 3-(4-amino-3-chloro-5-trifluoromethyl-phenyl)-2-{[4-(2-oxo-1,2,4,5-tetrahydro-1,3-benzodiazepin-3-yl)-piperidin-1-carbonyl]-amino}-propionic acid (Intermediate product 60) and N-(3-dimethylamino-propyl)-benzene-1,2-diamine. The crude product was purified by column chromatography (silica gel, dichloromethane/MeOH/conc. aqueous ammonia 90/10/1 v/v/v) and triturated with petroleum ether.

Yield: 12% of theory ESI-MS: (M+H)$^+$=711/713 (Cl)

EXAMPLE 60

3-(1-{4-(3,4-Diethyl-phenyl)-3-[1-(3-dimethylamino-propyl)-1H-benzimidazol-2-yl]-butyryl}-piperidin-4-yl)-1,3,4,5-tetrahydro-1,3-benzodiazepin-2-one

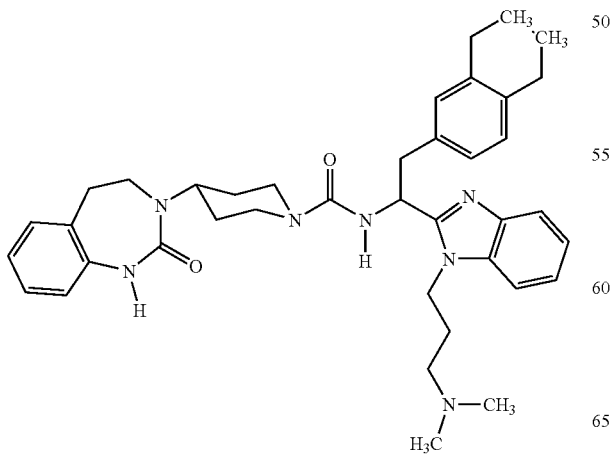

The product was obtained analogously to Example 43 starting from 2-(3,4-diethyl-benzyl)-4-oxo-4-[4-(2-oxo-1,2,4,5-tetrahydro-1,3-benzodiazepin-3-yl)-piperidin-1-yl]-butyric acid (Intermediate product 64) and N-(3-dimethylamino-propyl)-benzene-1,2-diamine. The crude product was purified by HPLC-MS (Zorbax Bonus C18 amide-phase 5 µm, gradient 0.15% formic acid in water/acetonitrile 10/90→90/10 v/v) and then lyophilised.

Yield: 5% of theory R$_f$=0.61 (silica gel, dichloromethane/MeOH/cyclohexane/conc. aqueous ammonia 70/15/15/2 v/v/v/v) ESI-MS: (M+H)$^+$=649

EXAMPLE 61

3-(1-{4-(4-Amino-3-chloro-5-trifluoromethyl-phenyl)-3-[1-(3-pyrrolidin-1-yl-propyl)-1H-benzimidazol-2-yl]-butyryl}-piperidin-4-yl)-1,3,4,5-tetrahydro-1,3-benzodiazepin-2-one

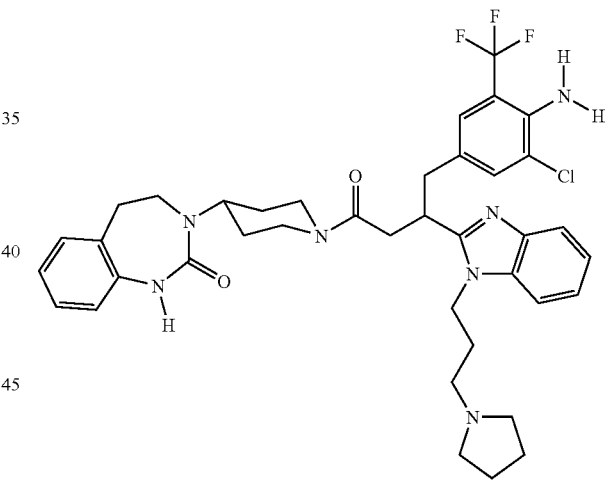

To a solution of 380 mg (0.708 mmol) 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) in 7.5 mL DMF and 0.5 mL water was added 233 mg (0.710 mmol) N-(3-pyrrolidin-1-yl-propyl)-benzene-1,2-diamine-trihydrochloride (Intermediate product 15) and the mixture was stirred at RT for 48 hours in an atmosphere of air. The reaction mixture was evaporated i. vac. and EtOAc was added. The org. phase was washed with sat. aqueous sodium bicarbonate solution, dried over sodium sulphate and evaporated i. vac. The crude product was purified by column chromatography (silica gel, EtOAc/MeOH/sat. aqueous ammonia 90/10/1 v/v/v) and triturated with diisopropyl ether.

Yield: 130 mg (25% of theory) $R_f$=0.17 (silica gel, EtOAc/MeOH/sat. aqueous ammonia 90/10/1 v/v/v) ESI-MS: $(M+H)^+$=736/738 (Cl)

EXAMPLE 62

3-(1-{4-(4-Amino-3-chloro-5-trifluoromethyl-phenyl)-3-[1-(3-imidazol-1-yl-propyl)-1H-benzimidazol-2-yl]-butyryl}-piperidin-4-yl)-1,3,4,5-tetrahydro-1,3-benzodiazepin-2-one

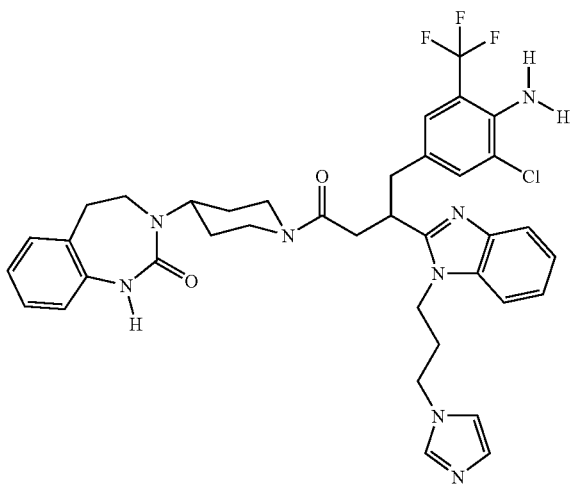

To a solution of 537 mg (1.000 mmol) 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) in 10 mL DMF was added 391 mg (1.200 mmol) N-(3-imidazol-1-yl-propyl)-benzene-1,2-diamine-trihydrochloride (Intermediate product 28) and the mixture was stirred for 16 hours in an atmosphere of air. The reaction mixture was poured into ice water, the precipitate formed was filtered off and washed with water. The crude product was purified using HPLC-MS (Zorbax Bonus C18 amide-phase 5 μm, gradient 0.15% formic acid in water/acetonitrile 10/90→90/10 v/v) and lyophilised.

Yield: 470 mg (64% of theory) ESI-MS: $(M+H)^+$=733/735 (Br$_2$)

EXAMPLE 63

3-(1-{4-(4-Amino-3-chloro-5-trifluoromethyl-phenyl)-3-[5-(3-dimethylamino-propyl)-1-ethyl-1H-benzimidazol-2-yl]-butyryl}-piperidin-4-yl)-1,3,4,5-tetrahydro-1,3-benzodiazepin-2-one

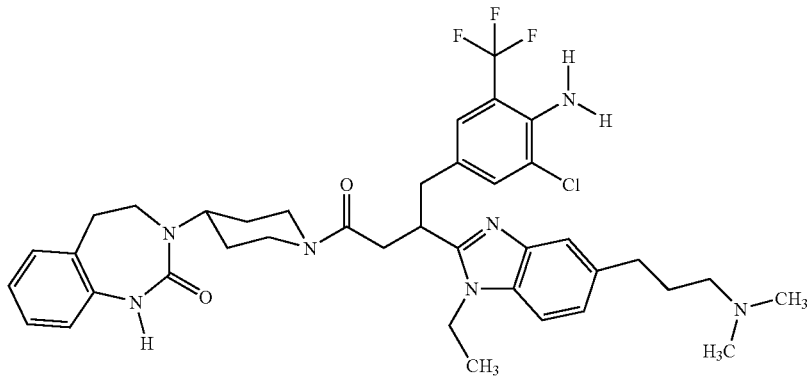

To a solution of 860 mg (1.602 mmol) 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) in 15 mL DMF was added 391 mg (1.200 mmol) 4-(3-dimethylamino-propyl)-N$^1$-ethyl-benzene-1,2-diamine (Intermediate product 29), the mixture was acidified to pH 4-5 with semiconc. aqueous HCl and stirred for 3 hours under an atmosphere of air. The reaction mixture was poured onto saturated. aqueous sodium bicarbonate solution and the precipitate formed was filtered off. The crude product was purified by column chromatography (silica gel, dichloromethane/MeOH/conc. aqueous ammonia 90/10/3 v/v/v).

Yield: 280 mg (24% of theory) $R_f$=0.37 (silica gel, dichloromethane/cyclohexane/MeOH/sat. aqueous ammonia 70/15/15/12 v/v/v/v) ESI-MS: $(M+H)^+$=738/740 (Cl)

EXAMPLE 64

3-(1-{4-(4-Amino-3-chloro-5-trifluoromethyl-phenyl)-3-[1-(3-diethylamino-propyl)-1H-benzimidazol-2-yl]-butyryl}-piperidin-4-yl)-1,3,4,5-tetrahydro-1,3-benzodiazepin-2-one

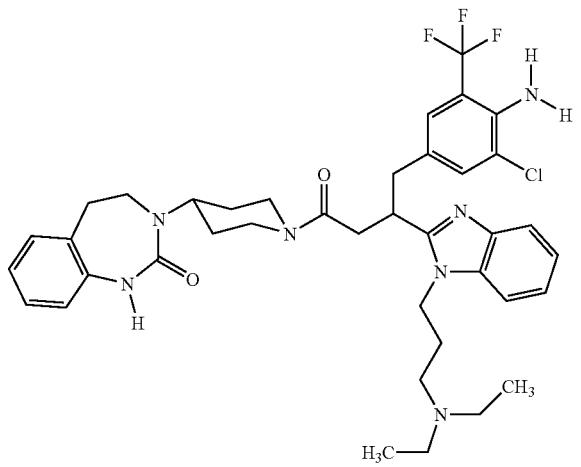

The product was obtained analogously to Example 62 starting from 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) and N-(3-diethylamino-propyl)-benzene-1,2-diamine-trihydrochloride (Intermediate product 39).

Yield: 65% of theory ESI-MS: (M+H)$^+$=738/740 (Cl)

EXAMPLE 65

3-(1-{4-(4-Amino-3-chloro-5-trifluoromethyl-phenyl)-3-[1-(4-hydroxy-butyl)-1H-benzimidazol-2-yl]-butyryl}-piperidin-4-yl)-1,3,4,5-tetrahydro-1,3-benzodiazepin-2-one

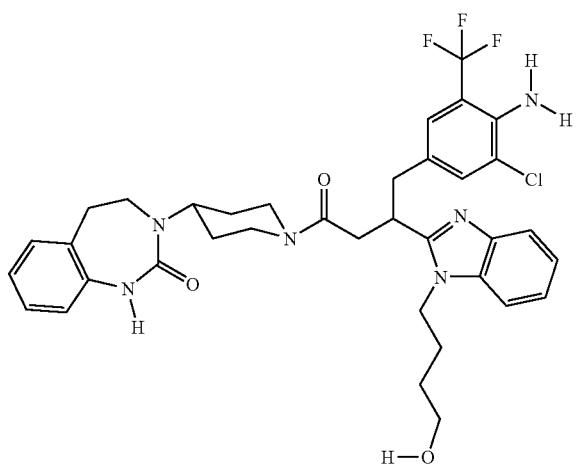

The product was obtained analogously to Example 62 starting from 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) and 4-(2-amino-phenylamino)-butan-1-ol-dihydrochloride (Intermediate product 30).

Yield: 72% of theory ESI-MS: (M+H)$^+$=697/699 (Cl)

EXAMPLE 66

3-(1-{4-(4-Amino-3-chloro-5-trifluoromethyl-phenyl)-3-[1-(1-methyl-piperidin-3-ylmethyl)-1H-benzimidazol-2-yl]-butyryl}-piperidin-4-yl)-1,3,4,5-tetrahydro-1,3-benzodiazepin-2-one

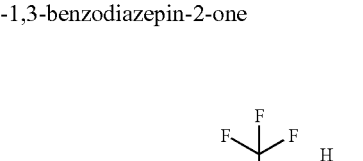

The product was obtained analogously to Example 62 starting from 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) and N-(1-methyl-piperidin-3-ylmethyl)-benzene-1,2-diamine-trihydrochloride (Intermediate product 31).

Yield: 64% of theory ESI-MS: (M+H)$^+$=736/738 (Cl)

EXAMPLE 67

3-[1-(4-(4-Amino-3-chloro-5-trifluoromethyl-phenyl)-3-{1-[2-(4-methyl-piperazin-1-yl)-ethyl]-1H-benzimidazol-2-yl}-butyryl)-piperidin-4-yl]-1,3,4,5-tetrahydro-1,3-benzodiazepin-2-one The product was obtained analogously to Example 62 starting from 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) and N-[2-(4-methyl-piperazin-1-yl)-ethyl]-benzene-1,2-diamine-tetrahydrochloride (Intermediate product 32).

Yield: 71% of theory ESI-MS: (M+H)$^+$=751/753 (Cl)

EXAMPLE 68

3-{1-[4-(4-Amino-3-chloro-5-trifluoromethyl-phenyl)-3-(1-pyridin-4-ylmethyl-1H-benzimidazol-2-yl)-butyryl]-piperidin-4-yl}-1,3,4,5-tetrahydro-1,3-benzodiazepin-2-one

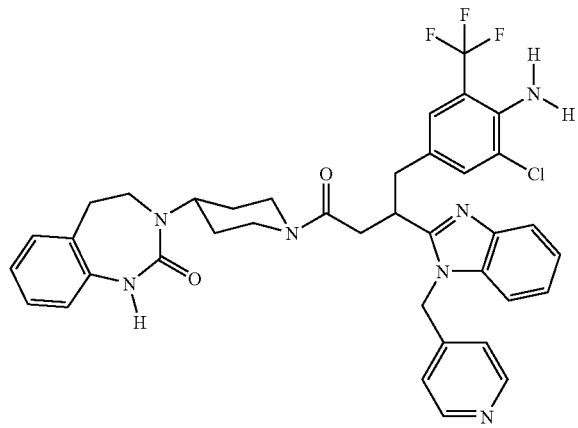

The product was obtained analogously to Example 62 starting from 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) and N-pyridin-4-ylmethyl-benzene-1,2-diamine-trihydrochloride (Intermediate product 33).

Yield: 82% of theory ESI-MS: (M+H)$^+$=716/718 (Cl)

EXAMPLE 69

3-{1-[4-(4-Amino-3-chloro-5-trifluoromethyl-phenyl)-3-(1-piperidin-4-ylmethyl-1H-benzimidazol-2-yl)-butyryl]-piperidin-4-yl}-1,3,4,5-tetrahydro-1,3-benzodiazepin-2-one

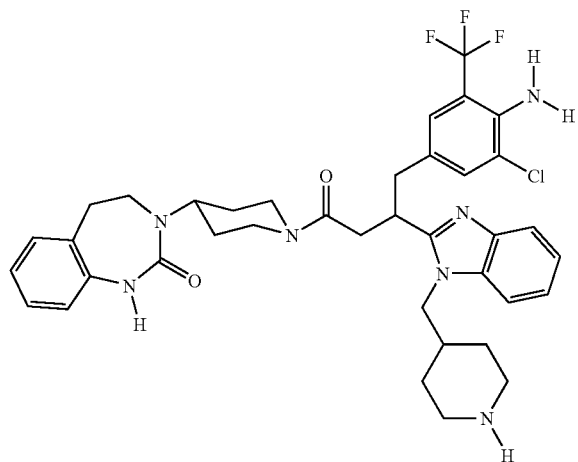

To a solution of 537 mg (1.000 mmol) 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) in 10 mL DMF was added tert. butyl 4-[(2-amino-phenylamino)-methyl]-piperidin-1-carboxylate (Intermediate product 34) and the mixture was stirred for 16 hours in an atmosphere of air at RT. The reaction mixture was poured onto ice water, the precipitate formed was filtered off, washed with water and dried i. vac. (Yield: 790 mg, 96% of theory). 1 mL of TFA was added to a solution of 580 mg (0.705 mmol) of the crude product in 10 mL dichloromethane and the mixture was stirred for 16 hours at RT. The reaction mixture was diluted with dichloromethane, the org. phase was washed with sat. aqueous sodium bicarbonate solution, dried over sodium sulphate and evaporated i. vac. The residue was dissolved in 3.5 mL DMF and purified by HPLC-MS (Zorbax Bonus C18 amide-phase 5 μm, gradient 0.15% formic acid in water/acetonitrile 10/90→90/10 v/v) and then lyophilised.

Yield: 150 mg (30% of theory) ESI-MS: (M+H)$^+$=722/724 (Cl)

EXAMPLE 70

3-(1-{4-(4-Amino-3-chloro-5-trifluoromethyl-phenyl)-3-[1-(3-dimethylamino-2,2-dimethyl-propyl)-1H-benzimidazol-2-yl]-butyryl}-piperidin-4-yl)-1,3,4,5-tetrahydro-1,3-benzodiazepin-2-one

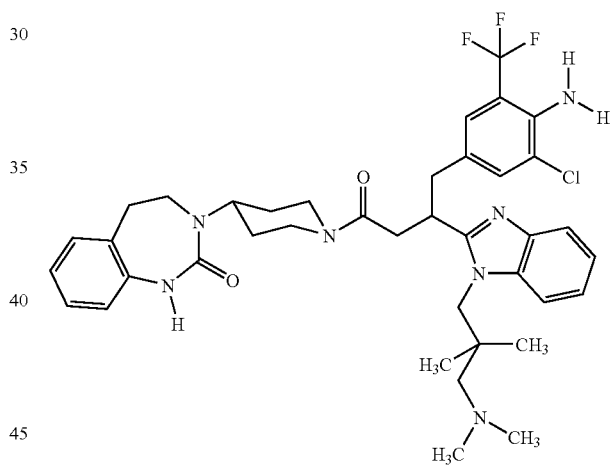

To a solution of 320 mg (0.596 mmol) 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) in 7 mL DMF was added 230 mg (0.695 mmol) N-(3-dimethylamino-2,2-dimethyl-propyl)-benzene-1,2-diamine-trihydrochloride (Intermediate product 37) and the mixture was stirred for 16 hours in an atmosphere of air. The reaction mixture was evaporated down i. vac. and the residue combined with EtOAc. The org. phase was washed with sat. aqueous sodium bicarbonate solution, dried over sodium sulphate and evaporated i. vac. The crude product was purified by column chromatography (silica gel, gradient dichloromethane/MeOH 20/1→10/1 v/v) then (Alox, neutral, activity III-III, gradient EtOAc/MeOH 100/0→40/ 1) and HPLC-MS (Zorbax Bonus C18 amide-phase 5 μm, gradient 0.15% formic acid in water/acetonitrile 10/90→90/10 v/v).

Yield: 71 mg (16% of theory) ESI-MS: (M+H)$^+$=738/740 (Cl)

EXAMPLE 71

3-(1-{4-(4-Amino-3-chloro-5-trifluoromethyl-phenyl)-3-[7-(3-dimethylamino-propoxy)-1H-benzimidazol-2-yl]-butyryl}-piperidin-4-yl)-1,3,4,5-tetrahydro-1,3-benzodiazepin-2-one

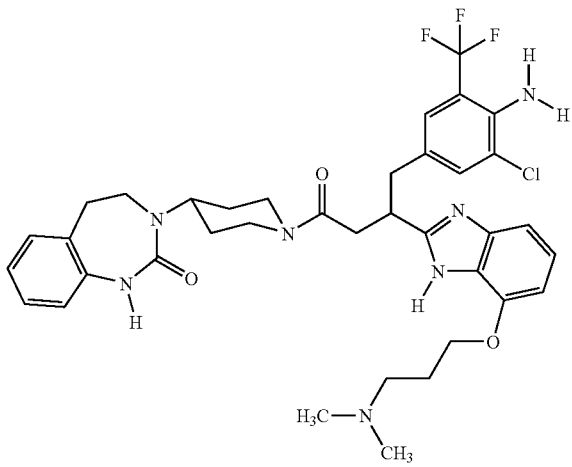

The product was obtained analogously to Example 70 starting from 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) and 3-(3-dimethylamino-propoxy)-benzene-1,2-diamine-trihydrochloride (Intermediate product 38).

Yield: 19% of theory ESI-MS: $(M+H)^+=726/728$ (Cl)

EXAMPLE 72

3-{1-[4-(4-Amino-3-chloro-5-trifluoromethyl-phenyl)-3-(1-piperidin-4-ylmethyl-1H-imidazo[4,5-c]pyridin-2-yl)-butyryl]-piperidin-4-yl}-1,3,4,5-tetrahydro-1,3-benzodiazepin-2-one

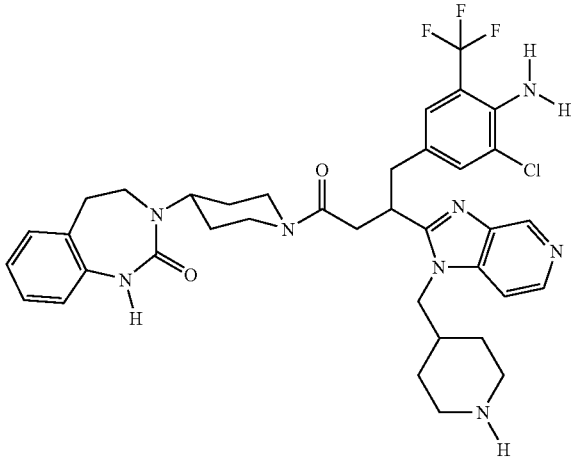

To a solution of 537 mg (1.000 mmol) 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) in 10 mL DMF was added tert. butyl 4-[(3-amino-pyridin-4-ylamino)-methyl]-piperidin-1-carboxylate (Intermediate product 40) and the mixture was stirred for 16 hours under an atmosphere of air at 100° C. The reaction mixture was poured onto ice water, the precipitate formed was filtered off, washed with water and dried i. vac. (Yield: 720 mg, 80% of theory).

1 mL TFA was added to a solution of 690 mg (0.838 mmol) of the crude product in 10 mL dichloromethane and the mixture was stirred for 16 hours at RT. The reaction mixture was diluted with dichloromethane, the org. phase was washed with sat. aqueous sodium bicarbonate solution, dried over sodium sulphate and evaporated down i. vac. The residue was dissolved in DMF and purified by means of HPLC-MS (Zorbax Bonus C18 amide-phase 5 µm, gradient 0.15% formic acid in water/acetonitrile 10/90→90/10 v/v) and then lyophilised.

Yield: 22 mg (4% of theory) ESI-MS: $(M+H)^+=723/725$ (Cl)

EXAMPLE 73

3-(-{4-(4-Amino-3-chloro-5-trifluoromethyl-phenyl)-3-[3-(3-pyrrolidin-1-yl-propyl)-3H-imidazo[4,5-c]pyridin-2-yl]-butyryl}-piperidin-4-yl)-1,3,4,5-tetrahydro-1,3-benzodiazepin-2-one

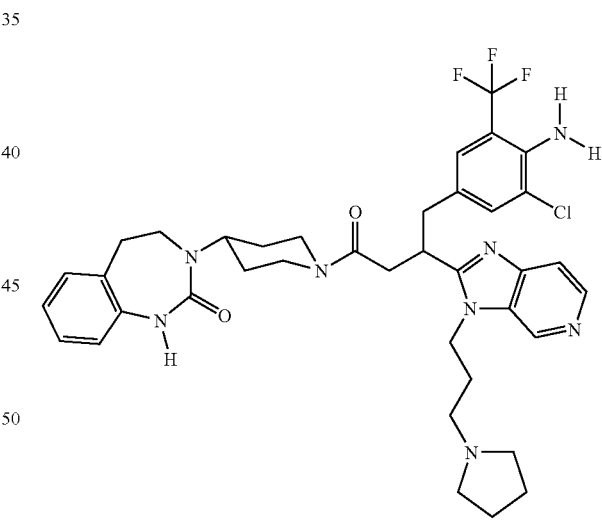

The product was prepared analogously to Example 62 starting from 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) and $N^3$-(3-pyrrolidin-1-yl-propyl)-pyridine-3,4-diamine (Intermediate product 41) at 100° C. and purified by HPLC-MS (Zorbax Bonus C18 amide-phase 5 µm, gradient 0.15% formic acid in water/acetonitrile 10/90→90/10 v/v). Lyophilisation of a 1 N aqueous solution of the product yielded the corresponding hydrochloride.

Yield: 11% of theory ESI-MS: $(M+H)^+=737/739$ (Cl)

EXAMPLE 74

3-{1-[4-(4-Amino-3-chloro-5-trifluoromethyl-phenyl)-3-(1-methyl-6-pyrrolidin-1-ylmethyl-1H-benzimidazol-2-yl)-butyryl]-piperidin-4-yl}-1,3,4,5-tetrahydro-1,3-benzodiazepin-2-one

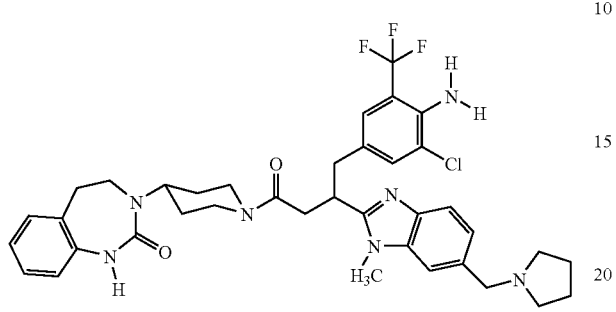

The product was prepared analogously to Example 62 starting from 2-(4-amino-3-chloro-5-trifluoromethyl-benzyl)-4-oxo-4-[4-(2-oxo-1,2,4,5-tetrahydro-1,3-benzodiazepin-3-yl)-piperidin-1-yl]-butyraldehyde (Intermediate product 36) and N²-methyl-4-pyrrolidin-1-ylmethyl-benzene-1,2-diamine (Intermediate product 42) at 100° C. and purified by HPLC-MS (Zorbax Bonus C18 amide-phase 5 μm, gradient 0.15% formic acid in water/acetonitrile 10/90→90/10 v/v).

Yield: 11% of theory HPLC-MS: R$_t$=5,622 Min. (Zorbax C18, gradient 0.1% formic acid in water/acetonitrile/formic acid 10/90→90/10 v/v/v) ESI-MS: (M+H)$^+$=722/724 (Cl)

EXAMPLE 75

Enantiomer of 3-(1-{4-(4-amino-3-chloro-5-trifluoromethyl-phenyl)-3-[1-(3-diethyl-amino-propyl)-1H-benzimidazol-2-yl]-butyryl}-piperidin-4-yl)-1,3,4,5-tetrahydro-1,3-benzodiazepin-2-one

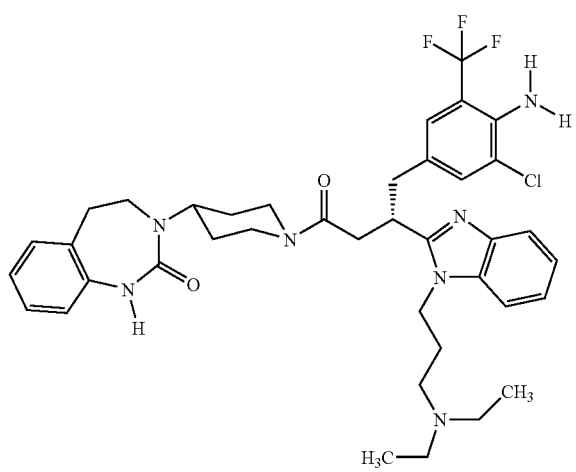

The enantiomer was obtained starting from Example 64 by HPLC (Chiralcel OD 250*4.6, hexane/EtOH/DEA 70/30/0.1 v/v/v), R$_t$(1)=14.25 Min., R$_t$(2)=17.17 Min.). ESI-MS: (M+H)$^+$=738/740 (Cl)

EXAMPLE 76

Enantiomer of 3-[1-(4-(4-amino-3-chloro-5-trifluoromethyl-phenyl)-3-{1-[2-(4-methyl-piperazin-1-yl)-ethyl]-1H-benzimidazol-2-yl}-butyryl)-piperidin-4-yl]-1,3,4,5-tetrahydro-1,3-benzodiazepin-2-one

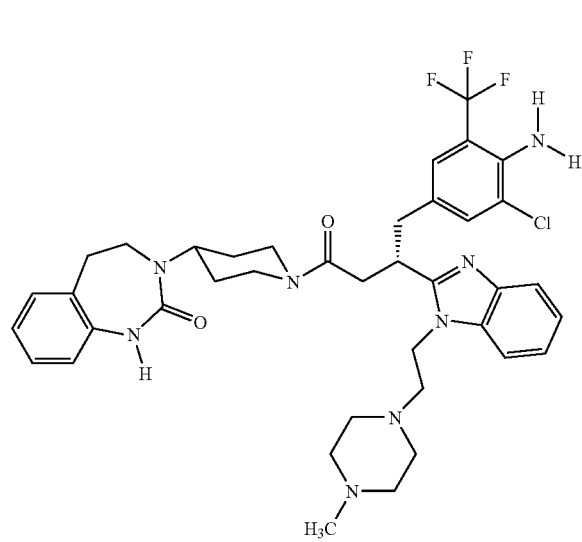

The enantiomer was obtained starting from Example 67 using HPLC (Chiralcel OD 250*4.6, hexane/ EtOH/DEA 70/30/0.1 v/v/v), R$_t$(1)=21.75 Min., R$_t$(2)=24.86 Min.).

ESI-MS: (M+H)$^+$=751/753 (Cl)

The following Examples describe the preparation of pharmaceutical formulations which contain as active substance any desired compound of general formula (I):

EXAMPLE 77

Capsules for Powder Inhalation Containing 1 mg of Active Ingredient

Composition:
1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

EXAMPLE 78

Inhalable solution for Respimat® containing 1 mg of active ingredient

Composition:
1 puff contains:

| active ingredient | 1.0 mg |
|---|---|
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

EXAMPLE 79

Inhalable Solution for Nebulisers Containing 1 mg of Active Ingredient

Composition:
1 vial contains:

| active ingredient | 0.1 g |
|---|---|
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

EXAMPLE 80

Propellant Gas-Operated Metering Aerosol Containing 1 mg of Active Ingredient

Composition:
1 puff contains:

| active ingredient | 1.0 mg |
|---|---|
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

EXAMPLE 81

Nasal Spray Containing 1 mg of Active Ingredient
Composition:

| active ingredient | 1.0 mg |
|---|---|
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

EXAMPLE 82

Injectable Solution Containing 5 mg of Active Substance per 5 ml

Composition:

| active substance | 5 mg |
|---|---|
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

EXAMPLE 83

Injectable Solution Containing 100 mg of Active Substance per 20 ml

Composition:

| active substance | 100 mg |
|---|---|
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

EXAMPLE 84

Lyophilisate Containing 10 mg of Active Substance

Composition:

| | |
|---|---|
| Active substance | 10 mg |
| Mannitol | 300 mg |
| human serum albumin | 20 mg |

Preparation:
Mannitol is dissolved in water for injections (Wfl); human serum albumin is added; active ingredient is dissolved with heating; made up to specified volume with Wfl; transferred into vials; freeze-dried.

Solvent for lyophilisate:

| | |
|---|---|
| Polysorbate 80 = Tween 80 | 20 mg |
| mannitol | 200 mg |
| water for injections ad | 10 ml |

Preparation:
Polysorbate 80 and mannitol are dissolved in water for injections (Wfl); transferred into ampoules.

EXAMPLE 85

Tablets containing 20 mg of active substance

Composition:

| | |
|---|---|
| active substance | 20 mg |
| lactose | 120 mg |
| maize starch | 40 mg |
| magnesium stearate | 2 mg |
| Povidone K 25 | 18 mg |

Preparation:
Active substance, lactose and maize starch are homogeneously mixed; granulated with an aqueous solution of Povidone; mixed with magnesium stearate; compressed in a tablet press; weight of tablet 200 mg.

EXAMPLE 86

Capsules Containing 20 mg Active Substance

Composition:

| | |
|---|---|
| active substance | 20 mg |
| maize starch | 80 mg |
| highly dispersed silica | 5 mg |
| magnesium stearate | 2.5 mg |

Preparation:
Active substance, maize starch and silica are homogeneously mixed; mixed with magnesium stearate; the mixture is packed into size 3 hard gelatine capsules in a capsule filling machine.

EXAMPLPE 87

Suppositories Containing 50 mg of Active Substance

Composition:

| | |
|---|---|
| active substance | 50 mg |
| hard fat (*Adeps solidus*) q.s. ad | 1700 mg |

Preparation:
Hard fat is melted at about 38° C.; ground active substance is homogeneously dispersed in the molten hard fat; after cooling to about 35° C. it is poured into chilled moulds.

EXAMPLE 88

Injectable Solution Containing 10 mg of Active Substance per 1 ml

Composition:

| | |
|---|---|
| active substance | 10 mg |
| mannitol | 50 mg |
| human serum albumin | 10 mg |
| water for injections ad | 1 ml |

Preparation:
Mannitol is dissolved in water for injections (Wfl); human serum albumin is added; active ingredient is dissolved with heating; made up to specified volume with Wfl; transferred into ampoules under nitrogen gas.

We claim:
1. Compounds of general formula

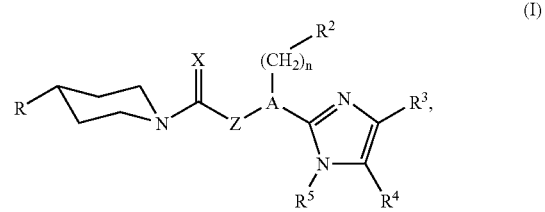

(I)

wherein,
R denotes a dihydroquinazolinyl group,
while said dihydroquinazolinyl group is linked via a carbon or nitrogen atom and
contains one carbonyl group, which is linked to at least one nitrogen atom,
may be substituted by an alkyl group at one of the nitrogen atoms,
may be substituted at one or two carbon atoms in each case by an alkyl, phenyl, phenylmethyl, naphthyl, biphenylyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl group, while the substituents may be identical or different, while the phenyl, pyridinyl, diazinyl, furyl, thienyl, pyrrolyl, 1,3-oxazolyl, 1,3-thiazolyl, isoxazolyl, pyrazolyl, 1-methylpyrazolyl, imidazolyl or 1-methylimidazolyl groups contained in R as well as the benzo-fused group in the carbon skeleton may additionally be mono-, di- or trisubstituted by fluorine, chlorine, bromine or iodine atoms, by alkyl, alkoxy, nitro, alkylthio, alkylsulphinyl, alkylsulphonyl, alkylsulphonylamino, phenyl, trifluoromethyl, difluoromethyl, difluoromethoxy, alkoxycarbonyl, carboxy, dialkyl-amino, hydroxy, amino, acetylamino, propionylamino, aminocarbonyl, alkylaminocarbonyl, dialkylaminocarbonyl, (4-morpholinyl)carbonyl, (1-pyrrolidinyl) carbonyl, (1-piperidinyl)carbonyl, (hexahydro-1-azepinyl)carbonyl, (4-methyl-1-piperazinyl)carbonyl, methylenedioxy, aminocarbonylamino, alkanoyl, cyano, trifluoromethoxy, trifluoromethylthio, trifluoromethylsulphinyl or trifluoromethylsulphonyl groups, while the substituents may be identical or different, X denotes an oxygen atom or, if Z denotes the group —NR$^1$-, it may also denote one of the groups =N—CN or =N—SO$_2$-R$^6$, wherein R$^6$ denotes an alkyl group with 1 to 4 carbon atoms or a phenyl group optionally substituted by a halogen atom, a methyl or a methoxy group, Z denotes one of the groups —CH$_2$—, wherein the hydrogen atoms may be replaced independently of one another by a fluorine atom or a C$_{1-3}$-alkyl group, or —NR$^1$, wherein R$^1$ denotes the hydrogen atom, an alkyl group which may be substituted in the alkyl moiety with the exception of position 1 by an amino, C$_{1-3}$-alkyl-amino or di-(C$_{1-3}$-alkyl)-amino group, or a phenylalkyl group which may be mono- or disubstituted in the phenyl moiety by fluorine, chlorine, bromine or iodine atoms, by a C$_{1-3}$-alkyl, trifluoromethyl, difluoromethyl, cyclopropyl, hydroxy, C$_{1-3}$-alkoxy, difluoromethoxy, trifluoromethoxy, cyano, nitro, amino, C$_{1-3}$-alkyl-amino, di-(C$_{1-3}$-alkyl)-amino, carboxy, C$_{1-3}$-alkoxy-carbonyl aminocarbonyl, C$_{1-3}$-alkyl-aminocarbonyl, di-(C$_{1-3}$-alkyl)-aminocarbonyl, amino-C$_{1-3}$-alkyl, C$_{1-3}$-alkyl-amino-C$_{1-3}$-alkyl or di-(C$_{1-3}$-alkyl)-amino-C$_{1-3}$-alkyl group, while the substituents may be identical or different, A denotes a carbon atom substituted by a hydrogen atom or by a C$_{1-3}$-alkyl group n denotes the number 1 or 2, R$^2$ denotes the group

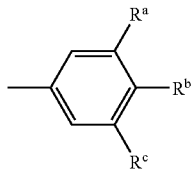

wherein
one of the groups R$^a$, R$^b$ and R$^c$ denotes the hydrogen, fluorine, chlorine, bromine or iodine atom, a branched or unbranched alkyl group, a hydroxy, alkoxy, trifluoromethyl, difluoromethyl, trifluoromethoxy, difluoromethoxy, trifluoromethylthio, amino, acetylamino, dialkylaminoalkyl, dialkylaminoalkoxy, nitro, methylsulphonyloxy, aminocarbonyl, alkylaminocarbonyl, dialkylaminocarbonyl, alkanoyl, cyano, trifluoromethylsulphinyl or trifluoromethylsulphonyl group, a second of the groups R$^a$, R$^b$ and R$^c$ denotes the hydrogen, fluorine, chlorine, bromine or iodine atom, a branched or unbranched alkyl group, a hydroxy, alkoxy, trifluoromethyl, difluoromethyl, trifluoromethoxy, difluoromethoxy, trifluoromethylthio, amino, acetylamino, alkanoyl, aminocarbonyl, alkylaminocarbonyl or dialkylaminocarbonyl group and the third of the groups R$^a$, R$^b$ and R$^c$ denotes the hydrogen, fluorine, chlorine, bromine or iodine atom, a branched or unbranched alkyl group, a hydroxy, alkoxy, trifluoromethyl, difluoromethyl, difluoromethoxy, or trifluoromethoxy group, while the substituents may be identical or different, R$^3$ and R$^4$, which may be identical or different, in each case denote the hydrogen atom, a C$_{1-4}$-alkyl, amino-C$_{1-3}$-alkyl, C$_{1-3}$-alkyl-amino-C$_{1-3}$-alkyl or di-(C$_{1-3}$-alkyl)-amino-C$_{1-3}$-alkyl group, a phenyl or naphthyl group which in each case may be mono- or disubstituted by R$^d$, while the substituents may be identical or different and R$^d$ denotes a fluorine, chlorine, bromine or iodine atom, a C$_{1-3}$-alkyl, trifluoromethyl, difluoromethyl, cyclopropyl, hydroxy, C$_{1-3}$-alkoxy, difluoromethoxy, trifluoromethoxy, cyano, nitro, amino, C$_{1-3}$-alkyl-amino, di-(C$_{1-3}$-alkyl)-amino, carboxy, C$_{1-3}$-alkoxy-carbonyl, aminocarbonyl, C$_{1-3}$-alkyl-aminocarbonyl, di-(C$_{1-3}$-alkyl)-aminocarbonyl, amino-C$_{1-3}$-alkyl, C$_{1-3}$-alkyl-amino-C$_{1-3}$-alkyl or di-(C$_{1-3}$-alkyl)-amino-C$_{1-3}$-alkyl group or a 4- to 7-membered cycloalkyleneimino-carbonyl group wherein one or two hydrogen atoms may each be replaced by a C$_{1-3}$-alkyl group and/or in each case the methylene group in the 4 position of a 6- or 7-membered cycloalkyleneimino moiety may be replaced by an oxygen or sulphur atom, by a sulphinyl, sulphonyl, -NH, -N(C$_{1-3}$-alkyl) or -N(C$_{1-3}$-alkyl-carbonyl) group, a monocyclic 5- or 6-membered heteroaryl group optionally substituted in the carbon skeleton by a C$_{1-3}$-alkyl, amino, C$_{1-3}$-alkyl-amino, di-(C$_{1-3}$-alkyl)-amino, carboxy, C$_{1-3}$-alkoxy-carbonyl, aminocarbonyl, C$_{1-3}$-alkyl-aminocarbonyl, di-(C$_{1-3}$-alkyl)-aminocarbonyl, amino-C$_{1-3}$-alkyl, C$_{1-3}$-alkyl-amino-C$_{1-3}$-alkyl or di-(C$_{1-3}$-alkyl)-amino-C$_{1-3}$-alkyl group, while the 6-membered heteroaryl group contains one, two or three nitrogen atoms and may optionally additionally be substituted by a fluorine, chlorine, bromine or iodine atom, a C$_{1-3}$-alkyl, C$_{1-3}$-alkoxy, amino, C$_{1-3}$-alkylamino or di-(C$_{1-3}$-alkyl)amino group and the 5-membered heteroaryl group contains an imino group optionally substituted by a C$_{1-3}$-alkyl, acetyl, trifluoroacetyl, C$_{1-3}$-alkoxy-carbonyl, aminocarbonyl, C$_{1-3}$-alkyl-aminocarbonyl, di-(C$_{1-3}$-alkyl)-aminocarbonyl, amino-C$_{1-3}$-alkyl, C$_{1-3}$-alkyl-amino-C$_{1-3}$-alkyl or di-(C$_{1-3}$-alkyl)-amino-C$_{1-3}$-alkyl group, an oxygen or sulphur atom or an imino group optionally substituted by a C$_{1-3}$-alkyl, acetyl, trifluoroacetyl, C$_{1-3}$-alkoxy-carbonyl, aminocarbonyl, C$_{1-3}$-alkyl-aminocarbonyl, di-(C$_{1-3}$-alkyl)-amino-carbonyl, amino-C$_{1-3}$-alkyl, C$_{1-3}$-alkylamino-$C_{1-3}$-alkyl or di-($C_{1-3}$-alkyl)-amino-$C_{1-3}$-alkyl group or an oxygen or sulphur atom and additionally a nitrogen atom or an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-amino-carbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group and two nitrogen atoms, or $R^3$ and $R^4$ together (denote) a 1,3-butadien-1,4-ylene group wherein one, two or three methyne groups may each be replaced by a nitrogen atom, a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, di-($C_{1-3}$-alkyl)-amino-$C_{2-3}$-alkyl-aminocarbonyl, amino-$C_{1-3}$-alkyl, $C_{1-3}$alkyl-amino-$C_{1-3}$-alkyl or di-($C_{1-3}$-alkyl)-amino-$C_{1-3}$-alkyl group or by a 4- to 7-membered cycloalkyleneimino-carbonyl group wherein one or two hydrogen atoms may each be replaced by a $C_{1-3}$-alkyl group and/or in each case the methylene group in the 4 position of a 6- or 7-membered cyclo-alkyleneimino moiety may be replaced by an oxygen or sulphur atom, by a sulphinyl, sulphonyl, -NH, -N($C_{1-3}$-alkyl) or -N($C_{1-3}$-alkyl-carbonyl)- group, and optionally additionally a second hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy or trifluoromethoxy group, and $R^5$ denotes the group -$(CH_2)_m$-$R^e$, wherein m denotes the number 0 and $R^e$ denotes a hydrogen atom, a phenyl or naphthyl group which in each case may be mono- or disubstituted by $R^f$, while the substituents may be identical or different and $R^f$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or a pyridinyl, pyrazinyl, pyrimidinyl, pyridazinyl, pyrrolyl, furyl, thienyl, pyrazolyl, imidazolyl, oxazolyl, isoxazolyl, thiazolyl or isothiazolyl group optionally substituted in the carbon skeleton by a $C_{1-3}$-alkyl group, wherein a hydrogen atom bound to a nitrogen atom may be replaced by a $C_{1-3}$-alkyl or acetyl group, or a $C_{3-7}$-cycloalkyl group, while a hydrogen atom of the $C_{3-7}$-cycloalkyl group may be replaced by an amino, $C_{1-3}$-alkyl-amino, di-($C_{1-3}$-alkyl)-amino, amino-$C_{1-3}$-alkyl, $C_{1-3}$-alkyl-amino-$C_{1-3}$-alkyl or di-($C_{1-3}$-alkyl)-amino-$C_{1-3}$-alkyl group and/or the methylene group in the 3 position of the cyclopentyl group and the methylene group in the 4 position of the cyclohexyl and cycloheptyl group may each be replaced by an oxygen or sulphur atom, by a sulphinyl, sulphonyl, -NH, -N($C_{1-3}$-alkyl) or -N($C_{1-3}$-alkyl-carbonyl)- group, or m denotes one of the numbers i to 5 and $R^e$ denotes a hydrogen atom, an aminomethylene, $C_{1-3}$-alkylaminomethylene, di-($C_{1-3}$-alkyl)-aminomethylene, aminocarbonyl, $C_{1-3}$-alkylaminocarbonyl, di-($C_{1-3}$-alkyl)-aminocarbonyl or $C_{3-7}$-cycloalkyl group, while a hydrogen atom of the $C_{3-7}$-cycloalkyl group may be replaced by an amino, $C_{1-3}$-alkyl-amino, di-($C_{1-3}$-alkyl)-amino, amino-$C_{1-3}$-alkyl, $C_{1-3}$-alkyl-amino-$C_{-13}$-alkyl or di-($C_{1-3}$-alkyl)-amino-$C_{1-3}$-alkyl group and/or the methylene group in the 3 position of the cyclopentyl group and the methylene group in the 4 position of the cyclohexyl and cycloheptyl group may each be replaced by an oxygen or sulphur atom, by a sulphinyl, sulphonyl, -NH, -N($C_{1-3}$-alkyl) or -N($C_{1-3}$-alkyl-carbonyl)- group, a 4- to 7-membered cycloalkyleneimino group wherein one or two hydrogen atoms may each be replaced by a $C_{1-3}$-alkyl group and/or in each case the methylene group in the 4 position of a 6 or 7-membered cyclo-alkyleneimino group may be replaced by an oxygen or sulphur atom, by a sulphinyl, sulphonyl, -NH, -N($C_{1-3}$-alkyl) or -N($C_{1-3}$-alkyl-carbonyl)- group, a phenyl or naphthyl group which may be mono- or disubstituted by $R^g$ in each case independently of one another, while the substituents may be identical or different and $R^g$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or a monocyclic 5- or 6-membered heteroaryl group optionally substituted in the carbon skeleton by a $C_{1-3}$-alkyl, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, while the 6-membered heteroaryl group contains one, two or three nitrogen atoms and may optionally additionally be substituted by a fluorine, chlorine, bromine or iodine atom, a C1-3-alkyl, C1-3-alkoxy, amino, C1-3-alkylamino or di-(C1-3-alkyl)amino group and the 5-membered heteroaryl group contains an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, an oxygen or sulphur atom or an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino- $C_{1-3}$-alkyl group or an oxygen or sulphur atom and additionally a nitrogen atom or an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group and two nitrogen atoms, while said alkyl groups or the alkyl groups contained in said groups, unless otherwise stated, contain 1 to 5 carbon atoms and may be branched or unbranched, the tautomers, diastereomers, enantiomers, mixtures and salts thereof.

2. Compounds of general formula I according to claim 1, wherein

R denotes a dihydroquinazolinyl group, while said dihydroquinazolinyl group is linked via a nitrogen atom and contains a carbonyl group linked to one or two nitrogen atoms of the heterocyclic group, may be substituted by an alkyl group at one of the nitrogen atoms, may be substituted at one of the carbon atoms by an alkyl, phenyl, pyridinyl, furyl, thienyl or pyrrolyl group, while the phenyl, pyridinyl, furyl, thienyl, pyrrolyl groups contained in R as well as the benzo-condensed heterocyclic group in the carbon skeleton may additionally be mono- or disubstituted by fluorine, chlorine, bromine or iodine atoms, by alkyl, alkoxy, nitro, alkylthio, trifluoromethyl, difluoromethyl, alkoxycarbonyl, carboxy, dialkylamino, hydroxy, amino, acetylamino, aminocarbo-nyl, alkylaminocarbonyl, alkanoyl, cyano or trifluoromethoxy groups, while the substituents may be identical or different, X denotes an oxygen atom or, if Z the group -NR$^1$- denotes, it may also denote the group =N-CN, Z denotes one of the groups -CH$_2$ or -NR$^1$, wherein R$^1$ denotes the hydrogen atom or an alkyl group, A denotes a carbon atom substituted by a hydrogen atom or by a $C_{1-3}$-alkyl group, n denotes the number 1 or 2, R$^2$ denotes the group

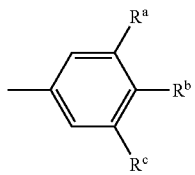

wherein one of the groups R$^a$, R$^b$ and R$^c$ denotes the hydrogen, fluorine, chlorine, bromine or iodine atom, a branched or unbranched alkyl group, a hydroxy, alkoxy, trifluoromethyl, difluoromethyl, trifluoromethoxy, amino, acetylamino, dialkylaminoalkyl, dialkylaminoalkoxy, aminocarbonyl, alkylaminocarbonyl, dialkylaminocarbonyl, alkanoyl, cyano or trifluoromethylsulphonyl group, a second of the groups R$^a$, R$^b$ and R$^c$ denotes the hydrogen, fluorine, chlorine, bromine or iodine atom, a branched or unbranched alkyl group, an alkoxy, trifluoromethyl, amino, acetylamino or alkanoyl group and the third of the groups R$^a$, R$^b$ and R$^c$ denotes the hydrogen, fluorine, chlorine, bromine or iodine atom or a branched or unbranched alkyl group, while the substituents may be identical or different, R$^3$ denotes the hydrogen atom or a $C_{1-3}$-alkyl group, R$^4$ denotes the hydrogen atom, a $C_{1-4}$-alkyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, a phenyl group which may be mono- or disubstituted by R$^d$, while the substituents may be identical or different and R$^d$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, amino, $C_{1-3}$-alkylamino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or a pyridinyl, pyrazinyl, pyrimidinyl, pyridazinyl, pyrrolyl, furyl, thienyl, pyrazolyl, imidazolyl, oxazolyl, isoxazolyl, thiazolyl or isothiazolyl group optionally substituted in the carbon skeleton by a $C_{1-3}$-alkyl group, wherein a hydrogen atom bound to a nitrogen atom may be replaced by a $C_{1-3}$-alkyl or acetyl group, or R$^3$ and R$^4$ together denote a 1,3-butadien-1,4-ylene group wherein a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, di-($C_{1-3}$-alkyl)-amino-$C_{2-3}$-alkyl-aminocarbonyl, amino-$C_{1-3}$-alkyl, $C_{1-3}$-alkyl-amino-$C_{1-3}$-alkyl, di-($C_{1-3}$-alkyl)-amino-$C_{1-3}$-alkyl group or by a 5- to 7-membered cycloalkyleneiminocarbonyl group wherein one or two hydrogen atoms may each be replaced by a $C_{1-3}$-alkyl group and/or in each case the methylene group in the 4 position of a 6- or 7-membered cyclo-alkyleneimino moiety by an oxygen or sulphur atom, may be replaced by a -NH, -N($C_{1-3}$-alkyl) or -N($C_{1-3}$-alkyl-carbonyl)-group, and optionally a second hydrogen atom may additionally be replaced by a fluorine, chlorine, bromine or iodine atom, by a $C_{1-3}$-alkyl or trifluoromethyl group, and R$^5$ denotes the group -(CH$_2$)$_m$R$^e$, wherein m denotes the number 0 and R$^e$ denotes a hydrogen atom or a $C_{5-6}$-cycloalkyl group, while the methylene group in the 3 position of the cyclopentyl group and the methylene group in the 4 position of the cyclohexyl group may each be replaced by a -NH, -N($C_{1-3}$-alkyl) or -N($C_{1-3}$-alkyl-carbonyl) group, or m denotes one of the numbers 1 to 5 and R$^e$ denotes a hydrogen atom, an aminomethylene, $C_{1-3}$-alkylaminomethylene, di-($C_{1-3}$-alkyl)-aminomethylene, aminocarbonyl, $C_{1-3}$-alkyl-aminocarbonyl, di-($C_{1-3}$-alkyl)-amino carbonyl or $C_{5-6}$-cycloalkyl group, while the methylene group in the 3 position of the cyclopentyl group and the methylene group in the 4 position of the cyclohexyl group may each be replaced by a -NH, -N($C_{1-3}$-alkyl) or -N($C_{1-3}$-alkyl-carbonyl) group, a 5- to 6-membered cycloalkyleneimino group, while
the methylene group in the 4 position of a 6-membered cycloalkyleneimino group may be replaced by a -NH, -N($C_{1-3}$-alkyl) or -N($C_{1-3}$-alkyl-carbonyl)- group, a phenyl group which may be mono- or disubstituted by $R^g$ while the substituents may be identical or different and $R^g$ denotes a fluorine, chlorine, bromine or iodine atom, a $C_{1-3}$-alkyl, trifluoromethyl, difluoromethyl, hydroxy, $C_{1-3}$-alkoxy, amino, $C_{1-3}$-alkyl-amino, di-($C_{1-3}$-alkyl)-amino, aminocarbonyl- $C_{1-3}$-alkyl-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or a pyridinyl, pyrazinyl, pyrimidinyl, pyridazinyl, pyrrolyl, furyl, thienyl, pyrazolyl, imidazolyl, oxazolyl, isoxazolyl, thiazolyl or isothiazolyl group optionally substituted in the carbon skeleton by a $C_{1-3}$-alkyl group, wherein a hydrogen atom bound to a nitrogen atom by a $C_{1-3}$-alkyl or acetyl group may be replaced, while said alkyl groups or the alkyl groups contained in said groups, unless otherwise stated, contain 1 to 4 carbon atoms and may be branched or unbranched, the tautomers, diastereomers, enantiomers, mixtures and salts thereof.

3. Compounds of general formula I according to claim 2, wherein

R denotes a dihydroquinazolinyl group linked via a nitrogen atom,
while said dihydroguinazolinyl group contains a carbonyl group linked to both nitrogen atoms of the heterocyclic group,
may each be substituted independently of one another at one of the nitrogen atoms and one of the saturated carbon atoms by a $C_{1-3}$-alkyl group, X denotes an oxygen atom, Z denotes one of the groups -$CH_2$ or -$NR^1$ wherein
$R^1$ denotes the hydrogen atom or a $C_{1-3}$-alkyl group, A denotes a carbon atom substituted by a hydrogen atom or by a $C_{1-3}$-alkyl group, n denotes the number 1, $R^2$ denotes the group

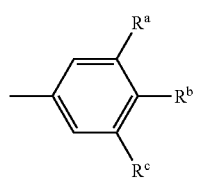

wherein
one of the groups $R^a$, $R^b$ and $R^c$ denotes the hydrogen, fluorine, chlorine, bromine or iodine atom, a $C_{1-3}$-alkyl, trifluoromethyl, hydroxy, alkoxy or amino group, a second of the groups $R^a$, $R^b$ and $R^c$ denotes the hydrogen, fluorine, chlorine, bromine or iodine atom, a $C_{1-3}$-alkyl or trifluoromethyl group and the third of the groups $R^a$, $R^b$ and $R^c$ denotes the hydrogen, fluorine, chlorine, bromine or iodine atom, while the substituents may be identical or different, $R^3$ denotes the hydrogen atom or a $C_{1-3}$-alkyl group, $R^4$ denotes a phenyl group optionally substituted by a fluorine, chlorine, bromine or iodine atom, by a $C_{1-3}$-alkyl, trifluoromethyl, hydroxy, $C_{1-3}$-alkoxy, amino, $C_{1-3}$-alkylamino, di-($C_{1-3}$-alkyl)-amino, carboxy or $C_{1-3}$-alkoxy-carbonyl group, or $R^3$ and $R^4$ together denote a 1,3-butadien-1,4-ylene group wherein
a hydrogen atom may be replaced by a fluorine, chlorine, bromine or iodine atom, by a $C_{1-3}$-alkyl, trifluoromethyl, hydroxy, $C_{1-3}$-alkoxy, carboxy, $C_{1-3}$-alkoxy-carbonyl, aminocarbonyl, $C_{1-3}$-alkyl-aminocarbonyl, di-($C_{1-3}$-alkyl)-aminocarbonyl or di ($C_{1-3}$alkyl)-amino-$C_{2-3}$-alkyl-aminocarbonyl group or by a 5- to 7-membered cycloalkyleneimino-carbonyl group, while
the methylene group in the 4 position of the 6-membered cycloalkyleneimino moiety may be replaced by a -NH, -N($C_{1-3}$-alkyl) or -N($C_{1-3}$-alkyl-carbonyl)- group, and optionally a second hydrogen atom may be replaced by a fluorine, chlorine, bromine or iodine atom or by a $C_{1-3}$-alkyl group, and $R^5$ denotes the group -$(CH_2)_m R^e$, wherein
m denotes the number 0 and
$R^e$ denotes a hydrogen atom,
or m denotes one of the numbers i to 3 and
$R^e$ denotes a hydrogen atom, an aminomethylene, $C_{1-3}$-alkylaminomethylene or di-($C_{1-3}$-alkyl)-aminomethylene group, while said alkyl groups or the alkyl groups contained in said groups, unless otherwise stated, may be branched or unbranched, the tautomers, diastereomers, enantiomers, mixtures and salts thereof.

4. Compounds of general formula I according to claim 1, wherein

R, X, Z, A, n, $R^2$, and $R^5$ are defined as in claim 1 and
$R^3$ denotes a hydrogen atom or a $C_{1-4}$-alkyl group and
$R^4$ denotes a hydrogen atom, a $C_{1-4}$-alkyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, a phenyl or naphthyl group which may be mono- or disubstituted by $R^d$ in each case independently of one another, while the substituents may be identical or different and $R^d$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_3$-alkyl group, or a monocyclic 5- or 6-membered heteroaryl group optionally substituted in the carbon skeleton by a $C_{1-3}$-alkyl, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, while the 6-membered heteroaryl group contains one, two or three nitrogen atoms and
the 5-membered heteroaryl group contains an imino group optionally substituted by a $C_{1-3}$-alkyl, acetyl, trifluoroacetyl, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino- $C_{1-3}$-alkyl or di-($C_{1-3}$-alkyl)-amino-$C_{1-3}$-alkyl group, an oxygen or sulphur atom or an imino group optionally substituted by a $C_{1-3}$-alkyl, acetyl, trifluoroacetyl-$C_{1-3}$-alkoxy-carbonyl, aminocarbonyl, $C_{1-3}$-alkyl-aminocarbonyl, di-($C_{1-3}$-alkyl)-amino-carbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or an oxygen or sulphur atom and additionally a nitrogen atom or an imino group optionally substituted by a $C_{1-3}$-alkyl, acetyl, trifluoroacetyl-$C_{1-3}$-alkoxy-carbonyl, aminocarbonyl, $C_{1-3}$-alkyl-aminocarbonyl, di-($C_{1-3}$-alkyl)-amino-carbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group and two nitrogen atoms, the tautomers, diastereomers, enantiomers, mixtures and salts thereof.

5. Compounds of general formula I according to claim 2, wherein

R, X, Z, A, n, $R^2$, and $R^5$ are defined as in claim 2 and $R^3$ denotes the hydrogen atom or a $C_{1-3}$-alkyl group and $R^4$ denotes a phenyl group which may be mono- or disubstituted by $R^d$, while the substituents may be identical or different and $R^d$ denotes a fluorine, chlorine, bromine or iodine atom, a $C_{1-3}$-alkyl, trifluoromethyl, difluoromethyl, cyclopropyl, hydroxy, $C_{1-3}$-alkoxy, difluoromethoxy, trifluoromethoxy, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group, or a pyridinyl, pyrazinyl, pyrimidinyl, pyridazinyl, pyrrolyl, furyl, thienyl, pyrazolyl, imidazolyl, oxazolyl, isoxazolyl, thiazolyl or isothiazolyl group optionally substituted in the carbon skeleton by a $C_{1-3}$-alkyl group, wherein a hydrogen atom bound to a nitrogen atom may be replaced by a $C_{1-3}$-alkyl or acetyl group, the tautomers, diastereomers, enantiomers, mixtures and salts thereof.

6. Compounds of general formula I according to claim 3, wherein

R, X, Z, A, n, $R^2$, and $R^5$ are defined as in claim 3 and $R^3$ denotes the hydrogen atom or a $C_{1-3}$-alkyl group and $R^4$ denotes a phenyl group optionally substituted by a fluorine, chlorine, bromine or iodine atom, by a $C_{1-3}$-alkyl, trifluoromethyl, hydroxy, $C_{1-3}$-alkoxy, amino, $C_{1-3}$-alkylamino, di-($C_{1-3}$-alkyl)-amino, carboxy or $C_{1-3}$-alkoxy-carbonyl group, the tautomers, diastereomers, enantiomers, mixtures and salts thereof.

7. Compounds of general formula I according to claim 1, wherein

R, X, Z, A, n, $R^2$, and $R^5$ are defined as in claim 1 and $R^3$ and $R^4$ together denote a 1,3-butadien-1,4-ylene group wherein one, two or three methyne groups may each be replaced by a nitrogen atom, a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy, trifluoromethoxy, cyano, nitro, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl, di-($C_{1-3}$-alkyl)-amino-$C_{2-3}$-alkyl-aminocarbonyl, amino-$C_{1-3}$-alkyl, $C_{1-3}$-alkyl-amino-$C_{1-3}$-alkyl or di-($C_{1-3}$-alkyl)-amino-$C_{1-3}$-alkyl group or by a 4- to 7-membered cycloalkyleneimino-carbonyl group wherein one or two hydrogen atoms may each be replaced by a $C_{1-3}$-alkyl group and/or in each case the methylene group in the 4 position of a 6- or 7-membered cyclo-alkyleneimino moiety may be replaced by an oxygen or sulphur atom, by a sulphin-yl, sulphonyl, -NH, -N($C_{1-3}$-alkyl) or -N($C_{1-3}$-alkyl-carbonyl)- group, and a second hydrogen atom may optionally additionally be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, difluoromethoxy or trifluoromethoxy group, the tautomers, diastereomers, enantiomers, mixtures and salts thereof.

8. Compounds of general formula I according to claim 2, wherein

R, X, Z, A, n, $R^2$, and $R^5$ are defined as in claim 2 and $R^3$ and $R^4$ together denote a 1,3-butadien-1,4-ylene group wherein a hydrogen atom may be replaced by a fluorine, chlorine, bromine or iodine atom, by a $C_{1-3}$-alkyl, trifluoromethyl, difluoromethyl, cyclopropyl, hydroxy, $C_{1-3}$-alkoxy, amino, $C_{1-3}$-alkyl-amino, di-($C_{1-3}$-alkyl)-amino, carboxy, $C_{1-3}$-alkoxy-carbonyl, aminocarbonyl, $C_{1-3}$-alkyl-aminocarbonyl, di-($C_{1-3}$-alkyl)-aminocarbonyl or di-($C_{1-3}$-alkyl)-amino-$C_{2-3}$-alkyl-aminocarbonyl group or by a 5- to 7-membered cycloalkyleneimino-carbonyl group wherein one or two hydrogen atoms may each be replaced by a $C_{1-3}$-alkyl group and/or in each case the methylene group in the 4 position of a 6- or 7-membered cyclo-alkyleneimino moiety may be replaced by an oxygen or sulphur atom, by a -NH, -N($C_{1-3}$-alkyl) or -N($C_{1-3}$-alkyl-carbonyl)- group, and a second hydrogen atom may optionally additionally be replaced by a fluorine, chlorine, bromine or iodine atom, by a $C_{1-3}$-alkyl or trifluoromethyl group, the tautomers, diastereomers, enantiomers, mixtures and salts thereof.

9. Compounds of general formula I according to claim 3, wherein

R, X, Z, A, n, $R^2$, and $R^5$ are defined as in claim 3 and $R^3$ and $R^4$ together denote a 1,3-butadien-1,4-ylene group wherein a hydrogen atom may be replaced by a fluorine, chlorine, bromine or iodine atom, by a $C_{1-3}$-alkyl, trifluoromethyl, hydroxy, $C_{1-3}$-alkoxy, carboxy, $C_{1-3}$-alkoxy-carbonyl, aminocarbonyl, $C_{1-3}$-alkyl-aminocarbonyl, di-($C_{1-3}$-alkyl)-aminocarbonyl or di-($C_{1-3}$-alkyl)-amino-$C_{2-3}$-alkyl-aminocarbonyl group or by a 5- to 7-membered cycloalkyleneimino-carbonyl group, while the methylene group in the 4 position of the 6-membered cycloalkyleneimino moiety may be replaced by a -NH, -N($C_{1-3}$-alkyl) or -N($C_{1-3}$-alkyl-carbonyl) group, and a second hydrogen atom may optionally be replaced by a fluorine, chlorine, bromine or iodine atom or by a $C_{1-3}$-alkyl group, the tautomers, diastereomers, enantiomers, mixtures and salts thereof 10. The following compounds of general formula I according to claim 1:

methyl 2-((R)-2-(4-amino-3,5-dibromo-phenyl)-1-{[4-(2-oxo-1,4-dihydro-3H-quinazolin-3-yl)-piperidin-1-carbonyl]-amino}-ethyl)-1H-benzimidazole-5-carboxylate, and 4-(2-oxo-1,4-dihydro-2H-quinazolin-3-yl)-piperidin-1-carboxylic acid-{(R)-2-(4-amino-3,5-dibromo-phenyl)-1-[1-(3-dimethylamino-propyl)-5-phenyl-1H-imidazol-2-yl]-ethyl}-amide, and their stereoisomers and salts.

11. Physiologically acceptable salts of the compounds according to claim 1, with inorganic or organic acids or bases.

12. Pharmaceutical compositions containing a therapeutically effective amount of a compound according to claim 1 together with one or more inert carriers and/or diluents.

13. A method for treatment of headaches migraine and cluster headaches comprising administering to a patient in need of such treatment a therapeutically effective amount of a compound according to claim 1.

14. A method of treating non-insulin-dependent diabetes mellitus (NIDDM) comprising administering to a patient in need of such treatment a therapeutically effective amount of a compound according to claim 1.

* * * * *